United States Patent
Puttick et al.

(10) Patent No.: US 12,419,977 B2
(45) Date of Patent: Sep. 23, 2025

(54) RADIOPHARMACEUTICALS

(71) Applicant: AdvanCell Isotopes Pty Limited, Sydney (AU)

(72) Inventors: Simon Puttick, Sydney (AU); William Tieu, Sydney (AU); Kevin Kuan, Sydney (AU)

(73) Assignee: AdvanCell Isotopes Pty Limited, Sydney (AU)

( * ) Notice: Subject to any disclaimer, the term of this patent is extended or adjusted under 35 U.S.C. 154(b) by 0 days.

(21) Appl. No.: 18/947,606

(22) Filed: Nov. 14, 2024

(65) Prior Publication Data

US 2025/0064994 A1 Feb. 27, 2025

Related U.S. Application Data

(63) Continuation of application No. PCT/AU2023/050763, filed on Aug. 11, 2023.

(30) Foreign Application Priority Data

Aug. 11, 2022 (AU) ................. 2022902273
Aug. 11, 2022 (AU) ................. 2022902274

(51) Int. Cl.
*A61K 51/04* (2006.01)
*C07B 59/00* (2006.01)

(52) U.S. Cl.
CPC ........ *A61K 51/0482* (2013.01); *C07B 59/002* (2013.01); *A61K 2121/00* (2013.01); *C07B 2200/05* (2013.01)

(58) Field of Classification Search
CPC ............ A61K 51/0482; A61K 2121/00; C07B 59/002; C07B 2200/05
USPC ....................................... 424/1.65
See application file for complete search history.

(56) References Cited

U.S. PATENT DOCUMENTS

2022/0016274 A1* 1/2022 McCann ................ A61P 35/00

FOREIGN PATENT DOCUMENTS

| KR | 20220006286 A | 1/2022 | |
|---|---|---|---|
| WO | 2018108287 A1 | 6/2018 | |
| WO | WO-2019240884 A2 * | 12/2019 | ........... A61K 31/395 |
| WO | 2021217122 A1 | 10/2021 | |
| WO | WO-2023215333 A1 * | 11/2023 | ............. A61P 35/00 |

OTHER PUBLICATIONS

International Search Report and Written Opinion for PCT/AU2023/050763, dated Sep. 25, 2023.
International-Type Search Report for AU2022902274, dated Jan. 31, 2023.
Weineisen, M. et al.; "68Ga- and 177Lu-Labeled PSMA I&T: Optimization of a PSMA-Targeted Theranostic Concept and First Proof-of-Concept Human Studies"; J. Nucl. Med., 56, 1169-1176 (2015).
Benešová et al., "Preclinical Evaluation of a Tailor-Made DOTA-Conjugated PSMA Inhibitor with Optimized Linker Moiety for Imaging and Endoradiotherapy of Prostate Cancer", Jun. 2015, Journal of Nuclear Medicine, vol. 56 (6), pp. 914-920.
Manallack, "The pK(a) Distribution of Drugs: Application to Drug Discovery", 2007, Perspectives in Medicinal Chemistry, vol. 1, pp. 25-38.
Sartor et al., "Lutetium-177-PSMA-617 for Metastatic Castration-Resistant Prostate Cancer", 2021, The New England Journal of Medicine, vol. 285, pp. 1091-1103.
Heynickx et al., "The salivary glands as a dose of limiting organ of PSMA-targeted radionuclide therapy: A review of the lessons learnt so far", 2021, Nuclear Medicine and Biology 98-99, pp. 30-39.
Yadav et al., "Efficacy and safety of 225Ac-PSMA-617 targeted alpha therapy in metastatic castration-resistant Prostate Cancer patients", 2020, Theranostics, vol. 10(20), pp. 9364-9377.
Griffiths et al., "First-in-Human 212Pb-PSMA-Targeted α-Therapy SPECT/CT Imagining in a Patient with Metastatic Castration-Resistant Prostate Cancer", Feb. 29, 2024, Journal of Nuclear Medicine, p. 1.

* cited by examiner

*Primary Examiner* — Michael G. Hartley
*Assistant Examiner* — Sean R Donohue
(74) *Attorney, Agent, or Firm* — DLA Piper LLP

(57) ABSTRACT

This application relates generally to prostate specific membrane antigen (PSMA) targeting compounds which may be complexed to a radioisotope. Pharmaceutical compositions including such compounds also disclosed. Such compounds or pharmaceutical compositions may be used in nuclear medicine for the in-vivo imaging of various tissues, and the treatment and/or prevention of various PSMA-expressing cancers, especially prostate cancer.

29 Claims, 3 Drawing Sheets

RADIOPHARMACEUTICALS

CROSS-REFERENCE TO RELATED APPLICATIONS

The present application is a bypass continuation of International Patent Application No. PCT/AU2023/050763 filed on 11 Aug. 2023, which claims priority from Australian Provisional Patent Application No. 2022902273 filed on 11 Aug. 2022, and Australian Provisional Patent Application No. 2022902274 filed on 11 Aug. 2022, the contents of which are incorporated herein by reference in their entirety.

FIELD

The present disclosure relates generally to prostate specific membrane antigen (PSMA) targeting compounds, including radiopharmaceuticals comprising the PSMA targeting compounds. In particular, the present disclosure relates to a compound of Formula (1), or a pharmaceutically acceptable salt, solvate, or stereoisomer thereof, which may be used either to prepare a radiopharmaceutical, or once complexed to a radioisotope, as a radiopharmaceutical. The present disclosure also relates generally to compositions comprising the compound of Formula (1), or a pharmaceutically acceptable salt, solvate, or stereoisomer thereof, and when complexed with a radioisotope, its use as a radiopharmaceutical in nuclear medicine for the in-vivo imaging of various tissues, and the treatment and/or prevention of various PSMA-expressing cancers, especially prostate cancer. The present disclosure also generally relates to methods for preparing a compound of Formula (1).

BACKGROUND

Prostate cancer is the most common cancer among men. One promising way of therapy for prostate cancer is the use of targeting radiopharmaceuticals i.e. drugs which are labelled with a radioisotope and are able to target the cancer cells so as to deliver a toxic level of radiation to the cancer cells whilst sparing normal healthy tissues. Typically, radiopharmaceuticals designed to target prostate cancer cells are conjugate compounds comprising a targeting ligand with high affinity for prostate cancer cells, in some cases a linker (or spacer) such as a peptide, and a chelator moiety which can complex to the radioisotope.

Prostate-specific membrane antigen (PSMA), also known as folate hydrolase I (FOLH1) and glutamate carboxypeptidase II (GCPII), is a trans-membrane glycoprotein which is primarily expressed in normal human prostate epithelium but which is overexpressed in prostate cancer, including metastatic cancer. Since PSMA is overexpressed in all prostate cancers and its expression is further increased in poorly differentiated, metastatic and hormone-refractory carcinomas, it is a very attractive target for PSMA-expressing cancer imaging and therapy.

Two conjugates currently being investigated as having potential as radiopharmaceuticals for treating prostate cancer include the conjugate DOTA-PSMA-617, also known as PSMA-617 and the conjugate DOTAGA-PSMA-I&T, also known as PSMA-I&T. PSMA-617 and PSMA-I&T complexed with $^{177}$Lu ([$^{177}$Lu]Lu-PSMA-617 and [$^{177}$Lu]Lu-PSMA-I&T), are currently considered two of the most promising conjugates for treating prostate cancers, with [$^{177}$Lu]Lu-PSMA-617 having been approved by the FDA for the treatment of adult patients with PSMA-positive metastatic castration-resistant prostate cancer (mCRPC) who have been treated with androgen receptor pathway inhibition and a taxane-based chemotherapy on Mar. 23 2022. However, while [$^{177}$Lu]Lu-PSMA-I&T exhibits higher initial uptake in tumour metastases and a lower mean whole body dose and lower dose to the lacrimal glands compared to [$^{177}$Lu]Lu-PSMA-617, it also shows high uptake in kidneys soon after injection resulting in longer clearance times (Schuchardt et al. *Journal of Nuclear Medicine*, 2022, 63(8), 1199-1207). The low tumour to kidney ratio of [$^{177}$Lu]Lu-PSMA-I&T represents a high risk of kidney toxicity which can be seen to be a potential dose limiting factor for treatment with [$^{177}$Lu]Lu-PSMA-I&T. For alpha-emitting radioisotopes such as $^{212}$Pb, such high initial kidney uptake represents a particular toxicity concern.

In light of the above, there is a need to identify new PSMA-conjugates that demonstrate an improved in in-vivo biodistribution following injection, such as reduced kidney uptake, and/or faster kidney clearance whilst retaining high tumour uptake and efficacy, or at least provide the public with a useful alternative.

SUMMARY

The present inventors have undertaken research and development into new PSMA-conjugates. In particular, the present inventors have surprisingly found that by modifying the nature of the chelator moiety, PSMA-conjugate compounds of Formula (1) complexed to a radioisotope (such as $^{212}$Pb) show good uptake in tumour tissue together with reduced retention in the kidneys following intravenous injection, especially compared to other clinical candidates, such as [$^{212}$Pb]Pb-PSMA-I&T. According to some embodiments or examples described herein, the PSMA-conjugate compounds of Formula (1) demonstrate a much higher tumour to kidney ratio post-injection compared to [$^{212}$Pb]Pb-PSMA-I&T. According to some embodiments or examples described herein, the present inventors have surprisingly discovered that the PSMA-conjugate, HO-Glu-CO-Lys[SubA-D-Lys-D-Phe-D-Tyr(3I)-(Pent-$^{212}$Pb-DO3AM)]—OH (chemical name 3S,7S,26S,29R,32R)-29-benzyl-32-(4-hydroxy-3-iodobenzyl)-5,13,20,28,31,34-hexaoxo-37-(4,7,10-tris(2-amino-2-oxoethyl)-1,4,7,10-tetraazacyclododecan-1-yl)-4,6,12,21,27,30,33-heptaazaheptatriacontane-1,3,7,26,37-pentacarboxylic acid); referred to herein as "[$^{212}$Pb]Pb-ADVC001", demonstrated high specific uptake within PSMA-expressing tumours with very low uptake in other organs and control tumour sites, including a high tumour to kidney ratio. Other advantages associated with the disclosed compounds are also described herein.

In one aspect, there is provided a compound of Formula (1), or a pharmaceutically acceptable salt, solvate or stereoisomer thereof;

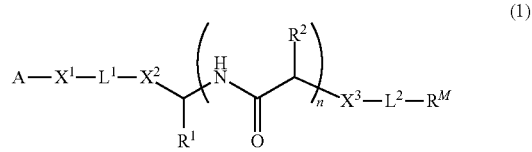

(1)

wherein:
n is 0 to 3;
A is a PSMA targeting ligand;
$X^1$ to $X^3$ are each independently absent or selected from the group consisting of —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O)NR$^3$—, —OS(=O)$_2$—, —N(R$^3$)C(=S)N(R$^3$)— and —N(R$^3$)C(=O)N(R$^3$)—;
$L^1$ and $L^2$ are each independently absent or a divalent linking moiety;
$R^1$ and each $R^2$ are independently selected from the group consisting of aryl, alkylaryl, heteroaryl and alkylheteroaryl, each of which is optionally substituted.
each $R^3$ is independently selected from the group consisting of H, alkyl, alkenyl, alkynyl, carbocyclyl, heterocyclyl, alkylcarbocyclyl, and alkylheterocyclyl, each of which is optionally substituted; and
$R^M$ is chelating moiety having the structure of Formula (M-1)

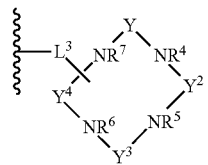

(M-1)

wherein:
$Y^1$ to $Y^4$ are each independently an optionally substituted —C$_{1-6}$alkyl-;
$R^4$ to $R^7$ are each independently selected from the group consisting of —C(=O)N(R$^3$)$_2$, —P(=O)(OR$^3$)$_2$, —P(=O)OR$^3$(R$^3$), —P(=O)(R$^3$)$_2$, —C$_{1-10}$alkylC(=O)N(R$^3$)$_2$, —C$_{1-10}$alkylP(=O)(OR$^3$)$_2$, —C$_{1-10}$alkylP(=O)OR$^3$(R$^3$) and —C$_{1-10}$alkylP(=O)(R$^3$)$_2$, or one of $R^4$ and $R^6$ or $R^5$ and $R^7$ together from a —(CH$_2$)$_m$— bridge; wherein each C$_{1-10}$alkyl is optionally substituted, or one of $R^4$ to $R^7$ is a bond connecting the ring to $L^3$ or the rest of the molecule of Formula (1);

$L^3$ is absent and the ring is directly connected to the rest of the molecule of Formula (1) via any ring heteroatom or any one of $Y^1$ to $Y^4$, or $L^3$ is a divalent linking moiety connecting the ring to the rest of the molecule of Formula (1) via any ring heteroatom or any one of $Y^1$ to $Y^4$;

$\sim\!\!\sim$ represents the bond which attaches $R^M$ to $L^2$ in Formula (1);
m is 1 to 3; and
wherein $R^M$ is optionally complexed to a radioisotope.
In one embodiment, the compound of Formula (1) is

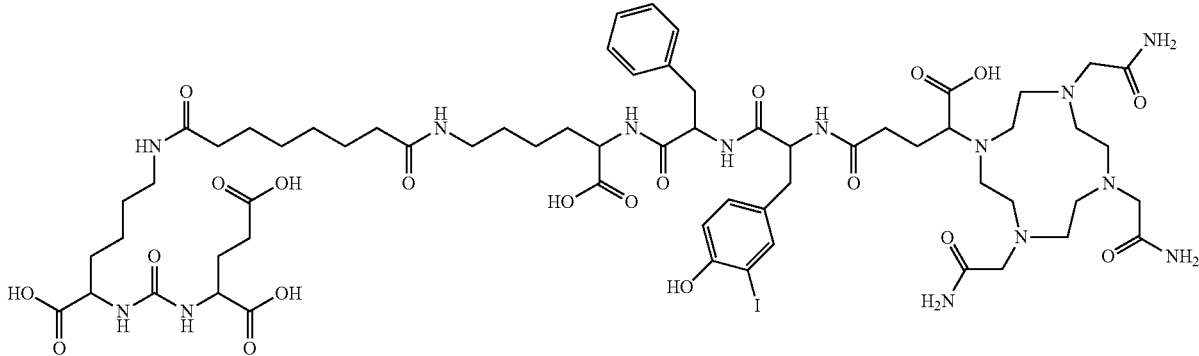 [SMILES: NC(=O)CN1CCN(CC(N)=O)CCN(C(CCC(=O)NC(Cc2ccc(O)c(I)c2)C(=O)NC(Cc2ccccc2)C(=O)NC(CCCCNC(=O)CCCCCCC(=O)NCCCCC(NC(=O)NC(CCC(=O)O)C(=O)O)C(=O)O)C(=O)O)C(=O)O)CCN(CC(N)=O)CC1]

In one embodiment, the compound of Formula (1) is selected from the group consisting of:

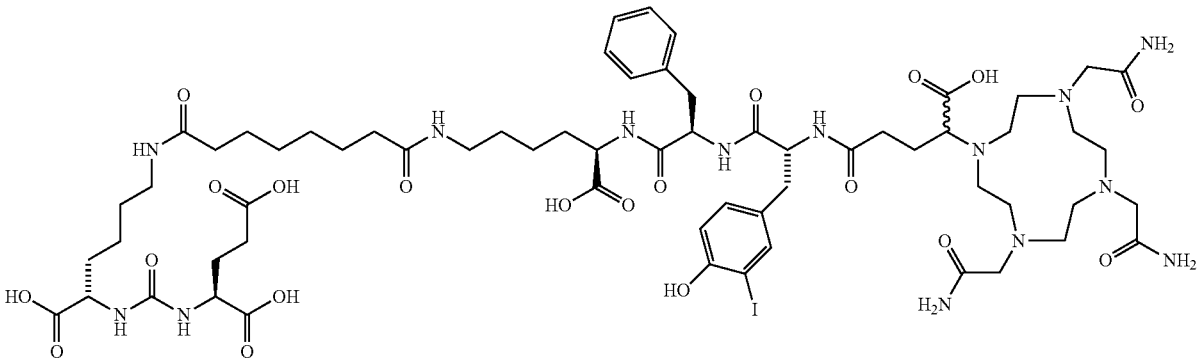 [SMILES: NC(=O)CN1CCN(CC(N)=O)CCN(C(CCC(=O)NC(Cc2ccc(O)c(I)c2)C(=O)NC(Cc2ccccc2)C(=O)NC(CCCCNC(=O)CCCCCCC(=O)NCCCCC(NC(=O)NC(CCC(=O)O)C(=O)O)C(=O)O)C(=O)O)C(=O)O)CCN(CC(N)=O)CC1]

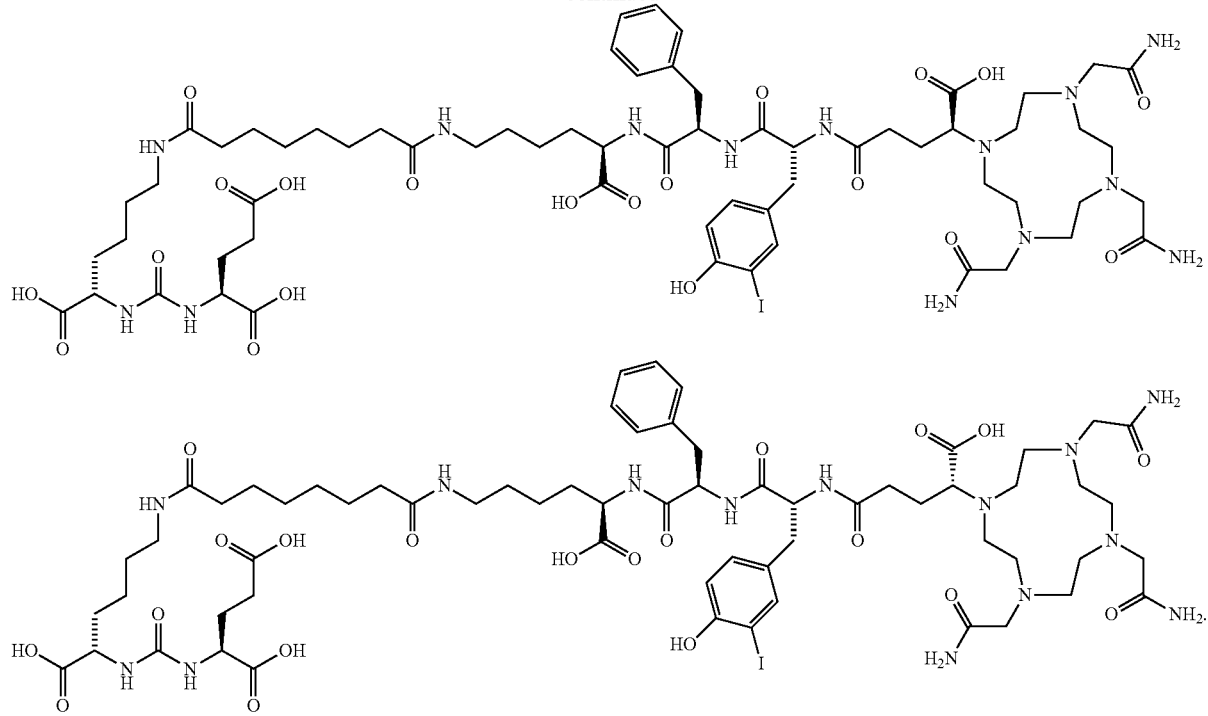

In one embodiment, $R^M$ is complexed to a radioisotope, including a radioisotope selected from the group consisting of $^{44}$Sc, $^{47}$Sc, $^{51}$Mn, $^{52m}$Mn, $^{52g}$Mn, $^{55}$Co, $^{58}$Co, $^{58m}$Co, $^{61}$Co $^{61}$Cu $^{62}$Cu $^{64}$Cu, $^{67}$C, $^{68}$Ga, $^{86}$Y $^{90}$Y $^{89}$Zr, $^{111}$In, $^{134}$La, $^{152}$Eu, $^{149}$Tb, $^{152}$Tb, $^{155}$Tb, $^{161}$Tb $^{177}$Lu, $^{203}$Pb, $^{211}$Pb, $^{212}$Pb, $^{212}$Bi, $^{213}$Bi, $^{225}$Ac, and $^{227}$Th In another aspect, there is provided a compound of Formula (1L), or a pharmaceutically acceptable salt, solvate or stereoisomer thereof;

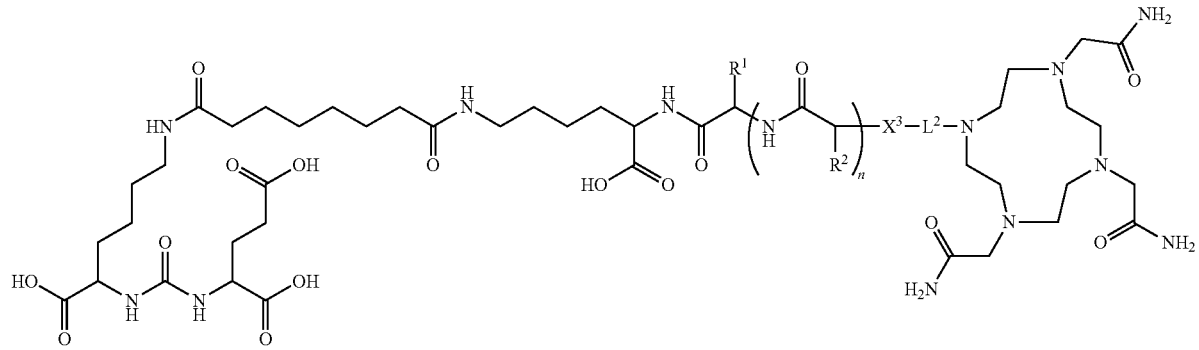

(1L)

wherein:

n is 0 to 3;

$X^3$ is absent or selected from the group consisting of —O—, —S—, —C(=O)—, —C(=O)NR$^3$—, —NR$^3$—, —C(=O)O—, —C(=O)S—, —S(=O)$_2$—, —S(=O)$_2$NR$^3$— —S(=O)NR$^3$—, —OS(=O)$_2$—, —N(R$^3$)C(=S)N (R$^3$)— and —N(R$^3$)C(=O)N(R$^3$)—;

$L^2$ is absent or is an aliphatic linker group which is uninterrupted or interrupted, and optionally substituted;

$R^1$ and each $R^2$ are independently selected from the group consisting of aryl, alkylaryl, heteroaryl and alkylheteroaryl, each of which is optionally substituted;

each $R^3$ is independently selected from the group consisting of H, alkyl, alkenyl, alkynyl, carbocyclyl, heterocyclyl, alkylcarbocyclyl, and alkylheterocyclyl, each of which is optionally substituted; and wherein the compound is optionally complexed to a radioisotope.

In one embodiment, $X^3$ is absent or selected from the group consisting of —O—, —S—, —C(=O)—, —C(=O) NR$^3$—, —NR$^3$—, —C(=O)O—, —C(=O)S—, —S(=O)$_2$—, —S(=O)$_2$NR$^3$—, —S(=O)NR$^3$—, —OS(=O)$_2$—, —N(R$^3$)C(=S)N (R$^3$)— and —N(R$^3$)C(=O)N(R$^3$)—;

$L^2$ is absent or is an aliphatic linker group which is uninterrupted or interrupted with one or more groups selected from —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)—, and —N(R$^3$)C(=O)N(R$^3$)—;

$R^1$ and each $R^2$ are independently selected from the group consisting of aryl, alkylaryl, heteroaryl and alkylheteroaryl, each $R^3$ is independently selected from the group consisting of H, alkyl, alkenyl, alkynyl, carbocyclyl, heterocyclyl, alkylcarbocyclyl, and alkylheterocyclyl, wherein each of $L^2$ and $R^1$ to $R^3$ is optionally substituted with one or more $R^8$;

each $R^1$ is independently selected from the group consisting of H, halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, —NO$_2$, —CN, —SCN, —N$_3$, =O, —N(R$^9$)$_2$, —C(=O)N(R$^9$)$_2$, —S(=O)N(R$^9$)$_2$, —S(=O)$_2$N(R$^9$)$_2$, —OR$^9$, —SR$^9$, —OC(=O)R$^9$, —C(=O)R$^9$, —C(=O)OR$^9$, —S(=O)R$^9$, —S(=O)$_2$R$^9$, —S(=O)OR$^9$, —S(=O)$_2$OR$^9$, —S(=O)(OR$^9$)$_2$, —OS(=O)R$^9$, —OS(=O)$_2$R$^9$, —OS(=O)OR$_9$, —OS(=O)$_2$OR$^9$, —OS(=O)(OR$^9$)$_2$, —N(R$^9$)C(=O)R$^9$, —N(R$^9$)S(=O)R$^9$, —N(R$^9$)C(=O)N(R$^9$)$_2$, —N(R$^9$)S(=O)$_2$R$^9$, —P(=O)(OR$^9$)$_2$, —P(=O)OR$^9$(R$^9$), —P(=O)(R$^9$)$_2$, —OP(=O)(OR$^9$)$_2$, —OP(=O)OR$^9$(R$^9$) and —OP(=O)(R$^9$)$_2$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$;

each $R^9$ is independently selected from the group consisting of H, $C_{1-6}$alkyl, 3-10 membered carbocyclyl, 3-10-membered heterocyclyl, $C_{1-6}$alkyl-3-10-membered-carbocyclyl, and $C_{1-6}$alkyl-3-10-membered-heterocyclyl; wherein each $C_{1-6}$alkyl, 3-10-membered-carbocyclyl, and 3-10-membered heterocyclyl is optionally substituted with one or more $R^{10}$;

each $R^{10}$ is independently selected from the group consisting of H, halogen, —NO$_2$, —N(R$^{11}$)$_2$, —CN, —SCN, —N$_3$, =O, —C(=O)R$^{11}$, —C(=O)OR$^{11}$, —C(=O)N(R$^{11}$)$_2$, —N(R$^{11}$)C(=O)R$^{11}$, —OR$^{11}$, —P(=O)(OR$^{11}$)$_2$, —P(=O)OR$^{11}$(R$^{11}$), —P(=O)(R$^{11}$)$_2$, $C_{1-6}$alkyl, and —OC$_{1-6}$alkyl, each $R^{11}$ is independently selected from the group consisting of H, $C_{1-10}$alkyl, $C_{1-10}$alkyl, $C_{2-10}$alkenyl, $C_{2-10}$alkynyl, 3-10 membered carbocyclyl, 3-10 membered heterocyclyl, $C_{1-10}$alkyl-3-10-membered carbocyclyl, $C_{1-10}$alkyl-3-10-membered heterocyclyl.

In one embodiment, $L^2$ is $C_{1-10}$alkyl- or —$C_{2-10}$alkyl-, wherein each alkyl is independently optionally substituted with one or more $R^8$.

In one embodiment, $L^2$ is optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, —N(R$^9$)$_2$, —C(=O)N(R$^9$)$_2$, —OR$^9$, —OC(=O)R$^9$, —C(=O)R$^9$, —C(=O)OR$^9$, and —N(R$^9$)C(=O)R$^9$, wherein each $C_{1-10}$alkyl, $C_{1-10}$haloalkyl, $C_{2-10}$alkenyl, $C_{2-10}$alkynyl, 3-10-membered-carbocyclyl, and 3-10-membered-heterocyclyl is optionally substituted with one or more $R^{10}$.

In one embodiment, $L^2$ is optionally substituted with one or more groups selected from $C_{1-10}$alkyl, $OC_{1-10}$alkyl, —NH$_2$, —OH, —COOH, and —C(=O)OC$_{1-6}$alkyl.

In one embodiment, $X^3$ is selected from the group consisting of —O—, —S—, —C(=O)—, —C(=O)NH—, —NH—, —C(=O)O—, —C(=O)S—, —S(=O)$_2$—, —NHC(=S)NH—, and —NHC(=O)NH—.

In one embodiment, $X^3$ is —C(=O)NH—

In one embodiment, the moiety —$X^3$-$L^2$- in Formula (1L) has the structure (L-2) or (L-3):

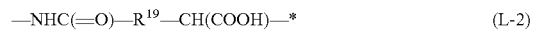  (L-2)

  (L-3)

wherein:

$R^{19}$ is a $C_{1-10}$alkyl or $C_{2-10}$alkyl optionally substituted with one or more $R^8$

* indicates the bond which is attached to the cyclic N in Formula (1L).

In one embodiment, the moiety —$X^3$-$L^2$- in Formula (1L) has the structure (L-2):

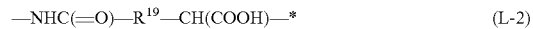  (L-2)

wherein:

$R^{19}$ is $C_{1-10}$alkyl or $C_{2-10}$alkyl optionally substituted with one or more $R^8$; and

* indicates the bond which is attached to the cyclic N in Formula (1L).

In one embodiment, $R^1$ and $R^2$ are each independently an optionally substituted alkylaryl or an optionally substituted alkylheteroaryl.

In one embodiment, $R^1$ and $R^2$ are each independently an optionally substituted alkylaryl.

In one embodiment, $R^1$ and $R^2$ are each independently an optionally substituted benzyl.

In one embodiment, $R^1$ and $R^2$ are each independently optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —NO$_2$, —N(R$^{11}$)$_2$, —CN, —SCN, —N$_3$, =O, —C(=O)R$^{11}$, —C(=O)OR$^{11}$, —N(R$^{11}$)C(=O)R$^{11}$, and —OR$^1$.

In one embodiment, $R^1$ and $R^2$ are benzyl, each independently optionally substituted with one or more groups selected from halogen, —NO$_2$, —NH$_2$, —CN, —SCN, —COOH and —OH.

In one embodiment, $R^1$ is benzyl, and $R^2$ is benzyl substituted with one or more groups selected from halogen, —NO$_2$, —NH$_2$, —CN, —SCN, —COOH and —OH. In one embodiment, the compound of Formula (1L) is

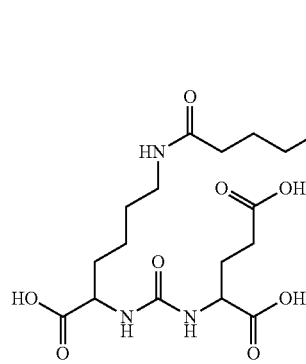
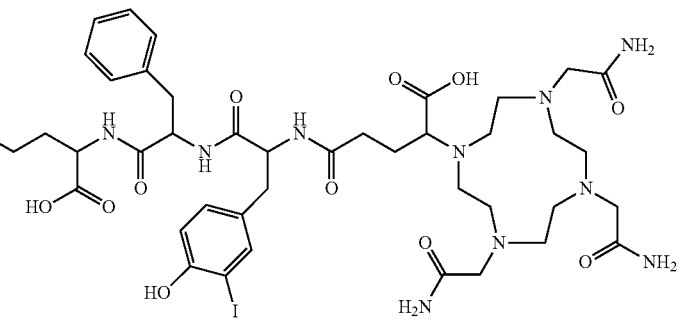

In one embodiment, the compound of Formula (1L) is selected from the group consisting of:

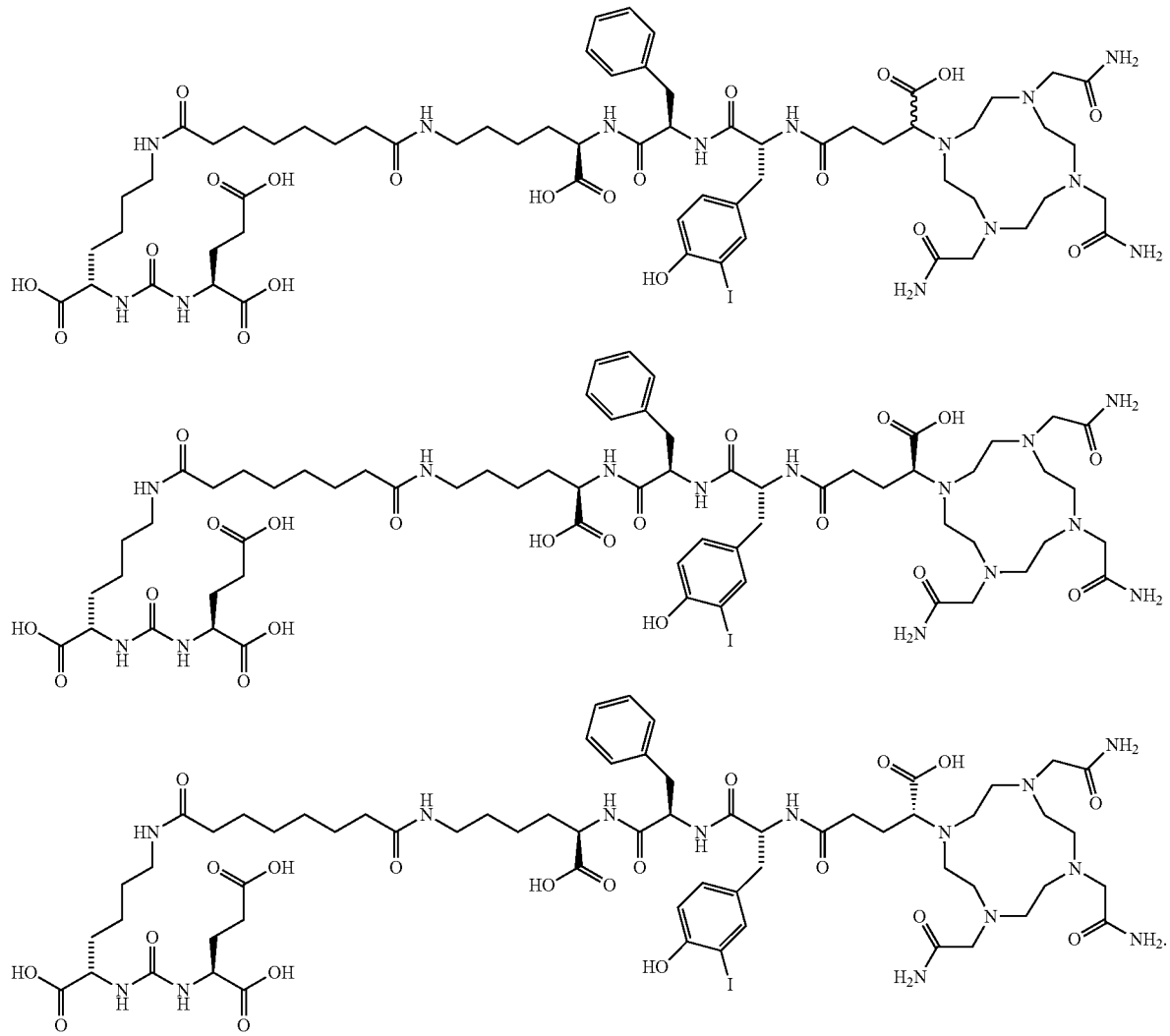

In one embodiment, the compound of Formula (1L) is complexed to a radioisotope.

In one embodiment, the compound of Formula (1L) is complexed to a radioisotope selected from the group consisting of $^{44}$Sc, $^{47}$Sc, $^{51}$Mn, $^{52m}$Mn, $^{52g}$Mn, $^{55}$Co, $^{58}$Co, $^{58m}$Co, $^{61}$Co, $^{61}$Cu, $^{62}$Cu, $^{64}$Cu, $^{67}$Cu, $^{68}$Ga, $^{86}$Y, $^{90}$Y, $^{89}$Zr, $^{111}$In, $^{134}$La, $^{152}$Eu, $^{149}$Tb, $^{152}$Tb, $^{155}$Tb, $^{161}$Tb, $^{177}$Lu, $^{203}$Pb, $^{211}$Pb, $^{212}$Pb, $^{212}$Bi, $^{213}$Bi, $^{225}$Ac, and $^{227}$Th.

In one embodiment, the compound of Formula (1L) is complexed to $^{212}$Pb.

In another aspect, there is provided a compound of Formula (1), including any one of compounds Formula (1A) to (1L), as defined herein, for use in diagnosing, treating and/or preventing a PSMA-expressing cancer.

In another aspect, there is provided a pharmaceutical composition comprising a compound of Formula (1), including any one of compounds Formula (1A) to (1L), as defined herein, and a pharmaceutically acceptable excipient.

In another aspect, there is provided a method for treating and/or preventing a PSMA-expressing cancer in a subject in need thereof, comprising administering a therapeutically effective amount a compound of Formula (1), including any one of compounds Formula (1A) to (1L), as defined herein or a pharmaceutical composition as defined above to the subject.

In another aspect, there is provided use of a compound of Formula (1), including any one of compounds Formula (1A) to (1L), as defined herein or a pharmaceutical composition as defined above for treating and/or preventing a PSMA-expressing cancer.

In another aspect, there is provided use of a compound of Formula (1), including any one of compounds Formula (1A) to (1L), as defined herein or a pharmaceutical composition as defined above in the manufacture of a medicament for treating and/or preventing a PSMA-expressing cancer.

In one embodiment, the PSMA-expressing cancer is prostate cancer, preferably metastatic castrate-resistant prostate cancer (mCRPC).

In another aspect, there is provided an imaging agent comprising the compound of Formula (1), including any one of compounds Formula (1A) to (1L), as defined herein.

In one embodiment, the compound is complexed to a positron-emitting radioisotope or a gamma-emitting radioisotope. In one embodiment, the positron-emitting radioisotope is selected from the group consisting of $^{68}$Ga, $^{64}$Cu, $^{55}$Co and 89Z In another aspect, there is provided a diagnostic composition comprising the imaging agent as defined above, and a pharmaceutically acceptable excipient.

In another aspect, there is provided a method of imaging a tissue in a subject, comprising administering a diagnostically effective amount of the imaging agent as defined above or the diagnostic composition as defined above to the subject.

In another aspect, there is provided use of an imaging agent as defined above or the diagnostic composition as defined above for imaging a tissue in a subject.

In another aspect, there is provide an ex-vivo method of imaging a tissue sample comprising a diagnostically effective amount of the imaging agent as defined above or the diagnostic composition as defined above.

In another aspect, there is provided use of a compound as defined above or a pharmaceutical composition as defined above in the manufacture of an imaging agent for imaging a tissue in a subject.

In one embodiment, the tissue is a PSMA-expressing tumour tissue. In one embodiment, the PSMA-expressing tumour tissue is prostate cancer, preferably metastatic castrate-resistant prostate cancer (mCRPC).

In another aspect, there is provided a method for preparing a compound of Formula (1), including any one of compounds Formula (1A) to (1L), or a salt or solid supported derivative thereof, comprising coupling a compound of Formula (R-1) with a compound of Formula (S-1):

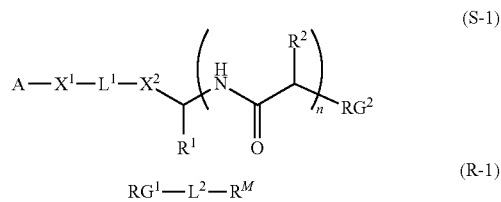

wherein:
RG$^1$ and RG$^2$ are each independently a reactive coupling group;
n, A, X$^1$, L$^1$, X$^2$, R$^1$, R$^2$, L$^2$ and R$^M$ are described herein, and
wherein the compound of Formula (S-1) is optionally attached to a solid support.

In another aspect, there is provided a method of preparing a compound of Formula (1L), or a salt or solid supported derivative thereof, the method comprising coupling a compound of Formula (R-2) with a compound of Formula (S-2):

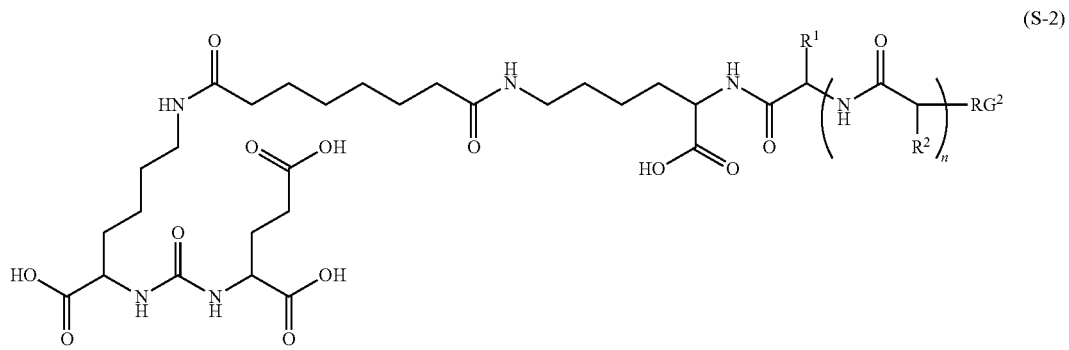

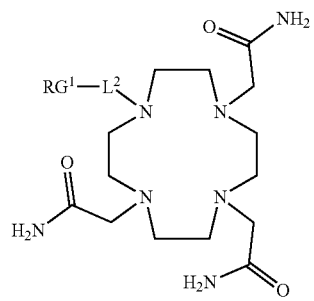

(R-2)

wherein:
RG$^1$ and RG$^2$ are each independently a reactive coupling group; and
n, L$^2$, R$^1$ and R$^2$ are described herein,
wherein the compound of Formula (S-2) is optionally attached to a solid support.

Other aspects and embodiments relating to the present disclosure are described herein. It will be appreciated that each example, aspect and embodiment of the present disclosure described herein is to be applied mutatis mutandis to each and every other example, aspect or embodiment unless specifically stated otherwise. For example, each example, aspect and embodiment of the compound of Formula (1) described herein may apply equally to one or more of the compounds of Formula (1A) to (1L), pharmaceutical composition, imaging agents, diagnostic compositions, processes, methods and uses described herein, and vice versa. For example, the compounds of Formula (1A) to (1L) each fall within the scope of the compound of Formula (1), and as such the substituents described herein in relation to Formula (1) equally apply to one or more of the compounds of Formula (1A) to (1L), where applicable, and vice versa. The present disclosure is not to be limited in scope by the specific examples described herein, which are intended for the purpose of exemplification only. Functionally-equivalent substituents, compositions, methods and processes are clearly within the scope of the disclosure as described herein.

BRIEF DESCRIPTION OF FIGURES

Embodiments of the present disclosure are further described and illustrated as follows, by way of example only, with reference to the accompanying drawings in which.

DETAILED DESCRIPTION

Figure 1A:
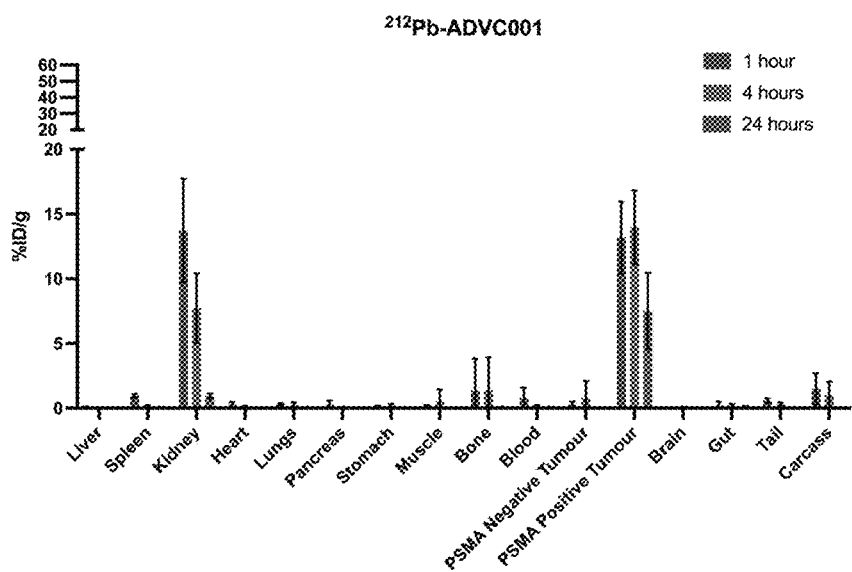
FIGS. 1A and 1B: A) Uptake and retention of [$^{212}$Pb]Pb-ADVC001 in kidneys (% injected dose per gram (% ID/g) 1 hour (green), 4 hours (blue) and 24 hours (red) post-injection. B) Uptake and retention of [$^{212}$Pb]Pb-PSMA-I&T (% ID/g) 1 hour (green), 4 hours (blue) and 24 hours (red) post-injection.

The present disclosure describes the following various non-limiting embodiments, which relate to investigations undertaken to develop compounds which can be used as PSMA ligands.

General Terms

In the following description, reference is made to the accompanying drawings which form a part hereof, and which is shown, by way of illustration, several embodiments. It is understood that other embodiments may be utilized and structural changes may be made without departing from the scope of the present disclosure.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

All publications discussed and/or referenced herein are incorporated herein in their entirety.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

Throughout this disclosure, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the examples, steps, features, methods, hydrogels, processes, and compositions, referred to or indicated in this specification, individually or collectively, and any and all combinations or any two or more of said steps or features.

The term "and/or", e.g., "X and/or Y" shall be understood to mean either "X and Y" or "X or Y" and shall be taken to provide explicit support for both meanings or for either meaning.

Unless otherwise indicated, the terms "first," "second," etc. are used herein merely as labels, and are not intended to impose ordinal, positional, or hierarchical requirements on the items to which these terms refer. Moreover, reference to a "second" item does not require or preclude the existence of lower-numbered item (e.g., a "first" item) and/or a higher-numbered item (e.g., a "third" item).

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example and without limitation, two of item A, one of item B, and ten of item C; four of item B and seven of item C; or some other suitable combination.

As used herein, the term "about", unless stated to the contrary, typically refers to a range of up to +/−10% of the designated value, and includes smaller ranges therein, for example+/−5% or +/−1% of the designated value.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 4.5, 4.75, and 5, unless where integers are required or implicit from context. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Specific Terms

As used herein, the term "subject" refers to any organism susceptible to a disease or condition that requires therapy. For example, the subject can be a mammal, primate, livestock (e.g., sheep, cow, horse, pig), companion animal (e.g., dog, cat), or laboratory animal (e.g., mouse, rabbit, rat, guinea pig, hamster). In one example, the subject is a mammal. In one embodiment, the subject is human.

As used herein, the term "treating" or "treatment" includes alleviation of the symptoms associated with a specific disease or condition and reducing and/or eliminating said symptoms. For example, as used herein, the term "treating a PSMA-expressing cancer" refers to alleviating the symptoms associated with a PSMA-expressing cancer and/or eliminating the symptoms associated a PSMA expressing cancer, such as prostate cancer.

As used herein, the term "preventing" or "prevention" includes prophylaxis of the specific disorder or condition. For example, as used herein, the term "preventing a PSMA-expressing cancer" refers to preventing the onset or duration of the symptoms associated with a PSMA expressing cancer, such as prostate cancer.

As would be understood by the person skilled in the art, a compound of Formula (1), or a pharmaceutically acceptable salt, solvate, or stereoisomer thereof, can be administered in a therapeutically effective amount. The term "therapeutically effective amount", as used herein, refers to a compound of Formula (1), or a pharmaceutically acceptable salt, solvate, or stereoisomer thereof, being administered in an amount sufficient to alleviate or prevent to some extent one or more of the symptoms of the disorder or condition being treated. The result can be the reduction and/or alleviation of the signs, symptoms, or causes of a disease or condition, or any other desired alteration of a biological system. For example, one result may be the reduction of one or more symptoms associated with a PSMA-expressing cancer, such as prostate cancer. The term, "effective amount", as used herein, refers to an amount of a compound of Formula (1), or a pharmaceutically acceptable salt, solvate, or stereoisomer thereof, effective to achieve a desired pharmacologic effect or therapeutic improvement without undue adverse side effects. By way of example only, therapeutically effective amounts may be determined by routine experimentation, including but not limited to a dose escalation clinical trial. The term "therapeutically effective amount" includes, for example, a prophylactically effective amount. In one embodiment, a prophylactically effective amount is an amount sufficient to prevent a PSMA-expressing cancer, such as prostate cancer. It is understood that "an effective amount" or "a therapeutically effective amount" can vary from subject to subject, due to variation in metabolism of the compound and any of age, weight, general condition of the subject, the condition being treated, the severity of the condition being treated, and the judgment of the prescribing physician. Thus, it is not always possible to specify an exact "effective amount". However, an appropriate "effective amount" in any individual case may be determined by one of ordinary skill in the art using routine experimentation. Where more than one therapeutic agent is used in combination, a "therapeutically effective amount" of each therapeutic agent can refer to an amount of the therapeutic agent that would be therapeutically effective when used on its own, or may refer to an adjusted (e.g., reduced)

amount that is therapeutically effective by virtue of its combination with one or more additional therapeutic agents.

The term "onset" of activity, as used herein, refers to the length of time to alleviate or prevent to some extent one or more of the symptoms of the disorder or condition being treated following the administration of the compound of Formula (1). The term "duration" refers to the length of time that the therapeutic continues to be therapeutically effective, i.e., alleviate or prevent to some extent one or more of the symptoms of the disorder or condition being treated. The person skilled in the art would be aware that onset, peak, and duration of therapy may vary depending on factors such as the patient, the condition of the patient, and the route of administration.

The term "PSMA-expressing cancer" as used herein, refers to any cancer whose cancerous cells express Prostate Specific Membrane Antigen (PSMA) and the respective metastases thereof. Preferably, cancers (or cancer cells) that may be treated according to the invention are selected among prostate cancer, conventional renal cell cancers, cancers of the transitional cells of the bladder, testicular-embryonal cancers, neuroendocrine cancers, colon cancers, brain tumours and breast cancers. In particularly preferred examples, said PSMA-expressing cancer is prostate cancer or breast cancer, in particular prostate cancer. In one example, the PSMA-expressing cancer may be metastatic castrate-resistant prostate cancer (mCRPC).

As used herein, the term "PSMA targeting ligand" refers to a chemical moiety which targets PSMA.

The compounds of the present disclosure may contain chiral (asymmetric) centers or the molecule as a whole may be chiral. The individual stereoisomers (enantiomers and diastereoisomers) and mixtures of these are within the scope of the present disclosure.

The term "halo" or "halogen" whether employed alone or in compound words such as haloalkyl, represents fluorine, chlorine, bromine or iodine. Further, when used in compound words such as haloalkyl, the alkyl may be partially halogenated or fully substituted with halogen atoms which may be independently the same or different. Examples of haloalkyl groups include fluoromethyl, chloromethyl, bromomethyl, iodomethyl, fluoropropyl, fluorobutyl, difluoromethyl difluoroethyl, trifluoromethyl and trifluoroethyl groups. Further examples of haloalkyl groups include —$CF_3$, —$CCl_3$, and —$CH_2CF_3$, —$CF_2CF_3$ and —$CH_2CHFCl$.

As used herein, the term "alkyl" whether used alone, or in compound words such as haloalkyl, cycloalkyl, alkylcycloalkyl, alkylcarbocyclyl, heteroalkyl, alkylheterocyclyl, alkylheteroaryl, alkylamide, alkylphosphonate and alkylaryl, represents straight chain (i.e. linear) or branched chain hydrocarbon groups. Examples of alkyl groups include methyl, ethyl, n-propyl, iso-propyl, n-butyl, t-butyl, i-butyl, sec-butyl, pentyl, hexyl, heptyl, octyl, nonyl and decyl groups. In one example, the alkyl group is of 1 to 20 carbon atoms (i.e. $C_{1-20}$alkyl). In another examples, the alkyl is a group of 1 to 10 carbon atoms (i.e. $C_{1-10}$alkyl). In another example, the alkyl group is of 1 to 6 carbon atoms (i.e. $C_{1-6}$alkyl).

As used herein, the term "heteroalkyl" represents straight chain (i.e. linear) or branched chain hydrocarbon groups which are analogous to an alkyl group, but in which one or more carbon atoms is/are replaced by one or more heteroatoms selected from nitrogen, sulfur, and oxygen.

As used herein, the term "alkenyl" represents straight (i.e. linear) or branched chain unsaturated hydrocarbon groups containing at least one carbon-carbon double bond. Examples of alkenyl groups include ethylene, propenyl, butenyl, pentenyl, hexenyl, heptenyl, octenyl, nonenyl and decenyl groups. In one example, the alkenyl group is of 2 to 20 carbon atoms (i.e. $C_{2-20}$alkenyl). In another example, the alkenyl is a group 2 to 10 carbon atoms (i.e. $C_{2-10}$alkenyl). In another example, the alkenyl group is of 2 to 6 carbon atoms (i.e. $C_{2-6}$alkenyl)

As used herein, the term "alkynyl" represents straight (i.e. linear) or branched chain unsaturated hydrocarbon groups containing at least one carbon-carbon triple bond. Examples of alkenyl groups include, ethynyl, propynyl, butynyl, pentynyl, hexynyl, heptynyl, octynyl, nonynyl and decynyl groups. In one example, the alkynyl group is of 2 to 20 carbon atoms (i.e. $C_{2-20}$alkynyl). In one example, the alkynyl group is of 2 to 10 carbon atoms (i.e. $C_{2-10}$alkynyl). In another examples, the alkynyl group is of 2 to 6 carbon atoms (i.e. $C_{2-6}$alkynyl).

As used herein, the term "haloalkyl" represents to an alkyl group having at least one halogen substituent, where "alkyl" and "halogen" are as described above. For example, the haloalkyl group may have at least one, two or three halogen substituents. Examples of haloalkyl groups include fluoromethyl, chloromethyl, bromomethyl, iodomethyl, fluoropropyl, fluorobutyl, difluoromethyl difluoroethyl, trifluoromethyl and trifluoroethyl groups. Further examples of haloalkyl groups include —$CF_3$, —$CCl_3$, and —$CH_2CF_3$, —$CF_2CF_3$ and —$CH_2CHFCl$. In one example, the haloalkyl group is of 1 to 20 carbon atoms (i.e. $C_{1-20}$haloalkyl). In one example, the haloalkyl group is of 1 to 10 carbon atoms (i.e. $C_{1-10}$ haloalkyl). In another example, the haloalkyl group is of 1 to 6 carbon atoms (i.e. $C_{1-6}$haloalkyl).

As used herein, the terms "carbocyclyl" and "carbocycle" whether used alone, or in compound words such as alkylcarbocyclyl, represents a monocyclic or polycyclic ring system wherein the ring atoms are all carbon atoms, e.g., of about 3 to about 20 carbon atoms, and which may be aromatic, non-aromatic, saturated, or unsaturated, and may be substituted and/or contain fused rings. In one example, the carbocyclyl group is of 3 to 20 carbon atoms (i.e. $C_{3-20}$-membered carbocyclyl). In another example, the carbocyclyl group is of 3 to 10 carbon atoms (i.e. $C_{3-10}$-membered carbocyclyl). Examples of such groups include aryl groups such as phenyl, naphthyl, anthracenyl or fluorenyl, saturated groups such as cycloalkyl and cycloalkenyl groups e.g. cyclopropyl, cyclobutyl, cyclopentyl, cyclopentenyl, cyclohexyl, cyclohexenyl, cycloheptyl, cyclooctyl, cyclononyl, cyclodecyl groups, or fully or partially hydrogenated phenyl, naphthyl and fluorenyl. It will be appreciated that the polycyclic ring system includes bicyclic and tricyclic ring systems.

As used herein, the term "cycloalkyl" whether used alone, or in compound words such as alkylcycloalkyl, refers to a monocyclic or polycyclic carbocyclic ring system of varying sizes, e.g., from about 3 to about 20 carbon atoms, e.g., cyclopropyl, cyclobutyl, cyclopentyl, cyclopentenyl, cyclohexyl, cyclohexenyl, cycloheptyl, cyclooctyl, cyclononyl, cyclodecyl. It will be appreciated that the polycyclic ring system includes bicyclic and tricyclic ring systems.

As used herein, the term "heterocyclyl" whether used alone or in compound words such as alkylheterocyclyl, refers to a monocyclic or polycyclic ring system wherein the ring atoms are provided by at least two different elements, typically a combination of carbon and one or more of nitrogen, sulfur, and oxygen, and wherein the ring system may be aromatic such as a "heteroaryl" group, non-aromatic, saturated, or unsaturated, and may be substituted and/or contain fused rings. Heterocyclyl groups containing a suitable nitrogen atom include the corresponding N-oxides. In one example, the heterocyclyl group is of 3 to 20 atoms (i.e. 3-20-membered heterocyclyl). In another example, the heterocyclyl group is of 3 to 10 atoms (i.e. 3-10-membered heterocyclyl). The heteroatom may preferably be N, O or S. Examples of monocyclic non-aromatic heterocyclyl groups include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl. Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl, and benzoazepanyl. Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl (e.g. the radical derived from pyridine), triazolyl, triazinyl, pyridazyl, isothiazolyl, isoxazolyl, pyrazinyl, pyrazolyl, and pyrimidinyl. Examples of bicyclic aromatic heterocyclyl groups (also referred to as bicyclic heteroaryl groups) include quinoxalinyl, quinazolinul, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridyl, pyridopyrimidinyl, isoquinolinyl, and benzohydroxazole. It will be appreciated that the polycyclic ring system includes bicyclic and tricyclic ring systems.

As used herein, amino acids may be referred to by their full name, three letter code, or single letter code, all of which will be understood by the person skilled in the art.

As will be understood, an "aromatic" group means a cyclic group having 4m+2 π electrons, where m is an integer equal to or greater than 1. As used herein, "aromatic" is used interchangeably with "aryl" to refer to an aromatic group, regardless of the valency of aromatic group.

As used herein, the term "aryl" whether used alone, or in compound words such as alkylaryl, represents an monocyclic (e.g. phenyl) or polycyclic (e.g. naphthyl) aromatic carbocyclic ring system. In one example, the aryl group is of 3 to 20 carbon atoms (i.e., an aromatic 3-20 membered carbocyclyl). In another example, the aryl group is of 3 to 10 carbon atoms (i.e., an aromatic 3-10 membered carbocyclyl). Examples of aryl groups include, but are not limited to, phenyl, naphthyl, anthracenyl or fluorenyl. It will be appreciated that the polycyclic ring system includes bicyclic and tricyclic ring systems. Related to the term aryl, the term "aralkyl" as used herein refers to an alkyl group wherein a hydrogen atom is replaced by an aryl group as a substituent. Examples of alkylaryl groups include, but are not limited to, an optionally substituted benzyl (e.g. —CH$_2$-phenyl).

As used herein, the term "heteroaryl" whether used alone, or in compound words such as alkylheteroaryl, represents a monocyclic or polycyclic aromatic ring system wherein the ring atoms are provided by at least two different elements, typically a combination of carbon and one or more of nitrogen, sulfur, and oxygen, and may be substituted and/or contain fused rings. Heteroaryl groups containing a suitable nitrogen atom include the corresponding N-oxides. In one example, the heteroaryl group is of 3 to 20 atoms (i.e. 3-20-membered heteroaryl). In another example, the heteroaryl group is of 3 to 10 atoms (i.e. 3-10-membered heteroaryl). Examples of monocyclic heteroaryl groups include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl. Examples of bicyclic heteroaryl groups include quinoxalinyl, quinazolinul, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridyl, pyridopyrimidinyl, isoquinolinyl, and benzohydroxazole. All regioisomers are contemplated, e.g. 2-pyridyl, 3-pyridyl and 4-pyridyl. It will be appreciated that the polycyclic ring system includes bicyclic and tricyclic ring systems.

As used herein, the term "divalent linking moiety" refers to any divalent group capable of linking, joining, bonding or attaching two chemical moieties.

"—C(=O)—" represents a carbonyl linker group.

"—C(=O)O—" represents an ester linking group.

"—C(=O)S—" represents a thioester linking group.

"—C(=O)NH—" or "—C(=O)NR—" represents an amide linker group.

"—S(=O)$_2$—" represents a sulfone linker group.

"—S(=O)NH—" or "—S(=O)NR—" represents a sulfinamide linker group.

"—S(=O)$_2$NH—" or "—S(=O)$_2$NR—" represents a sulfonamide linker group.

"—OS(=O)$_2$—" represents a sulfonate ester linker group.

"—O—" represents an ether linker group.

"—NH—" or "—NR—" represents an amine linker group.

"—S—" represents a sulfide linker.

"—NHC(=S)NH—" or "—N(R)C(=S)N(R)—" represents a thiourea linker group.

"—NHC(=O)NH—" or "—N(R)C(=O)N(R)—" represents a urea linking group.

"—(CH$_2$)$_m$—" represents an alkylene linking group, including an alkylene bridge, having a defined number ("m") of methylene (—CH$_2$—) units.

Unless otherwise stated or structurally depicted, it will be appreciated that the orientation of the linker groups described above and herein within the compound of Formula (1) are undefined. That is, the linker groups may be attached at either side within the compound of Formula (1).

As used herein, the term "saturated" refers to a group where all available valence bonds of the backbone atoms are attached to other atoms Representative examples of saturated groups include, but are not limited to, butyl, cyclohexyl, piperidine, and the like.

As used herein, the term "unsaturated" refers to a group where at least one valence bond of two adjacent backbone atoms is not attached to other atoms. Representative examples include, but are not limited to, alkenes (e.g., —CH$_2$—CH$_2$CH=CH), phenyl, pyrrole, and the like.

As used herein, the term "optionally substituted" means that a functional group is either substituted or unsubstituted, at any available position.

As used herein, the term "substituted" refers to a group having one or more hydrogens or other atoms removed from a carbon or suitable heteroatom and replaced with a further group (i.e., substituent).

As used herein, the term "unsubstituted" refers to a group that does not have any further groups attached thereto or substituted therefore.

The present disclosure relates to compounds of Formula (1) and pharmaceutically acceptable salts thereof. Salts may be formed in the case of embodiments of the compound of Formula (1), which contain a suitable acidic or basic group. Suitable salts of the compound of Formula (1) include those formed with organic or inorganic acids or bases.

As used herein, the phrase "pharmaceutically acceptable salt" refers to pharmaceutically acceptable organic or inorganic salts. Exemplary acid addition salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Exemplary base addition salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. It will also be appreciated that non-pharmaceutically acceptable salts also fall within the scope of the present disclosure since these may be useful as intermediates in the preparation of pharmaceutically acceptable salts or may be useful during storage or transport. In one example, the compound of Formula (1) is an acetate salt.

Those skilled in the art of organic and/or medicinal chemistry will appreciate that many organic compounds can form complexes with solvents in which they are reacted or from which they are precipitated or crystallized. These complexes are known as "solvates". For example, a complex with water is known as a "hydrate". As used herein, the phrase "pharmaceutically acceptable solvate" or "solvate" refer to an association of one or more solvent molecules and a compound of the present disclosure. Examples of solvents that form pharmaceutically acceptable solvates include, but are not limited to, water, isopropanol, ethanol, methanol, DMSO, ethyl acetate, acetic acid, and ethanolamine. It will be understood that the present disclosure encompasses solvated forms, including hydrates, of the compounds of Formula (1) and salts thereof.

Those skilled in the art of organic and/or medicinal chemistry will appreciate that the compounds of Formula (1) and salts thereof may be present in amorphous form, or in a crystalline form. It will be understood that the present disclosure encompasses all forms and polymorphs of the compounds of Formula (1) and salts thereof.

As used herein, the term "stereoisomer" refers to compounds having the same molecular Formula and sequence of bonded atoms (i.e., atom connectivity), though differ in the three-dimensional orientations of their atoms in space. As used herein, the term "enantiomers" refers to two compounds that are stereoisomers in that they are non-superimposable mirror images of one another. Relevant stereocenters may be denoted with (R)- or (S)-configuration.

Compounds of Formula (1)

The present disclosure provides a compound of Formula (1), or pharmaceutically acceptable salt, solvate or stereoisomer thereof:

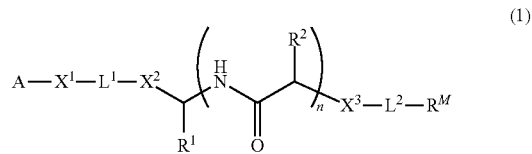

(1)

as described in any of the embodiments or examples below.

In the above Formula (1), n may 0 or 1, 2, 3 or more. For example, n may be 0, 1, 2, 3, 4, 5, 6, 7, 8, 9 or 10. In one embodiment, n may be a range provided by any of these values, including a range selected from 0 to 10, 0 to 8, 0 to 6, 0 to 5, 0 to 4, 0 to 3, 0 to 2, 1 to 10, t to 8, 1 to 6, 1 to 5, 1 to 4, 1 to 3 or 1 to 2. In one embodiment, n may be 0 to 3. In one embodiment, n may be 1 or more, for example 1, 2, 3, 4, 5, 6, 7, 8, 9 or 10. In one embodiment, n may be 1 to 3, 1 to 2, or 1. In one embodiment, n is 0. In one embodiment, n is 1. In one embodiment, n is 2. In one embodiment n is 3. When n is 0, it will be understood that there is a directed bond between the central carbon atom attached to $R^1$ and the $X^3$.

In one embodiment, n is 1 and the compound of Formula (1) has a structure of Formula (1A):

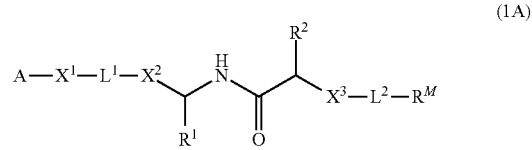

(1A)

wherein A, $L^1$, $L^2$, $X^1$, $X^2$, $X^3$, $R^1$, $R^2$ and $R^M$ are as described herein.

$X^1$ to $X^3$

In the above Formula (1), $X^1$ to $X^3$ are each independently absent or selected from the group consisting of —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O)NR$^3$—, —OS(=O)$_2$—, —N(R$^3$)C(=S)N(R$^3$)— and —N(R$^3$)C(=O)N(R$^3$)—, wherein R$^3$ is described herein. That is, $X^1$ may be absent, —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O) NR$^3$—, —OS(=O)$_2$—, —N(R$^3$)C(=S)N(R$^3$)— or —N(R$^3$)C(=O)N(R$^3$)—. Similarly, $X^2$ may be absent, —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O)NR$^3$—, —OS(=O)$_2$—, —N(R$^3$)C(=S)N(R$^3$)— or —N(R$^3$)C(=O)N(R$^3$)— $X^3$ may be absent, —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O)NR$^3$—, —OS(=O)$_2$—, —N(R$^3$)C(=S)N(R$^3$)— or —N(R$^3$)C(=O)N(R$^3$)—.

Unless otherwise stated or structurally depicted, it will be appreciated that the orientation of $X^1$, $X^2$ and $X^3$, if present, within the compound of Formula (1) are undefined. That is, $X^1$, $X^2$ and $X^3$, if present, may be attached at either side within the compound of Formula (1). For example, in the above Formula (1), when $X^2$ is —C(=O)NH— (i.e. an amide bond), the compound of Formula (1) may have a structure selected from

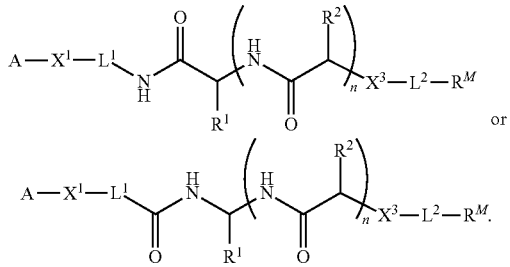

or

When $X^1$ is absent, it will be understood that that there is a direct bond between the PSMA-targeting ligand A and the rest of the molecule of Formula (1), including for example a direct bond to any one of the divalent linking moiety $L^1$, $X^2$ and the carbon attached to $R^1$. Similarly, when $X^2$ is absent, it will be understood that there is a direct bond between the carbon atom attached to $R^1$ and any one of $L^1$, $X^1$ and the PSMA-targeting ligand A, depending on whether $L^1$ and $X^1$ are present or absent. When $X^3$ is absent, it will be understood that there is a direct bond between the either the central carbon atom attached to $R^1$ or $R^2$ and the divalent linking moiety $L^2$ or $R^M$, depending on whether n is 0 or 1 or more, and whether $L^2$ is present or absent.

In one embodiment, $X^1$ and $X^2$, $X^1$ and $X^3$ or $X^2$ and $X^3$ are different (e.g. $X^1$ is —C(=O)NH— and $X^2$ is —NHC(=O)NH—). In other words, $X^1$ and $X^2$, $X^1$ and $X^3$ or $X^2$ and $X^3$ are independently selected from one and other. In an alternative embodiment, $X^1$ to $X^3$ are the same (e.g. each of $X^1$ to $X^3$ are present and are —C(=O)NH—).

In one embodiment, $X^1$ to $X^3$ are present and each independently selected from the group consisting —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)— and —N(R$^3$)C(=O)N(R$^3$)—. In one embodiment, $X^1$ to $X^3$ are each —C(=O)NR$^3$—.

In one embodiment, $X^1$ is present and selected from the group consisting of —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)— and —N(R$^3$)C(=O)N(R$^3$)—. In one embodiment, $X^1$ is —C(=O)NR$^3$—.

In one embodiment, $X^2$ is present and selected from the group consisting of —O—, —S—, —C(=O)—, —C(=O)NR$^3$—, —NR$_3$—, —C(=O)O—, —C(=O)S—, —S(=O)$_2$—, —N(R$^3$)C(=S)N(R$^3$)— and —N(R$^3$)C(=O)N(R$^3$)—. In one embodiment, $X^2$ is —C(=O)NR$^3$—.

In one embodiment, $X^3$ is present and selected from the group consisting of —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)— and —N(R$^3$)C(=O)N(R$^3$)—. In one embodiment, $X^3$ is —C(=O)NR$^3$—. In one embodiment, $X^3$ is absent or selected from the group consisting of —O—, —S—, —C(=O)—, —C(=O)NR$^3$—, —NR$^3$—, —C(=O)O—, —C(=O)S—, —S(=O)$_2$—, —S(=O)$_2$NR$^3$—, —S(=O)NR$^3$—, —OS(=O)$_2$—, —N(R$^3$)C(=S)N(R$^3$)— and —N(R$^3$)C(=O)N(R$^3$)—. In one embodiment, $X^3$ is present and selected from the group consisting of —O—, —S—, —C(=O)—, —C(=O)NH—, —NH—, —C(=O)O—, —C(=O)S—, —S(=O)$_2$—, —NHC(=S)NH—, and —NHC(=O)NH—. In one embodiment, $X^3$ is —C(=O)O— or —C(=O)NH—. In one embodiment, $X^3$ is —C(=O)NH—.

In the above Formula (1), where one or more of $X^1$ to $X^3$ are independently —C(=O)NR$^3$—, —NR$^3$—, —N(R$^3$)C(=S)N(R$^3$)— or —N(R$^3$)C(=O)N(R$^3$)—, each $R^3$ may be independently selected from the group consisting of H, alkyl, alkenyl, alkynyl, carbocyclyl, heterocyclyl, alkylcarbocyclyl, alkylheterocyclyl, each of which is optionally substituted. In one embodiment, where one or more of $X^1$ to $X^3$ are independently —C(=O)NR$^3$—, —NR$^3$—, —N(R$^3$)C(=S)N(R$^3$)— or —N(R$^3$)C(=O)N(R$^3$)—, each $R^3$ may be independently selected from the group consisting of H and $C_{1-10}$ alkyl. In one embodiment, where one or more of $X^1$ to $X^3$ are independently —C(=O)NR$^3$—, —NR$^3$—, —N(R$^3$)C(=S)N(R$^3$)— or —N(R$^3$)C(=O)N(R$^3$)—, each $R^3$ is H.

In one embodiment, $X^1$ to $X^3$ are present and each independently selected from the group consisting of —O—, —S—, —C(=O)—, —C(=O)NH—, —NH—, —C(=O)O—, —C(=O)S—, —S(=O)$_2$—, —NHC(=S)NH—, and —NHC(=O)NH—. In one embodiment, $X^1$ to $X^3$ are present and are each —C(=O)NH—.

In one embodiment, $X^1$ is selected from the group consisting of —O—, —S—, —C(=O)—C(=O)NH—, —NH—, —C(=O)O—, —C(=O)S—, —S(=O)$_2$—, —NHC(=S)NH—, and —NHC(=O)NH—. In one embodiment, $X^1$ is —C(=O)NH—.

In one embodiment, $X^2$ is selected from the group consisting of —O—, —S—, —C(=O)—, —C(=O)NH—, —NH—, —C(=O)O—, —C(=O)S—, —S(=O)$_2$—, —NHC(=S)NH—, and —NHC(=O)NH—. In one embodiment, $X^2$ is —C(=O)NH—.

In one embodiment, $X^2$ is selected from the group consisting of —O—, —S—, —C(=O)—C(=O)NH—, —NH—, —C(=O)O—, —C(=O)S—, —S(=O)$_2$—, —NHC(=S)NH—, and —NHC(=O)NH—. In one embodiment, $X^3$ is —C(=O)NH—.

In one embodiment, $X^1$ to $X^3$ are each —C(=O)NR$^3$—, and the compound of Formula (1) has a structure of Formula (IB):

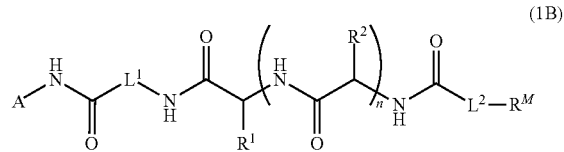

wherein n, A, $L^1$, $L^2$, $R^1$, $R^2$ and $R^M$ are as described herein.

$L^1$ and $L^2$

In the above Formula (1), $L^1$ and $L^2$ represent linker moieties and are each independently absent or a divalent linking moiety. That is, $L^1$ may be absent or a divalent linking moiety. Unless otherwise stated or structurally depicted, it will be appreciated that the orientation of $L^1$ and $L^2$, if present, within the compound of Formula (1) are undefined. That is, $L^1$ and $L^2$, if present, may be attached at either side within the compound of Formula (1). When $L^1$ is absent, it will be understood that there is a direct bond between $X^2$ and any one of the carbon atom attached to $R^1$, $X^1$ and the PSMA targeting ligand A, depending on whether $X^1$ and $X^2$ are present or absent. Similarly, when $L^2$ is absent, it will be understood that there is a direct bond between $R^M$ and any one of $X^3$, the carbon atom attached to $R^2$ (where multiple carbons attached to $R^2$ exist [viz., where n is 2 or 3], the bond is to the carbon atom attached to $R^2$ that is the furthest from the carbon atom attached to $R^1$), and the carbon atom attached to $R^1$, depending on whether $X^3$ is present or absent and n is 0, 1, 2 or 3 etc.).

In one embodiment, $L^1$ and $L^2$ are different (e.g. $L^1$ is —$C_{1-20}$alkyl- which is interrupted with one or more groups selected from —O—, —S—, —C(=O)—, —C(=O)NH—, —NH—, —C(=O)O—, —C(=O)S—, —S(=O)$_2$—, —NHC(=S)NH—, and —NHC(=O)NH and $L^2$ is —$C_{1-10}$alkyl-, wherein each $C_{1-20}$alkyl and $C_{1-10}$alkyl is optionally substituted).

In one embodiment, $L^1$ and $L^2$ are each independently an aliphatic linker group which is uninterrupted or interrupted and is optionally substituted. As used herein, the term "aliphatic linker group" refers to a divalent linking moiety in which the atoms forming the linking moiety are connected by single, double or triple bonds to form a non-aromatic linking moiety (e.g. does not comprise any aromatic ring structure within the backbone of the linking moiety). In one embodiment, $L^1$ is present and is —$C_{1-30}$alkyl-, which is uninterrupted or interrupted and optionally substituted. In one embodiment, $L^1$ is —$C_{1-20}$alkyl- which is uninterrupted or interrupted and optionally substituted.

In one embodiment, $L^2$ is absent or is an aliphatic linker group which is uninterrupted or interrupted and optionally substituted. In one embodiment, $L^2$ is an aliphatic linker group which is uninterrupted or interrupted and optionally substituted. In one embodiment, $L^2$ is absent or is an aliphatic linker group which is uninterrupted or interrupted with one or more groups selected from —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)—, and —N(R$^3$)C(=O)N(R$^3$)—. In one embodiment, $L^2$ is present and is —$C_{1-20}$alkyl-, which is uninterrupted or interrupted and optionally substituted. In one embodiment, $L^2$ is —$C_{1-10}$alkyl- which is uninterrupted or interrupted and optionally substituted.

When present in either $L^1$ and/or $L^2$, each $C_{1-30}$alkyl, $C_{1-20}$alkyl or $C_{1-10}$alkyl may be uninterrupted or interrupted and optionally substituted. In one embodiment, each $C_{1-30}$alkyl, $C_{1-20}$alkyl or $C_{1-10}$alkyl may be uninterrupted or interrupted with one or more groups selected from —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)—, and —N(R$^3$)C(=O)N(R$^3$)—, and optionally substituted. In one embodiment, each $C_{1-30}$alkyl, $C_{1-20}$alkyl or $C_{1-10}$alkyl may be uninterrupted or interrupted with one or more groups selected from —O—, —S—, —C(=O)—, —C(=O)NH—, —NH—, —C(=O)O—, —C(=O)S—, —S(=O)$_2$—, —NHC(=S)NH—, and —NHC(=O)NH—, and optionally substituted. In one embodiment, each $C_{1-30}$alkyl, $C_{1-20}$alkyl or $C_{1-10}$alkyl may be interrupted with a total of 1 to 10, 1 to 5, or preferably 1 to 3 groups, each interruption independently selected from —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)—, and —N(R$^3$)C(=O)N(R$^3$)—, and optionally substituted.

In one embodiment, $L^1$ is —$C_{1-20}$alkyl- which is uninterrupted or interrupted with one or more groups selected from —O—, —S—, —C(=O)—, —C(=O)NH—, —NH—, —C(=O)O—, —C(=O)S—, —S(=O)$_2$—, —NHC(=S)NH—, and —NHC(=O)NH, and is optionally substituted. In one embodiment, $L^2$ is —$C_{1-10}$alkyl- or —$C_{2-10}$alkyl- and is optionally substituted. In one embodiment, $L^2$ is —$C_{2-10}$alkyl- and is optionally substituted. In one embodiment, $L^2$ is —$C_{1-10}$alkyl- and optionally substituted. In one embodiment, $L^1$ is —$C_{1-20}$alkyl- which is interrupted with one or more —C(=O)NR$^3$— (e.g. —C(=O)NH—) amide bonds, wherein the $C_{1-20}$alkyl is optionally substituted with one or more $R^8$. In one embodiment, $L^1$ comprises a total of 1 to 5, preferably 1 to 3, more preferably 1 to 2 —C(=O)NR$^3$— (e.g. —C(=O)NH—) amide bond interruptions within its backbone, and optionally substituted.

In one embodiment, $L^1$ and $L^2$ may be each optionally substituted. In one embodiment, $L^1$ and $L^2$ may be each optionally substituted with one or more $R^8$. In one embodiment, $L^2$ is optionally substituted with one or more $R^8$. In one embodiment, $L^2$ is —$C_{1-10}$alkyl- or —$C_{2-10}$alkyl- and is optionally substituted with one or more $R^1$. In one embodiment, $L^2$ is —$C_{2-10}$alkyl- and is optionally substituted with one or more $R^8$. In one embodiment, $L^2$ is —$C_{1-10}$alkyl- and optionally substituted with one or more $R^1$. In the instance where $L^1$ or $L^2$ is not substituted with one or more $R^1$, then it will be understood that a hydrogen atom will remain as the substitution.

In one embodiment, $L^2$ is optionally substituted with one or more groups selected from $C_{1-10}$alkyl, $OC_{1-10}$alkyl, —NH$_2$, —OH, —COOH, and —C(=O)OC$_{1-6}$alkyl. In one embodiment, $L^2$ is optionally substituted with one or more groups selected from $C_{2-10}$alkyl, $OC_{1-10}$alkyl, —NH$_2$, —OH, —COOH, and —C(=O)OC$_{1-6}$alkyl. In one embodiment, $L^2$ is optionally substituted with one or more groups selected from $C_{1-10}$alkyl, $C_{2-10}$alkyl, $OC_{1-10}$alkyl, —NH$_2$, —OH, —COOH, and —C(=O)OC$_{1-6}$alkyl.

In one embodiment, $L^2$ comprises a chiral center. In one embodiment, $L^2$ is —$C_{1-20}$alkyl- or —$C_{1-10}$alkyl-, substituted with one or more $R^8$, wherein at least one carbon attached to $R^8$ forms a chiral center. In one embodiment, $L^2$ is —$C_{1-10}$alkyl-, substituted with one or more $R^8$, wherein at least one carbon attached to $R^8$ forms a chiral center. A person skilled in the art will understand that "chiral center" refers to a tetravalent carbon atom with 4 different substituting groups, or 3 different substituting groups and a hydrogen, thereto. Without intending to limit the scope of any of the aspects, embodiments, or examples described herein, it is believed that the existence of chiral center within $L^2$, may contribute to the PSMA affinity of compounds of Formula (1).

In one embodiment, $L^2$ is —$C_{1-20}$alkyl- or —$C_{1-10}$alkyl-, substituted with one or more $R^1$. In one embodiment, $L^2$ is —$C_{1-20}$alkyl- or —$C_{1-10}$alkyl-, substituted with one or more groups selected from $C_{1-10}$alkyl, $OC_{1-10}$alkyl, —NH$_2$, —OH, —COOH, and —C(=O)OC$_{1-6}$alkyl. In one embodiment, $L^2$ is —$C_{1-20}$alkyl- or —$C_{1-10}$alkyl-, substituted with one or more groups selected from $C_{1-10}$alkyl, $OC_{1-10}$alkyl, —NH$_2$, —OH, —COOH, and —C(=O)OC$_{1-6}$alkyl. In one embodiment, $L^2$ is —$C_{1-20}$alkyl- or —$C_{1-10}$alkyl-, substituted with one or more groups selected from $C_{1-10}$alkyl, $OC_{1-10}$alkyl, —NH$_2$, —OH, —COOH, and —C(=O)OC$_{1-6}$alkyl.

In one embodiment, $L^2$ is —$C_{1-10}$alkyl-, substituted with one or more $R^1$. In one embodiment, $L^2$ is —$C_{1-10}$alkyl-, substituted with one or more groups selected from $C_{1-10}$alkyl, $OC_{1-10}$alkyl, —NH$_2$, —OH, —COOH, and —C(=O)OC$_{1-6}$alkyl. In one embodiment, $L^2$ is —$C_{1-10}$alkyl-, substituted with one or more groups selected from $C_{1-10}$alkyl, $OC_{1-10}$alkyl, —NH$_2$, —OH, —COOH, and —C(=O)OC$_{1-6}$alkyl. In one embodiment, $L^2$ is or —$C_{1-10}$alkyl-, substituted with one or more groups selected from $C_{1-10}$alkyl, $OC_{1-10}$alkyl, —NH$_2$, —OH, —COOH, and —C(=O)OC$_{1-6}$alkyl.

In line with the above, in a preferred embodiment the moiety —$X^1$-$L^1$-$X^2$— in Formula (1) has a structure (L-1):

—NHC(=O)—$R^{19}$—C(=O)NH—$R^{20}$—CH(COOH)—NH—C(=O)—* (L-1)

wherein * indicates the bond which is attached to the carbon atom carrying $R^1$ in Formula (1).

In line with the above, in a preferred embodiment the moiety —$X^3$-$L^2$- in Formula (1) has the structure (L-2) or (L-3):

—NHC(=O)—$R^{19}$—CH(COOH)—* (L-2)

—NHC(=O)—$R^{19}$—* (L-3)

wherein * indicates the bond which is attached to $R^M$ in Formula (1).

In some embodiments, $R^{19}$ and $R^{20}$ are each independently selected from an optionally substituted $C_{1-20}$alkyl. In some embodiments, $R^{19}$ and $R^{20}$ are each independently selected from an optionally substituted $C_{1-10}$alkyl. In some embodiments, each of $R^{19}$ and $R^{20}$ may be independently optionally substituted with one or more $R^1$. In one embodiment, $R^{19}$ and $R^{20}$ are unsubstituted. In the instance where $R^{19}$ or $R^{20}$ is not substituted with one or more $R^8$, then it will be understood that one or more hydrogen atoms will remain at the unsubstituted positions.

In one embodiment, the moiety —$X^3$-$L^2$- in Formula (1L) has the structure (L-2) or (L-3):

—NHC(=O)—$R^{19}$—CH(COOH)—* (L-2)

—NHC(=O)—$R^{19}$—* (L-3)

wherein * indicates the bond which is attached to the cyclic N in Formula (1L).

In some embodiments, $R^{19}$ is $C_{1-20}$alkyl. In some embodiments, $R^{19}$ is $C_{1-10}$alkyl.

In some embodiments, $R^{19}$ is $C_{2-20}$alkyl. In some embodiments, $R^{19}$ is $C_{2-10}$alkyl. In some embodiments, $R^{19}$ is $C_{1-10}$alkyl or $C_{2-10}$alkyl. In some embodiments, $R^{19}$ may be optionally substituted with one or more $R^8$. In one embodiment, $R^{19}$ is unsubstituted. In the instance where $R^{19}$ is not substituted with one or more $R^1$, then it will be understood that one or more hydrogen atoms will remain at the unsubstituted positions.

In one embodiment, the moiety —$X^3$-$L^2$- in Formula (1L) has the structure (L-2) or (L-3), wherein the carbon atom that is attached to the cyclic N in Formula (1L) is a chiral center. Without intending to limit the scope of any of the aspects, embodiments, or examples described herein, it is believed that the existence of chiral center at the carbon atom that is attached to the cyclic N, may contribute to the PSMA affinity of compounds of Formula (1).

In line with the above, in one embodiment, the moiety —$X^3$-$L^2$- in Formula (1L) has the structure (L-2):

—NHC(=O)—$R^{19}$—CH(COOH)—* (L-2).

$R^1$ and $R^2$

Without intending to limit the scope of any of the aspects, embodiments or examples described herein, it is believed that $R^1$ and/or $R^2$ may influence the binding affinity of compounds of Formula (1) to PSMA, through aromatic stacking interaction(s) with an arene-binding site on PSMA. In the above Formula (1), $R^1$ and each $R^2$ are independently selected from the group consisting of an aryl, alkylaryl, heteroaryl and alkylheteroaryl, each of which is optionally substituted. That is, $R^1$ may be selected from the group consisting of an aryl, alkylaryl, heteroaryl and alkylheteroaryl, each of which is optionally substituted. Similarly, $R^2$ may be selected from the group consisting of an aryl, alkylaryl, heteroaryl and alkylheteroaryl, each of which is optionally substituted. $R^1$ and $R^2$ may be the same (e.g. $R^1$ and $R^2$ are both an optionally substituted alkylaryl) or $R^1$ and $R^2$ may be different (e.g. $R^1$ is an alkylaryl and $R^2$ is an alkylaryl substituted with one or more $R^8$). In other words, the $R^1$ and $R^2$ substituents are independently selected from one another). In one embodiment, $R^1$ and $R^2$ are each independently an optionally substituted alkylaryl or an optionally substituted alkylheteroaryl. In one embodiment, $R^1$ and $R^2$ are each independently an optionally substituted alkylaryl. In one embodiment, $R^1$ is an optionally substituted alkylaryl. In one embodiment, $R^1$ is an optionally substituted alkylheteroaryl. In one embodiment, $R^2$ is an optionally substituted alkylaryl. In one embodiment, $R^2$ is an optionally substituted alkylheteroaryl. In one embodiment, $R^1$ and each $R^2$ are independently selected from the group consisting of aryl, alkylaryl, heteroaryl and alkylheteroaryl. That is, $R^1$ may be selected from the group consisting of an aryl, alkylaryl, heteroaryl and alkylheteroaryl. Similarly, $R^2$ may be selected from the group consisting of an aryl, alkylaryl, heteroaryl and alkylheteroaryl. In one embodiment, $R^1$ and $R^2$ are each independently selected from an optionally substituted 3-10-membered aryl, an optionally substituted $C_{1-10}$alkyl-3-10-membered aryl, an optionally substituted 3-10-membered heteroaryl, or an optionally substituted $C_{1-10}$alkyl-3-10-membered heteroaryl. That is, $R^1$ may be selected from an optionally substituted 3-10-membered aryl, an optionally substituted $C_{1-10}$alkyl-3-10-membered aryl, an optionally substituted 3-10-membered heteroaryl, or an optionally substituted $C_{1-10}$alkyl-3-10-membered heteroaryl. Similarly, $R^2$ may be selected from an optionally substituted 3-10-membered aryl, an optionally substituted $C_{1-10}$alkyl-3-10-membered aryl, an optionally substituted 3-10-membered heteroaryl, or an optionally substituted $C_{1-10}$alkyl-3-10-membered heteroaryl. In one embodiment, $R^1$ is an optionally substituted 3-10-membered aryl. In one embodiment, $R^1$ is an optionally substituted $C_{1-10}$alkyl-3-10-membered aryl. In one embodiment, $R^1$ is an optionally substituted 3-10-membered heteroaryl. In one embodiment, $R^1$ is an optionally substituted $C_{1-10}$alkyl-3-10-membered heteroaryl. In one embodiment, $R^2$ is an optionally substituted 3-10-membered aryl. In one embodiment, $R^2$ is an optionally substituted $C_{1-10}$alkyl-3-10-membered aryl. In one embodiment, $R^2$ is an optionally substituted 3-10-membered heteroaryl. In one embodiment, $R^2$ is an optionally substituted $C_{1-10}$alkyl-3-10-membered heteroaryl. The heteroaryl or the heteroaryl group of the alkylheteroaryl may selected from the group consisting of pyridyl, pyrimidinyl furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl, each of which is optionally substituted.

In one embodiment, $R^1$ and $R^2$ are each independently an optionally substituted aryl or an optionally substituted alkylaryl. Preferably, the alkylaryl comprises one aryl group bound to an alkyl group, each of which may be optionally substituted. In one embodiment, The aryl or the aryl group of the alkylaryl may be independently selected from phenyl and napthyl, such as 2-naphthyl. The alkyl group of the alkylaryl may be a $C_{1-10}$alkylene group, $C_{1-6}$alkylene group, or preferable a —$CH_2$—. In one embodiment, $R^1$ and $R^2$ are each independently an optionally substituted aryl, an optionally substituted benzyl or an optionally substituted —$CH_2$-naphthyl. In one embodiment, $R^1$ and $R^2$ are each independently an optionally substituted benzyl. In one embodiment, $R^1$ and $R^2$ are benzyl, each independently optionally substituted with one or more groups selected from halogen, —NO$_2$, —NH$_2$, —CN, —SCN, —COOH and —OH. In one embodiment, R$^1$ is benzyl, and R$^2$ is benzyl substituted with one or more groups selected from halogen, —NO$_2$, —NH$_2$, —CN, —SCN, —COOH and —OH. In one embodiment, R$^1$ is benzyl and is unsubstituted, and R$^2$ is benzyl substituted with one or more groups selected from halogen, —NO$_2$, —NH$_2$, —CN, —SCN, —COOH and —OH.

In one embodiment, R$^1$ and R$^2$ are each independently an optionally substituted benzyl, the compound of Formula (1) has a structure of Formula (1C):

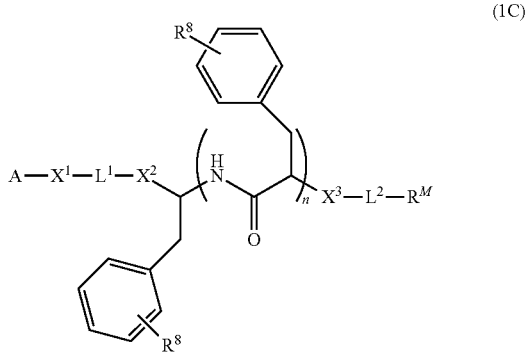

(1C)

wherein n, A, L$^1$, L$^2$, X$^1$, X$^2$, X$^3$, and R$^M$ are as described herein.

In the above Formula (1), each of R$^1$ and R$^2$ may be optionally substituted. In one embodiment, each of R$^1$ and R$^2$ may be optionally substituted with one or more R$^8$. In one embodiment, R$^1$ and R$^2$ are each independently optionally substituted with one or more groups selected from halogen, C$_{1-10}$alkyl, OC$_{1-10}$alkyl, C$_{1-10}$haloalkyl, OC$_{1-10}$haloalkyl, C$_{2-10}$alkenyl, C$_{2-10}$alkynyl, OC$_{2-10}$alkenyl, OC$_{2-10}$alkynyl, —NO$_2$, —N(R$^{11}$)$_2$, —CN, —SCN, —N$_3$, =O, —C(=O)R$^{11}$, —C(=O)OR$^{11}$, —N(R$^{11}$)C(=O)R$^{11}$, and —OR$^{11}$, wherein each R$^{11}$ is independently as described herein. In the instance where R$^1$ or R$^2$ is not substituted with one or more R$^1$, then it will be understood that a hydrogen atom will remain as the substitution.

R$^3$

In the above Formula (1), each R$^3$ may be independently selected from the group consisting of H, alkyl, alkenyl, alkynyl, carbocyclyl, heterocyclyl, alkylcarbocyclyl, and alkylheterocyclyl, each of which is optionally substituted.

In one embodiment, where one or more of X$^1$ to X$^3$ described herein are independently —C(=O)NR$^3$—, —NR$^3$—, —N(R$^3$)C(=S)N(R$^3$)— or —N(R$^3$)C(=O)N(R$^3$)—, each R$^3$ may be independently selected from the group consisting of H, alkyl, alkenyl, alkynyl, carbocyclyl, heterocyclyl, alkylcarbocyclyl, alkylheterocyclyl, each of which is optionally substituted.

In one embodiment, where R$^4$ to R$^7$ described herein are each independently selected from the group consisting of —C$_{1-10}$alkylC(=O)N(R$^3$)$_2$, —C$_{1-10}$alkylP(=O)(OR$^3$)$_2$, —C$_{1-10}$alkylP(=O)OR$^3$(R$^3$) and —C$_{1-10}$alkylP(=O)(R$^3$)$_2$, each R$^3$ may be independently selected from the group consisting of H, alkyl, alkenyl, alkynyl, carbocyclyl, heterocyclyl, alkylcarbocyclyl, alkylheterocyclyl, each of which is optionally substituted.

In one embodiment, where L$^1$ and/or L$^2$ described herein comprise an optionally substituted C$_{1-30}$alkyl, optionally substituted C$_{1-20}$alkyl or optionally substituted C$_{1-10}$alkyl, wherein each C$_{1-30}$alkyl, C$_{1-20}$alkyl or C$_{1-10}$alkyl may be uninterrupted or interrupted with one or more groups selected from —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)—, and —N(R$^3$)C(=O)N(R$^3$)—, each R$^3$ may be independently selected from the group consisting of H, alkyl, alkenyl, alkynyl, carbocyclyl, heterocyclyl, alkylcarbocyclyl, alkylheterocyclyl, each of which is optionally substituted.

In the above Formula (1), each R$^3$ may be optionally substituted. In one embodiment, each of R$^3$ may be optionally substituted with one or more R$^8$. In the instance where R$^3$ is not substituted with one or more R$^8$, then it will be understood that a hydrogen atom will remain as the substitution.

R$^M$

In the above Formula (1), R$^M$ is a chelating moiety. In some embodiments, R$^M$ is optionally complexed to a radioisotope described herein. In some embodiments, R$^M$ is complexed to a radioisotope described herein. In some embodiments, the compound of Formula (1) is optionally complexed to a radioisotope described herein. For the most part, it will be appreciated that any such complexation occurs predominantly at the chelator moiety of the compound of Formula (1), such as a tetraazamacrocyclic moiety, as described herein. Any disclosure herein that "R$^M$ is optionally complexed to a radioisotope" should be understood to also disclose that the compound of Formula (1) is optionally complexed to that radioisotope. Likewise, any disclosure herein that "R$^M$ is complexed to a radioisotope" should be understood to also disclose that the compound of Formula (1) is complexed to that radioisotope. R$^M$ may be any suitable chelating moiety that is capable of complexing with a radioisotope. In one embodiment, R$^M$ is a macrocyclic moiety. R$^M$ is a tetraazamacrocyclic moiety. In one embodiment, R$^M$ is chelating moiety having the structure of Formula (M-1):

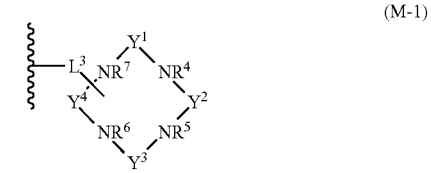

(M-1)

wherein ⌇ represents the bond which attaches R$^M$ to the rest of the molecule of Formula (1).

In some embodiments, L$^3$ is absent and the ring is directly connected to the rest of the molecule of Formula (1) via any ring heteroatom (e.g. at any nitrogen atom of M-1) or any one of Y$^1$ to Y$^4$, or L$^3$, or L$^3$ is a divalent linking moiety connecting the ring to the rest of the molecule of Formula (1) via any ring heteroatom or any one of Y$^1$ to Y$^4$. In some embodiments, L$^3$ is absent and the ring is directly connected to the rest of the molecule of Formula (1) via any ring heteroatom (e.g. at any nitrogen atom of M-1) or any one of Y$^1$ to Y$^4$. It will be appreciated that when L$^3$ is absent the rest of the molecule of Formula (1) is connected at any nitrogen atom of M-1, the corresponding R group at that nitrogen atom (e.g. either one of R$^4$ to R$^7$) will be absent. In some embodiments, L$^3$ is a divalent linking moiety connecting the ring to the rest of the molecule of Formula (1) via any ring heteroatom (e.g. at any nitrogen atom of M-1) or any one of Y$^1$ to Y$^4$. It will be appreciated that when L$^3$ is present and connecting the ring to the rest of the molecule of Formula (1)

at any nitrogen atom of M-1, the corresponding R group at that nitrogen atom (e.g. either one of $R^4$ to $R^7$) will be absent.

It will be appreciated that for compounds of Formula (1), there will always be a bond from the ring (e.g. the macrocyclic chelator) to any one of $L^3$, $L^2$, $X^3$, the carbon atom attached to $R^2$ (where multiple carbons attached to $R^2$ exist [viz., where n is 2 or 3], the bond is to the carbon atom attached to $R^2$ that is the furthest from the carbon atom attached to $R^1$), and the carbon atom attached to $R^1$. The person skilled in the art will understand that in some embodiments, each of $L^3$, $L^2$, $X^3$, and the carbon atom attached to $R^2$, may independently be absent or present, and that in consequence, the atom to which the ring is attached may be an atom of or defined by $L^3$, $L^2$, $X^3$, or the carbon atom attached to $R^2$, or the carbon atom attached to $R^1$, as the case may be.

More generally, it will be understood that some embodiments permit multiple permutations of absent/present groups (e.g. $X^1$, $X^2$, $X^3$, $L^1$, $L^2$ or $L^3$), and that in such cases a given group will be linked (where relevant) via a covalent bond to the nearest present group, according to the order defined by the relevant structural formulae (e.g. the structure of Formula (1), any one of Formulas (1A) to (1L), and any other structure described herein). This will be clear to the person skilled in the art, and for ease of reference where there are multiple possibilities for attachment depending on group/variable selection, the term 'the rest of the molecule' has been adopted in accordance with the above explanation. In one embodiment, $R^M$ is a chelating moiety having the structure of formula (M-2):

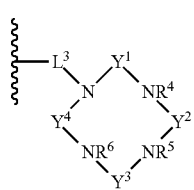

(M-2)

In one embodiment, $L^3$ is absent or —$C_{1-20}$alkyl- which is uninterrupted or interrupted and optionally substituted. In one embodiment, $L^3$ is absent or —$C_{1-10}$alkyl-which is uninterrupted or interrupted and optionally substituted. When present in $L^3$, each $C_{1-20}$alkyl or $C_{1-10}$alkyl may be uninterrupted or interrupted and optionally substituted. In one embodiment, each $C_{1-20}$alkyl or $C_{1-10}$alkyl may be uninterrupted or interrupted with one or more groups selected from —O—, —S—, —C(=O)—, —C(=O)NR³—, —NR³—, —C(=O)O—, —C(=O)S—, —S(=O)$_2$—, —N(R³)C(=S)N(R³)—, and —N(R³)C(=O)N(R³)—, and optionally substituted. In one embodiment, each $C_{1-20}$alkyl or $C_{1-10}$alkyl may be uninterrupted or interrupted with one or more groups selected from —O—, —S—, —C(=O)—, —C(=O)NH—, —NH—, —C(=O)O—, —C(=O)S—, —S(=O)$_2$—, —NHC(=S)NH—, and —NHC(=O)NH—, and optionally substituted. In one embodiment, each $C_{1-20}$alkyl or $C_{1-10}$alkyl is uninterrupted and optionally substituted. In one embodiment, $L^3$ may be optionally substituted. In one embodiment, $L^3$ may be optionally substituted with one or more $R^1$. In the instance where $L^3$ is not substituted with one or more $R^8$, then it will be understood that a hydrogen atom will remain as the substitution.

In some embodiments, $Y^1$ to $Y^4$ are each independently an optionally substituted —$C_{1-6}$alkyl-. In some embodiments, $Y^1$ to $Y^4$ are each independently selected from an optionally substituted —$C_{2-6}$alkyl-. In some embodiments, $Y^1$ to $Y^4$ are each independently selected from an optionally substituted —$C_{2-4}$alkyl-. In some embodiments, $Y^1$ to $Y^4$ are each independently selected from an optionally substituted —$C_{2-3}$alkyl-. Each alkyl of $Y^1$ to $Y^4$ may be optionally substituted. In one embodiment, each alkyl of $Y^1$ to $Y^4$ may be optionally substituted with one or more $R^8$. In the instance where $Y^1$ to $Y^4$ is not substituted with one or more $R^8$, then it will be understood that a hydrogen atom will remain as the substitution.

In some embodiments, $R^4$ to $R^7$ are each independently selected from the group consisting of —C(=O)N($R^3$)$_2$, —P(=O)(OR³)$_2$, —P(=O)OR³($R^3$), —P(=O)($R^3$)$_2$, —$C_{1-10}$alkylC(=O)N($R^3$)$_2$, —$C_{1-10}$alkylP(=O)(OR³)$_2$, —$C_{1-10}$alkylP(=O)OR³($R^3$) and —$C_{1-10}$alkylP(=O)($R^3$)$_2$, or one of $R^4$ and $R^6$ or $R^5$ and $R^7$ together from a —(CH$_2$)$_m$— bridge; wherein each $C_{1-10}$alkyl is optionally substituted, or $R^4$ to $R^7$ is a bond connecting the ring to $L^3$ or the rest of the molecule of Formula (1), and m is 1 to 3, preferably 2.

In some embodiments, $R^4$ to $R^7$ are each independently selected from the group consisting of —C(=O)N($R^{14}$)$_2$, —P(=O)(OR$^{14}$)$_2$, —P(=O)OR³($R^{14}$), —P(=O)($R^{14}$)$_2$, —$C_{1-10}$alkylC(=O)N($R^{14}$)$_2$, —$C_{1-10}$alkylP(=O)(OR$^{14}$)$_2$, —$C_{1-10}$alkylP(=O)OR$^{14}$($R^{14}$) and —$C_{1-10}$alkylP(=O)($R^{14}$)$_2$, or one of $R^4$ and $R^6$ or $R^5$ and $R^7$ together from a —(CH$_2$)$_m$— bridge; wherein each $C_{1-6}$alkyl is optionally substituted, or $R^4$ to $R^7$ is a bond connecting the ring to $L^3$ or the rest of the molecule of Formula (1), and m is 1 to 3, preferably 2.

In some embodiments, $R^4$ to $R^7$ are each independently selected from the group consisting of —C(=O)NH$_2$, —P(=O)(OH)$_2$, —P(=O)(OH)H, —P(=O)(OH)OC$_{1-6}$alkyl, —$C_{1-6}$alkylC(=O)NH$_2$, —$C_{1-6}$alkylP(=O)(OH)$_2$, —$C_{1-6}$alkyl-P(=O)(OH)H, and —$C_{1-6}$alkyl-P(=O)(OH)OC$_{1-6}$alkyl, or one of $R^4$ and $R^6$ or $R^5$ and $R^7$ together from a —(CH$_2$)$_m$— bridge; wherein each $C_{1-6}$alkyl is optionally substituted, or $R^4$ to $R^7$ is a bond connecting the ring to $L^3$ or the rest of the molecule of Formula (1), and m is 1 to 3, preferably 2.

In some embodiments, $R^4$ to $R^7$ are each independently selected from the group consisting of —C(=O)N($R^{14}$)$_2$ and —$C_{1-10}$alkylC(=O)N($R^{14}$)$_2$, or one of $R^4$ and $R^6$ or $R^5$ and $R^7$ together from a —(CH$_2$)$_m$— bridge, or $R^4$ to $R^7$ is a bond connecting the ring to $L^3$ or the rest of the molecule of Formula (1); wherein m is 1 to 3, preferably 2.

In some embodiments, $R^4$ to $R^7$ are each independently selected from the group consisting of —C(=O)NH$_2$, and —$C_{1-6}$alkyl-C(=O)NH$_2$, or one of $R^4$ and $R^6$ or $R^5$ and $R^7$ together from a —(CH$_2$)$_m$— bridge, or $R^4$ to $R^7$ is a bond connecting the ring to $L^3$ or the rest of the molecule of Formula (1); wherein m is 1 to 3, preferably 2. In some embodiments, each $R^4$ to $R^7$ may be optionally substituted. In some embodiments, each $R^4$ to $R^7$ may be optionally substituted with one or more $R^8$. In the instance where $R^4$ to $R^7$ is not substituted with one or more $R^8$, then it will be understood that a hydrogen atom will remain as the substitution.

In some embodiments, $R^M$ is a chelating moiety having a structure selected from the group consisting of Formula (M-1A) to (M-1D):

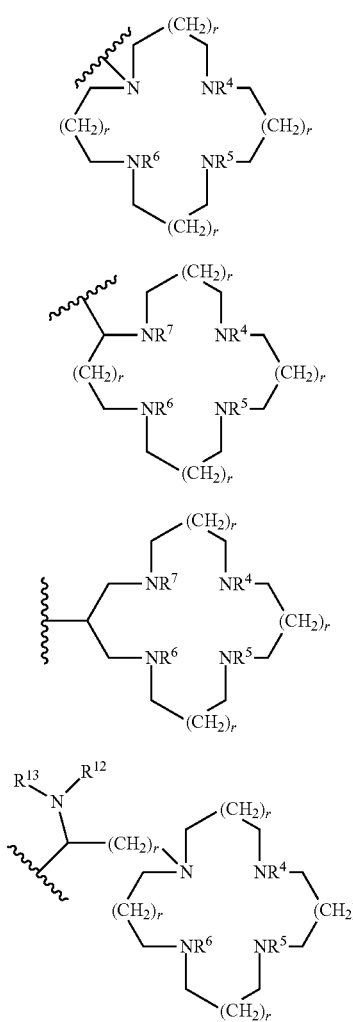

(M-1A)

(M-1B)

(M-1C)

(M-1D)

wherein ⌇ represents the bond which attaches $R^M$ to the rest of the molecule of in Formula (1); r is 0 or 1, and $R^4$ to $R^7$ are described herein.

In some embodiments, $R^{12}$ and $R^{13}$ are each independently selected from the group consisting of H, —C(=O)OR$^{14}$, —C(=O)N(R$^{14}$)$_2$, —C$_{1-6}$alkylC(=O)OR$^{14}$, and —C$_{1-6}$alkylC(=O)N(R$^{14}$)$_2$, —P(=O)(OR$^{14}$)$_2$—P(=O)OR$^{14}$(R$^{14}$), —P(=O)(R$^{14}$)$_2$, —C$_{1-6}$alkylP(=O)OR$^{14}$(R$^{14}$) and —C$_{1-6}$alkylP(=O)(R$^{14}$)$_2$, wherein each C$_{1-6}$alkyl is optionally substituted, or $R^{12}$ and $R^{13}$ together form an optionally substituted heterocyclyl. In some embodiments, $R^{12}$ and $R^{13}$ are each independently selected from the group consisting of H, —C(=O)OR$^{14}$, —C(=O)N(R$^{14}$)$_2$, —C$_{1-6}$alkylC(=O)OR$^{14}$, and —C$_{1-6}$alkylC(=O)N(R$^{14}$)$_2$ wherein each C$_{1-6}$alkyl is optionally substituted, or $R^{12}$ and $R^{13}$ together form an optionally substituted heterocyclyl. In some embodiments, $R^{12}$ and $R^{13}$ are each independently —C(=O)OH or —C(=O)NH$_2$.

In the above Formula (1), each C$_{1-6}$alkyl of $R^{12}$ or $R^{13}$ may be optionally substituted. In one embodiment, each C$_{1-6}$alkyl of $R^{12}$ or $R^{13}$ may be optionally substituted with one or more $R^8$. In the instance where the C$_{1-6}$alkyl of $R^{12}$ or $R^{13}$ is not substituted with one or more $R^8$, then it will be understood that a hydrogen atom will remain as the substitution.

In some embodiments, each $R^{14}$ is independently selected from the group consisting of H, C$_{1-10}$alkyl, C$_{2-10}$alkenyl, C$_{2-10}$alkynyl, 3-10 membered carbocyclyl, 3-10 membered heterocyclyl, C$_{1-10}$alkyl-3-10-membered carbocyclyl, C$_{1-10}$alkyl-3-10-membered heterocyclyl, wherein each alkyl, alkenyl, alkynyl carbocyclyl, and heterocyclyl is optionally substituted, for example with one or more $R^8$. In the instance where $R^{14}$ is not substituted with one or more $R^1$, it will be understood that a hydrogen atom will remain as the substitution.

In some embodiments, $R^M$ is a chelating moiety, having a structure selected from the group consisting of Formula (M-1Ai) to (M-1Dii):

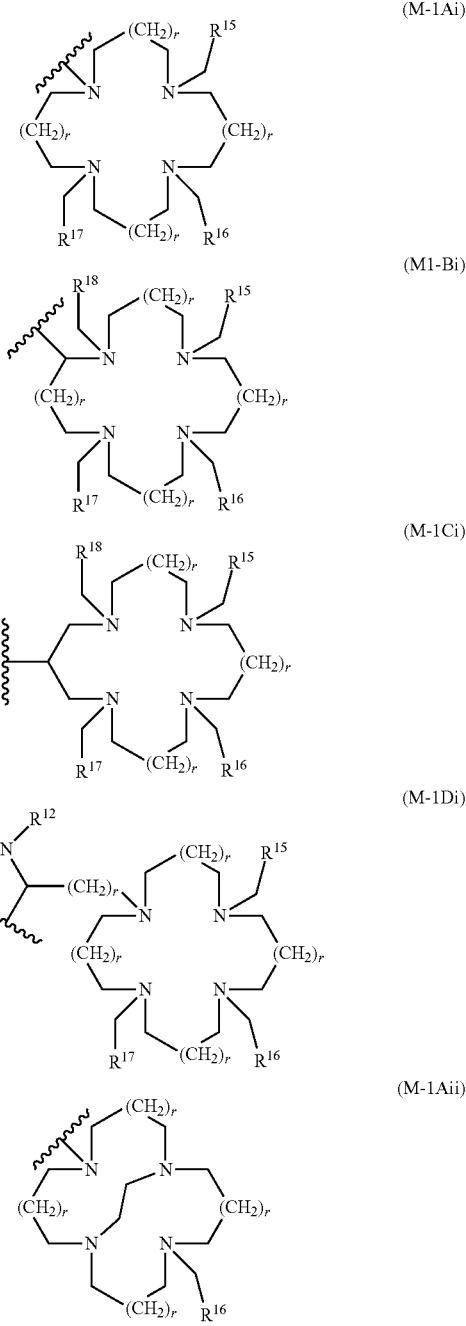

-continued

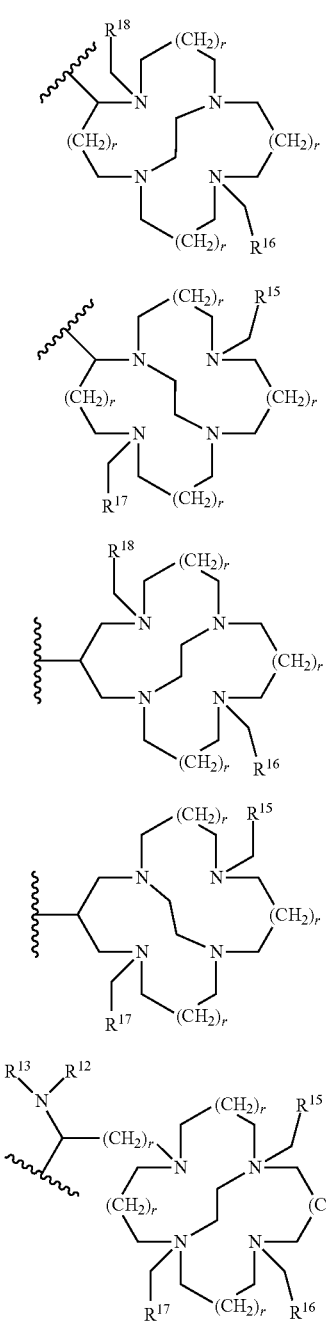

wherein ⁓ represents the bond which attaches $R^M$ to the rest of the molecule of in Formula (1); and
r is 0 or 1, and $R^{12}$ and $R^{13}$ are described herein.

In some embodiments, $R^{15}$ to $R^{18}$ are each independently selected from the group consisting of —C(=O)N($R^{14}$)$_2$, —P(=O)(O$R^{14}$)$_2$, —P(=O)O$R^{14}$($R^{14}$), and —P(=O)($R^{14}$)$_2$. In some embodiments, $R^{15}$ to $R^{18}$ are each independently selected from the group consisting of —C(=O)NH$_2$, —P(=O)(OH)$_2$, —P(=O)(OH)H, —P(=O)(OH)O$C_{1-6}$alkyl, wherein $C_{1-6}$alkyl is optionally substituted by one or more $R^8$. In the instance where $R^{15}$ to $R^{18}$ is not substituted with one or more $R^8$, it will be understood that a hydrogen atom will remain as the substitution.

In some embodiments, $R^M$ is a chelating moiety having a structure of Formula (M-1E), wherein ⁓ represents the bond which attaches $R^M$ to the rest of the molecule of in Formula (1):

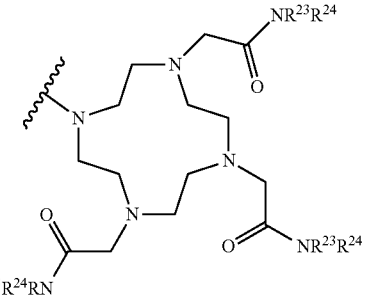

wherein $R^{23}$ and $R^{24}$ are each independently selected from the group consisting of H alkyl, alkenyl, alkynyl, carbocyclyl, heterocyclyl, alkylcarbocyclyl, and alkylheterocyclyl, each of which is optionally substituted; or at least one $R^{23}$ and $R^{24}$ together form an optionally substituted heterocyclyl.

In one embodiment, $R^{23}$ and $R^{24}$ are each independently selected from the group consisting of H, $C_{1-10}$alkyl, $C_{2-10}$alkenyl, $C_{2-10}$alkynyl, 3-10 membered carbocyclyl, 3-10 membered heterocyclyl, $C_{1-10}$alkyl-3-10-membered carbocyclyl, $C_{1-10}$alkyl-3-10-membered heterocyclyl, each of which is optionally substituted; or at least one $R^{23}$ and $R^{24}$ together form an optionally substituted 3-10-membered heterocyclyl. In some embodiments, each $R^{23}$ and $R^{24}$ are independently optionally substituted with one or more $R^8$. In the instance where $R^{23}$ and $R^{24}$ is not substituted with one or more $R^8$, it will be understood that a hydrogen atom will remain as the substitution.

In one embodiment, $R^M$ is a chelating moiety having a structure of Formula (M-1F), wherein ⁓ represents the bond which attaches $R^M$ to the rest of the molecule of in Formula (1):

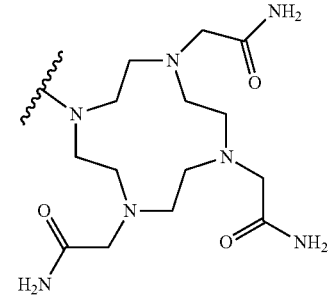

In one embodiment, —$X^3$-$L^2$-$R^M$ in Formula (1) is 2(R,S)-[1,4,7,10-tetraazacyclododecane-4,7,10-triacetamido]-5-amidopentanoic acid.

In some embodiments, $R^M$ or the compound of Formula (1) is optionally complexed to a radioisotope. Exemplary radioisotope that are optionally chelated by $R^M$ or the compound of Formula (1) include $^{44}$Sc, $^{47}$Sc, $^{51}$Cr, $^{51}$Mn, $^{52m}$Mn, $^{52g}$Mn, $^{52}$Fe, $^{55}$Co, $^{58}$Co, $^{58m}$Co, $^{61}$Co, $^{56}$Ni, $^{57}$Ni, $^{61}$Cu, $^{62}$Cu, $^{64}$Cu, $^{67}$Cu, $^{66}$Ga, $^{68}$Ga, $^{67}$Ga, $^{86}$Y $^{89}$Y$^{90}$Y $^{89}$Zr, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{17m}$Sn, $^{121}$Sn, $^{127}$Te, $^{134}$La, $^{142}$Pr, $^{143}$Pr, $^{149}$Pm, $^{151}$Pm, $^{149}$Tb, $^{152}$Eu, $^{153}$Sm, $^{157}$Gd, $^{149}$Tb, $^{152}$Tb, $^{155}$Tb, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{203}$Pb, $^{211}$Pb, $^{212}$Pb, $^{211}$At, $^{212}$Bi, $^{213}$Bi, $^{223}$Ra, $^{225}$Ac, and $^{227}$Th.

In some embodiments, $R^M$ or the compound of Formula (1) is optionally complexed to a radioisotope selected from the group consisting of $^{44}$Sc, $^{47}$Sc, $^{51}$Mn, $^{52m}$Mn, $^{52g}$Mn, $^{55}$Co, $^{58}$Co, $^{58m}$Co, $^{61}$Co, $^{61}$Cu, $^{62}$Cu, $^{64}$Cu, $^{67}$Cu, $^{68}$Ga, $^{86}$Y, $^{90}$Y$^{89}$Zr, $^{111}$In, $^{134}$La, $^{152}$Eu, $^{149}$Tb, $^{152}$Tb, $^{155}$Tb, $^{161}$Tb, $^{177}$Lu, $^{203}$Pb, $^{211}$Pb, $^{212}$Pb, $^{212}$Bi, $^{213}$Bi, $^{225}$Ac, and $^{227}$Th. In one embodiment, $R^M$ is optionally complexed to $^{212}$Pb. In one embodiment, the compound of Formula (1) is optionally complexed to $^{212}$Pb. In one embodiment, the compound of Formula (1) is complexed to $^{212}$Pb.

If $R^M$ or the compound of Formula (1) is complexed to a radioisotope described herein, the complex comprising the compound of Formula (1) and radioisotope may be called a radiopharmaceutical. It will be appreciated that reference herein to a compound of Formula (1) being "complexed" to a radioisotope is understood to mean that a radioisotope is complexed to $R^M$ or the compound of Formula (1). An example of a compound of Formula (1) complexed to a radioisotope via $R^M$ is provided below:

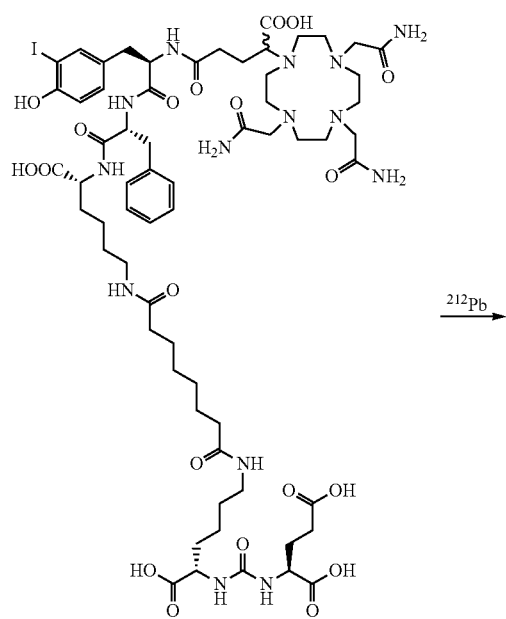

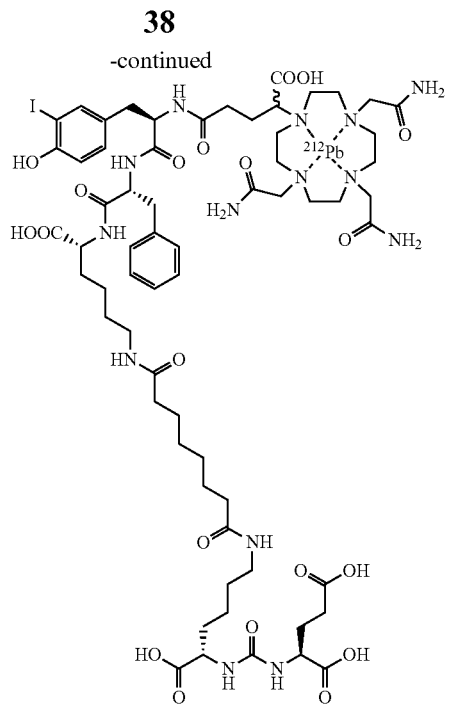

PSMA Targeting Ligands

In the above Formula (1), A is a PSMA targeting ligand. In one embodiment, A comprises a urea building block (A-1):

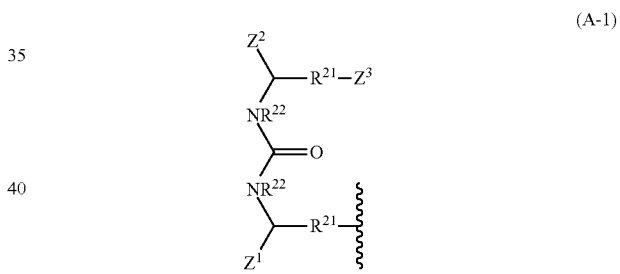

wherein

∼ represents the bond which attaches A to the rest of the molecule of in Formula (1).

In some embodiments, $R^{21}$ is —$C_{1-20}$alkyl- which is uninterrupted or interrupted and optionally substituted. In some embodiments, $R^{21}$ is a —$C_{1-10}$alkyl- which is uninterrupted or interrupted and optionally substituted. In some embodiments, $R^{21}$ is a —$C_{1-6}$alkyl- which is uninterrupted or interrupted and optionally substituted. In some embodiments, $R^{21}$ is optionally substituted with one or more $R^8$. In the instance where $R^{21}$ is not substituted with one or more $R^8$, it will be understood that a hydrogen atom will remain as the substitution.

In some embodiments, each $R^{22}$ is independently selected from the group consisting of H, alkyl, alkenyl, alkynyl, carbocyclyl, heterocyclyl, alkylcarbocyclyl, and alkylheterocyclyl, each of which is optionally substituted. In some embodiments, each $R^{22}$ is H. In some embodiments, each $R^{22}$ is optionally substituted with one or more $R^8$. In the instance where $R^{22}$ is not substituted with one or more $R^8$, it will be understood that a hydrogen atom will remain as the substitution.

In some embodiments, $Z^1$ to $Z^3$ are each independently selected from the group consisting of —C(=O)OR$^9$, —S(=O)OR$^9$, —S(=O)$_2$OR$^9$, —S(=O)(OR$^9$)$_2$, —OS(=O)OR$^9$, —OS(=O)$_2$OR$^9$, —OS(=O)(OR$^9$)$_2$, —P(=O)(OR$^9$)$_2$, —P(=O)OR$^9$(R$^9$), —OP(=O)(OR$^9$)$_2$, and —OP(=O)OR$^9$(R$^9$). In one embodiment, $Z^1$ to $Z^3$ are each independently —C(=O)OR$^9$. In one embodiment, $Z^1$ to $Z^3$ are each —COOH.

In some embodiments, A is a PSMA targeting ligand having the structure of Formula (A-2):

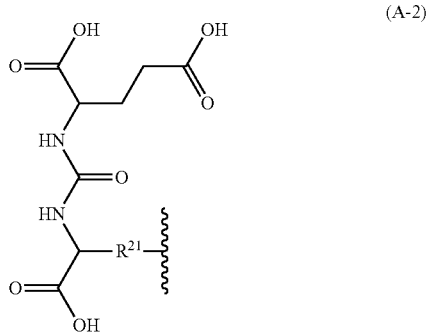

(A-2)

wherein:
 ⁓ represents the bond which attaches A to the rest of the molecule of in Formula (1); and
$R^{21}$ is $C_{1-20}$alkyl optionally substituted with one or more $R^8$.

$R^8$ to $R^1$

In the above Formula (1), each of $R^1$ to $R^7$, $R^{12}$ to $R^{14}$, and $R^{19}$ to $R^{24}$ may be optionally substituted. In one embodiment, each of $R^1$, $R^2$, $R^3$, $R^4$, $R^5$, $R^6$, $R^7$, $R^{12}$, $R^{13}$, $R^{14}$, $R^{19}$, $R^{20}$, $R^{21}$, $R^{22}$, $R^{23}$ and $R^{24}$ may be optionally substituted with one or more $R^8$. In the instance where $R^1$, $R^2$, $R^3$, $R^4$, $R^5$, $R^6$, $R^7$, $R^{12}$, $R^{13}$, $R^{14}$, $R^{19}$, $R^{20}$, $R^{21}$, $R^{22}$, $R^{23}$ and $R^{24}$ is not substituted with one or more $R^8$, then it will be understood that a hydrogen atom will remain as the substitution.

In some embodiments, $R^1$ is substituted with one, two, three, four, five, or more, $R^8$ substituents. In one embodiment, $R^1$ is substituted with one $R^8$ substituent. In one embodiment, $R^1$ is substituted with two $R^8$ substituents. In one embodiment, $R^1$ is substituted with three $R^8$ substituents. In one embodiment, $R^1$ is substituted with four $R^8$ substituents. In one embodiment, $R^1$ is substituted with five $R^8$ substituents. In one embodiment, $R^1$ is substituted with more than five $R^8$ substituents.

In some embodiments, $R^2$ is substituted with one, two, three, four, five, or more, $R^8$ substituents. In one embodiment, $R^2$ is substituted with one $R^8$ substituent. In one embodiment, $R^2$ is substituted with two $R^8$ substituents. In one embodiment, $R^2$ is substituted with three $R^8$ substituents. In one embodiment, $R^2$ is substituted with four $R^8$ substituents. In one embodiment, $R^2$ is substituted with five $R^8$ substituents. In one embodiment, $R^2$ is substituted with more than five $R^8$ substituents.

In some embodiments, $R^3$ is substituted with one, two, three, four, five, or more, $R^8$ substituents. In one embodiment, $R^3$ is substituted with one $R^8$ substituent. In one embodiment, $R^3$ is substituted with two $R^8$ substituents. In one embodiment, $R^3$ is substituted with three $R^8$ substituents. In one embodiment, $R^3$ is substituted with four $R^8$ substituents. In one embodiment, $R^3$ is substituted with five $R^8$ substituents. In one embodiment, $R^3$ is substituted with more than five $R^8$ substituents.

In some embodiments, $R^4$ is substituted with one, two, three, four, five, or more, $R^8$ substituents. In one embodiment, $R^4$ is substituted with one $R^8$ substituent. In one embodiment, $R^4$ is substituted with two $R^8$ substituents. In one embodiment, $R^4$ is substituted with three $R^8$ substituents. In one embodiment, $R^4$ is substituted with four $R^8$ substituents. In one embodiment, $R^4$ is substituted with five $R^8$ substituents. In one embodiment, $R^4$ is substituted with more than five $R^8$ substituents.

In some embodiments, $R^5$ is substituted with one, two, three, four, five, or more, $R^8$ substituents. In one embodiment, $R^5$ is substituted with one $R^8$ substituent. In one embodiment, $R^5$ is substituted with two $R^8$ substituents. In one embodiment, $R^5$ is substituted with three $R^8$ substituents. In one embodiment, $R^5$ is substituted with four $R^8$ substituents. In one embodiment, $R^5$ is substituted with five $R^8$ substituents. In one embodiment, $R^5$ is substituted with more than five $R^8$ substituents.

In some embodiments, $R^6$ is substituted with one, two, three, four, five, or more, $R^8$ substituents. In one embodiment, $R^6$ is substituted with one $R^8$ substituent. In one embodiment, $R^6$ is substituted with two $R^8$ substituents. In one embodiment, $R^6$ is substituted with three $R^8$ substituents. In one embodiment, $R^6$ is substituted with four $R^8$ substituents. In one embodiment, $R^6$ is substituted with five $R^8$ substituents. In one embodiment, $R^6$ is substituted with more than five $R^8$ substituents.

In some embodiments, $R^7$ is substituted with one, two, three, four, five, or more, $R^8$ substituents. In one embodiment, $R^7$ is substituted with one $R^8$ substituent. In one embodiment, $R^7$ is substituted with two $R^8$ substituents. In one embodiment, $R^7$ is substituted with three $R^8$ substituents. In one embodiment, $R^7$ is substituted with four $R^8$ substituents. In one embodiment, $R^7$ is substituted with five $R^8$ substituents. In one embodiment, $R^7$ is substituted with more than five $R^8$ substituents.

In some embodiments, $R^{12}$ is substituted with one, two, three, four, five, or more, $R^8$ substituents. In one embodiment, $R^{12}$ is substituted with one $R^8$ substituent. In one embodiment, $R^{12}$ is substituted with two $R^8$ substituents. In one embodiment, $R^{12}$ is substituted with three $R^8$ substituents. In one embodiment, $R^{12}$ is substituted with four $R^8$ substituents. In one embodiment, $R^{12}$ is substituted with five $R^8$ substituents. In one embodiment, $R^{12}$ is substituted with more than five $R^8$ substituents.

In some embodiments, $R^{13}$ is substituted with one, two, three, four, five, or more, $R^8$ substituents. In one embodiment, $R^{13}$ is substituted with one $R^8$ substituent. In one embodiment, $R^{13}$ is substituted with two $R^8$ substituents. In one embodiment, $R^{14}$ is substituted with three $R^8$ substituents. In one embodiment, $R^{13}$ is substituted with four $R^8$ substituents. In one embodiment, $R^{13}$ is substituted with five $R^8$ substituents. In one embodiment, $R^{13}$ is substituted with more than five $R^8$ substituents.

In some embodiments, $R^{14}$ is substituted with one, two, three, four, five, or more, $R^8$ substituents. In one embodiment, $R^{14}$ is substituted with one $R^8$ substituent. In one embodiment, $R^{14}$ is substituted with two $R^8$ substituents. In one embodiment, $R^{14}$ is substituted with three $R^8$ substituents. In one embodiment, $R^{14}$ is substituted with four $R^8$ substituents. In one embodiment, $R^{14}$ is substituted with five $R^8$ substituents. In one embodiment, $R^{14}$ is substituted with more than five $R^8$ substituents.

In some embodiments, $R^{19}$ is substituted with one, two, three, four, five, or more, $R^8$ substituents. In one embodiment, $R^{19}$ is substituted with one $R^8$ substituent. In one embodiment, $R^{19}$ is substituted with two $R^8$ substituents. In one embodiment, $R^{19}$ is substituted with three $R^8$ substituents. In one embodiment, $R^{19}$ is substituted with four $R^8$ substituents. In one embodiment, $R^{19}$ is substituted with five $R^8$ substituents. In one embodiment, $R^{19}$ is substituted with more than five $R^8$ substituents.

In some embodiments, $R^{21}$ is substituted with one, two, three, four, five, or more, $R^8$ substituents. In one embodiment, $R^{21}$ is substituted with one $R^8$ substituent. In one embodiment, $R^{21}$ is substituted with two $R^8$ substituents. In one embodiment, $R^{21}$ is substituted with three $R^8$ substituents. In one embodiment, $R^{21}$ is substituted with four $R^8$ substituents. In one embodiment, $R^{21}$ is substituted with five $R^8$ substituents. In one embodiment, $R^{21}$ is substituted with more than five $R^8$ substituents.

In some embodiments, $R^{21}$ is substituted with one, two, three, four, five, or more, $R^8$ substituents. In one embodiment, $R^{21}$ is substituted with one $R^8$ substituent. In one embodiment, $R^{21}$ is substituted with two $R^8$ substituents. In one embodiment, $R^{21}$ is substituted with three $R^8$ substituents. In one embodiment, $R^{21}$ is substituted with four $R^8$ substituents. In one embodiment, $R^{21}$ is substituted with five $R^8$ substituents. In one embodiment, $R^{21}$ is substituted with more than five $R^8$ substituents.

In some embodiments, $R^{22}$ is substituted with one, two, three, four, five, or more, $R^8$ substituents. In one embodiment, $R^{22}$ is substituted with one $R^8$ substituent. In one embodiment, $R^{22}$ is substituted with two $R^8$ substituents. In one embodiment, $R^{22}$ is substituted with three $R^8$ substituents. In one embodiment, $R^{22}$ is substituted with four $R^8$ substituents. In one embodiment, $R^{22}$ is substituted with five $R^8$ substituents. In one embodiment, $R^{22}$ is substituted with more than five $R^8$ substituents.

In some embodiments, $R^{23}$ is substituted with one, two, three, four, five, or more, $R^8$ substituents. In one embodiment, $R^{23}$ is substituted with one $R^8$ substituent. In one embodiment, $R^{23}$ is substituted with two $R^8$ substituents. In one embodiment, $R^{23}$ is substituted with three $R^8$ substituents. In one embodiment, $R^{23}$ is substituted with four $R^8$ substituents. In one embodiment, $R^{23}$ is substituted with five $R^8$ substituents. In one embodiment, $R^{23}$ is substituted with more than five $R^8$ substituents.

In some embodiments, $R^{24}$ is substituted with one, two, three, four, five, or more, $R^8$ substituents. In one embodiment, $R^{24}$ is substituted with one $R^8$ substituent. In one embodiment, $R^{24}$ is substituted with two $R^8$ substituents. In one embodiment, $R^{24}$ is substituted with three $R^8$ substituents. In one embodiment, $R^{24}$ is substituted with four $R^8$ substituents. In one embodiment, $R^{24}$ is substituted with five $R^8$ substituents. In one embodiment, $R^{24}$ is substituted with more than five $R^8$ substituents.

It will be understood that, when any of $R^8$, $R^2$, $R^3$, $R^4$, $R_5$, $R^6$, $R^7$, $R^{82}$, $R^{83}$, $R^{84}$, $R^{89}$, $R^{20}$, $R^{21}$, $R^{22}$, $R^{23}$ and $R^{24}$ is substituted with one or more $R^8$ substituents, the one or more substituents may be the same substituent or a different substituent (e.g., the $R^8$ substituents are independently selected from one another).

In the above Formula (1), each of $Y^1$ to $Y^4$ may be optionally substituted. In one embodiment, each of $Y^1$, $Y^2$, $Y^3$, and $Y^4$ may be optionally substituted with one or more $R^8$. In the instance where $Y^1$, $Y^2$, $Y^3$, and $Y^4$ is not substituted with one or more $R^8$, then it will be understood that a hydrogen atom will remain as the substitution. In some embodiments, $Y^1$ is substituted with one, two, three, four, five, or more, $R^8$ substituents. In one embodiment, $Y^1$ is substituted with one $R^8$ substituent. In one embodiment, $Y^1$ is substituted with two $R^8$ substituents. In one embodiment, $Y^1$ is substituted with three $R^8$ substituents. In one embodiment, $Y^1$ is substituted with four $R^8$ substituents. In one embodiment, $Y^1$ is substituted with five $R^8$ substituents. In one embodiment, $Y^1$ is substituted with more than five $R^8$ substituents. In one embodiment, $Y^2$ is substituted with one $R^8$ substituent. In one embodiment, $Y^2$ is substituted with two $R^8$ substituents. In one embodiment, $Y^2$ is substituted with three $R^8$ substituents. In one embodiment, $Y^2$ is substituted with four $R^8$ substituents. In one embodiment, $Y^2$ is substituted with five $R^8$ substituents. In one embodiment, $Y^2$ is substituted with more than five $R^8$ substituents. In one embodiment, $Y^3$ is substituted with one $R^8$ substituent. In one embodiment, $Y^3$ is substituted with two $R^8$ substituents. In one embodiment, $Y^3$ is substituted with three $R^8$ substituents. In one embodiment, $Y^3$ is substituted with four $R^8$ substituents. In one embodiment, $Y^3$ is substituted with five $R^8$ substituents. In one embodiment, $Y^3$ is substituted with more than five $R^8$ substituents. In one embodiment, $Y^4$ is substituted with one $R^8$ substituent. In one embodiment, $Y^4$ is substituted with two $R^8$ substituents. In one embodiment, $Y^4$ is substituted with three $R^8$ substituents. In one embodiment, $Y^4$ is substituted with four $R^8$ substituents. In one embodiment, $Y^4$ is substituted with five $R^8$ substituents. In one embodiment, $Y^4$ is substituted with more than five $R^8$ substituents.

In the above Formula (1), each $L^1$, $L^2$ and $L^3$ may be optionally substituted. In one embodiment, each $L^1$, $L^2$ and $L^3$ may be optionally substituted with one or more $R^8$. In the instance where $L^1$, $L^2$ and $L^3$ is not substituted with one or more $R^8$, then it will be understood that a hydrogen atom will remain as the substitution. In some embodiments, $L^1$ is substituted with one, two, three, four, five, or more, $R^8$ substituents. In one embodiment, $L^1$ is substituted with one $R^8$ substituent. In one embodiment, $L^1$ is substituted with two $R^8$ substituents. In one embodiment, $L^1$ is substituted with three $R^8$ substituents. In one embodiment, $L^1$ is substituted with four $R^8$ substituents. In one embodiment, $L^1$ is substituted with five $R^8$ substituents. In one embodiment, $L^1$ is substituted with more than five $R^8$ substituents. In one embodiment, $L^2$ is substituted with one $R^8$ substituent. In one embodiment, $L^2$ is substituted with two $R^8$ substituents. In one embodiment, $L^2$ is substituted with three $R^8$ substituents. In one embodiment, $L^2$ is substituted with four $R^8$ substituents. In one embodiment, $L^2$ is substituted with five $R^8$ substituents. In one embodiment, $L^2$ is substituted with more than five $R^8$ substituents. In one embodiment, $L^2$ is substituted with more than five $R^8$ substituents. In one embodiment, $L^3$ is substituted with one $R^8$ substituent. In one embodiment, $L^3$ is substituted with two $R^8$ substituents. In one embodiment, $L^3$ is substituted with three $R^8$ substituents. In one embodiment, $L^3$ is substituted with four $R^8$ substituents. In one embodiment, $L^3$ is substituted with five $R^8$ substituents. In one embodiment, $L^3$ is substituted with more than five $R^8$ substituents.

In the above Formula (1), each $R^8$ may be independently selected from the group consisting of H, halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, —$NO_2$, —CN, —SCN, —$N_3$, =O, —$N(R^9)_2$, —$C(=O)N(R^9)_2$, —$S(=O)N(R^9)_2$, —$S(=O)_2N(R^9)_2$, —$OR^9$, —$SR^9$, —$OC(=O)R^9$, —$C(=O)R^9$, —$C(=O)OR^9$, —$S(=O)R^9$, —$S(=O)_2R^9$, —$S(=O)OR^9$, —$S(=O)_2OR^9$, —$S(=O)(OR^9)_2$, —$OS(=O)R^9$, —$OS(=O)_2R^9$, —$OS(=O)OR_9$, —$OS(=O)_2OR^9$, —$OS(=O)$ $(OR^9)_2$, —$N(R^9)C(\!=\!O)R^9$, —$N(R^9)S(\!=\!O)R^9$, —$N(R^9)C(\!=\!O)N(R^9)_2$, —$N(R^9)S(\!=\!O)_2R^9$, —$P(\!=\!O)(OR^9)_2$, —$P(\!=\!O)OR^9(R^9)$, —$P(\!=\!O)(R^9)_2$, —$OP(\!=\!O)(OR^9)_2$, —$OP(\!=\!O)OR^9(R^9)$ and —$OP(\!=\!O)(R^9)_2$.

In the above Formula (1), where $R^8$ is $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl may be optionally substituted with one or more $R^{10}$ substituents. In some embodiments, when $R^1$ is $C_{1-10}$alkyl, $OC_{1-10}$alkyl, $C_{1-10}$ haloalkyl, $OC_{1-10}$haloalkyl, $C_{2-10}$alkenyl, $C_{2-10}$alkynyl, $OC_{2-10}$alkenyl, $OC_{2-10}$alkynyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl may be optionally substituted with one, two, three, four, five or more than five $R^{10}$ substituents. It will be understood that, when $R^8$ is substituted with one or more $R^{10}$ substituents, the one or more substituents may be the same substituent or a different substituent (e.g., the $R^{10}$ substituents are independently selected from one another).

In the above Formula (1), each $R^9$ may be independently selected from the group consisting of H, $C_{1-6}$alkyl, 3-10 membered carbocyclyl, 3-10-membered heterocyclyl, $C_{1-6}$ alkyl-3-10-membered-carbocyclyl, and $C_{1-6}$alkyl-3-10-membered-heterocyclyl.

In the above Formula (1), when $R^9$ is $C_{1-6}$alkyl, 3-10 membered carbocyclyl, 3-10-membered heterocyclyl, $C_{1-6}$alkyl-3-10-membered-carbocyclyl, and $C_{1-6}$alkyl-3-10-membered-heterocyclyl, each $C_{1-6}$alkyl, 3-10-membered-carbocyclyl, and 3-10-membered heterocyclyl may be optionally substituted with one or more $R^{10}$ substituents. In some embodiments, when $R^9$ is $C_{1-6}$alkyl, 3-10 membered carbocyclyl, 3-10-membered heterocyclyl, $C_{1-6}$alkyl-3-10-membered-carbocyclyl, and $C_{1-6}$alkyl-3-10-membered-heterocyclyl, each $C_{1-6}$alkyl, 3-10-membered-carbocyclyl, and 3-10-membered heterocyclyl may be optionally substituted with one, two, three, four, five or more than five $R^{10}$ substituents. It will be understood that, when $R^9$ is substituted with one or more $R^{10}$ substituents, the one or more substituents may be the same substituent or a different substituent (e.g., the $R^{10}$ substituents are independently selected from one another).

In the above Formula (1), each $R^{10}$ may be independently selected from the group consisting of H, halogen, —$NO_2$, —$N(R^{11})_2$, —CN, —SCN, —$N_3$, $=\!O$, —$C(\!=\!O)R^{11}$, —$C(\!=\!O)OR^{11}$, —$C(\!=\!O)N(R^{11})_2$, —$N(R^{11})C(\!=\!O)R^{11}$, —$OR^{11}$, —$P(\!=\!O)(OR^{11})_2$, —$P(\!=\!O)OR^{11}(R^{11})$, —$P(\!=\!O)(R^1)_2$, $C_{1-6}$alkyl, and —$OC_{1-6}$alkyl. In the above Formula (1), each $R^{11}$ may be independently selected from the group consisting of H, $C_{1-10}$alkyl, $C_{1-10}$alkyl, $C_{2-10}$alkenyl, $C_{2-10}$alkynyl, 3-10 membered carbocyclyl, 3-10 membered heterocyclyl, $C_{1-10}$alkyl-3-10-membered carbocyclyl, $C_{1-10}$alkyl-3-10-membered heterocyclyl. In one embodiment, each $R^{11}$ may be independently selected from the group consisting of H and $C_{1-6}$alkyl. In one embodiment, $R^{11}$ is H. In one embodiment, $R^{11}$ is $C_{1-6}$alkyl.

In the above Formula (1), each $R^1$ and $R^2$ may be independently optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, $=\!O$, —$C(\!=\!O)R^9$, —$C(\!=\!O)OR^9$, —$N(R^9)C(\!=\!O)R^9$, and —$OR^9$, wherein each $C_{1-10}$alkyl, $C_{1-10}$haloalkyl, $C_{2-10}$alkenyl and $C_{2-10}$alkynyl is optionally substituted with one or more $R^{10}$. In some embodiments, each $R^1$ and $R^2$ may be independently optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, $=\!O$, —$C(\!=\!O)R^{11}$, —$C(\!=\!O)OR^{11}$, —$N(R^{11})C(\!=\!O)R^{11}$, and —$OR^{11}$. In some embodiments, $R^1$ and $R^2$ may be independently optionally substituted with one or more groups selected from halogen, $C_{1-6}$alkyl, $OC_{1-6}$ alkyl, $C_{1-6}$haloalkyl, $OC_{1-6}$haloalkyl, —$NO_2$, —$NH_2$, —CN, —SCN, —COOH and —OH. In some embodiments, $R^1$ and $R^2$ may be independently optionally substituted with one or more groups selected from halogen, —$NO_2$, —$NH_2$, —CN, —SCN, —COOH and —OH.

In one embodiment, $R^1$ is optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, $=\!O$, —$C(\!=\!O)R^9$, —$C(\!=\!O)OR^9$, —$N(R^9)C(\!=\!O)R^9$, and —$OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^1$ is optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, $=\!O$, —$C(\!=\!O)R^{11}$, —$C(\!=\!O)OR^{11}$, —$N(R^{11})C(\!=\!O)R^{11}$, and —$OR^{11}$. In some embodiments, $R^1$ is optionally substituted with one or more groups selected from halogen, $C_{1-6}$alkyl, $OC_{1-6}$ alkyl, $C_{1-6}$haloalkyl, $OC_{1-6}$haloalkyl, —$NO_2$, —$NH_2$, —CN, —SCN, —COOH and —OH. In some embodiments, $R^1$ is optionally substituted with one or more groups selected from halogen, —$NO_2$, —$NH_2$, —CN, —SCN, —COOH and —OH. In one embodiment, $R^1$ is unsubstituted (i.e. substituted with H).

In one embodiment, $R^1$ is an aryl or alkylaryl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, $=\!O$, —$C(\!=\!O)R^9$, —$C(\!=\!O)OR^9$, —$N(R^9)C(\!=\!O)R^9$, and —$OR^9$, wherein each $C_{1-10}$alkyl, $C_{1-10}$haloalkyl, $C_{2-10}$alkenyl and $C_{2-10}$alkynyl is optionally substituted with one or more $R^{10}$. In some embodiments, $R^1$ is an aryl or alkylaryl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, $=\!O$, —$C(\!=\!O)R^{11}$, —$C(\!=\!O)OR^{11}$, —$N(R^{11})C(\!=\!O)R^{11}$, and —$OR^{11}$. In some embodiments, $R^1$ is an aryl or alkylaryl optionally substituted with one or more groups selected from halogen, $C_{1-6}$alkyl, $OC_{1-6}$alkyl, $C_{1-6}$haloalkyl, $OC_{1-6}$haloalkyl, —$NO_2$, —$NH_2$, —CN, —SCN, —COOH and —OH. In some embodiments, $R^1$ is benzyl optionally substituted with one or more groups selected from halogen, —$NO_2$, —$NH_2$, —CN, —SCN, —COOH and —OH. In some embodiments, $R^1$ is an aryl or alkylaryl optionally substituted with one or more groups selected from halogen, —$NO_2$, —$NH_2$, —CN, —SCN, —COOH and —OH. In one embodiment, $R^1$ is an unsubstituted aryl or an unsubstituted alkylaryl (i.e. 'substituted' with H).

In one embodiment, $R^1$ is phenyl or benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^1$ is phenyl or benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^{11}$, $-C(=O)OR^{11}$, $-N(R^{11})C(=O)R^{11}$, and $-OR^1$. In some embodiments, $R^1$ is phenyl or benzyl optionally substituted with one or more groups selected from halogen, $C_{1-6}$alkyl, $OC_{1-6}$alkyl, $C_{1-6}$haloalkyl, $OC_{1-6}$haloalkyl, $-NO_2$, $-NH_2$, $-CN$, $-SCN$, $-COOH$ and $-OH$. In some embodiments, $R^1$ is phenyl or benzyl optionally substituted with one or more groups selected from halogen, $-NO_2$, $-NH_2$, $-CN$, $-SCN$, $-COOH$ and $-OH$. In some embodiments, $R^1$ is phenyl or benzyl optionally substituted with one or more groups selected from halogen, $-NO_2$, $-NH_2$, $-CN$, $-SCN$, $-COOH$ and $-OH$. In one embodiment, $R^1$ is an unsubstituted phenyl or unsubstituted benzyl (i.e. 'substituted' with H).

In one embodiment, $R^1$ is benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^1$ is benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^{11}$, $-C(=O)OR^{11}$, $-N(R^{11})C(=O)R^{11}$, and $-OR^{11}$. In some embodiments, $R^1$ is benzyl optionally substituted with one or more groups selected from halogen, $C_{1-6}$alkyl, $OC_{1-6}$alkyl, $C_{1-6}$haloalkyl, $OC_{1-6}$haloalkyl, $-NO_2$, $-NH_2$, $-CN$, $-SCN$, $-COOH$ and $-OH$.

In some embodiments, $R^1$ is benzyl optionally substituted with one or more groups selected from halogen, $-NO_2$, $-NH_2$, $-CN$, $-SCN$, $-COOH$ and $-OH$. In some embodiments, $R^1$ is benzyl optionally substituted with one or more groups selected from halogen, $-NO_2$, $-NH_2$, $-CN$, $-SCN$, $-COOH$ and $-OH$. In one embodiment, $R^1$ is an unsubstituted benzyl (i.e. 'substituted' with H).

In one embodiment, $R^2$ is optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^2$ is optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^{11}$, $-C(=O)OR^{11}$, $-N(R^{11})C(=O)R^{11}$, and $-OR^{11}$. In some embodiments, $R^2$ is optionally substituted with one or more groups selected from halogen, $C_{1-6}$alkyl, $OC_{1-6}$alkyl, $C_{1-6}$haloalkyl, $OC_{1-6}$haloalkyl, $-NO_2$, $-NH_2$, $-CN$, $-SCN$, $-COOH$ and $-OH$. In some embodiments, $R^2$ is optionally substituted with one or more groups selected from halogen, $-NO_2$, $-NH_2$, $-CN$, $-SCN$, $-COOH$ and $-OH$. In one embodiment, $R^2$ is optionally substituted with one or more halogen (e.g. one or more of I, Br, Cl, or Br) or $-OH$.

In one embodiment, $R^2$ is an aryl or alkylaryl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$. In some embodiments, $R^2$ is an aryl or alkylaryl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^{11}$, $-C(=O)OR^{11}$, $-N(R^{11})C(=O)R^{11}$, and $-OR^{11}$. In some embodiments, $R^2$ is an aryl or alkylaryl optionally substituted with one or more groups selected from halogen, $C_{1-6}$alkyl, $OC_{1-6}$alkyl, $C_{1-6}$haloalkyl, $OC_{1-6}$haloalkyl, $-NO_2$, $-NH_2$, $-CN$, $-SCN$, $-COOH$ and $-OH$. In some embodiments, $R^2$ is an aryl or alkylaryl optionally substituted with one or more groups selected from halogen, $-NO_2$, $-NH_2$, $-CN$, $-SCN$, $-COOH$ and $-OH$. In one embodiment, $R^2$ is an aryl or alkylaryl optionally substituted with one or more halogen (e.g. one or more of I, Br, Cl, or Br) or $-OH$.

In one embodiment, $R^2$ is phenyl or benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$. In some embodiments, $R^2$ is phenyl or benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^{11}$, $-C(=O)OR^{11}$, $-N(R^{11})C(=O)R^{11}$, and $-OR^1$. In some embodiments, $R^2$ is phenyl or benzyl optionally substituted with one or more groups selected from halogen, $C_{1-6}$alkyl, $OC_{1-6}$alkyl, $C_{1-6}$haloalkyl, $OC_{1-6}$haloalkyl, $-NO_2$, $-NH_2$, $-CN$, $-SCN$, $-COOH$ and $-OH$. In some embodiments, $R^2$ is phenyl or benzyl optionally substituted with one or more groups selected from halogen, $-NO_2$, $-NH_2$, $-CN$, $-SCN$, $-COOH$ and $-OH$. In some embodiments, $R^2$ is phenyl or benzyl optionally substituted with one or more groups selected from halogen, $-NO_2$, $-NH_2$, $-CN$, $-SCN$, $-COOH$ and $-OH$. In one embodiment, $R^2$ is phenyl or benzyl optionally substituted with one or more halogen (e.g. one or more of I, Br, Cl, or Br) or $-OH$.

In one embodiment, $R^2$ is benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^2$ is benzyl optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^D$, —C(=O)$OR^{11}$, —$N(R^{11})C(=O)R^{11}$, and —$OR^{11}$. In some embodiments, $R^2$ is benzyl optionally substituted with one or more groups selected from halogen, $C_{1-6}$alkyl, $OC_{1-6}$alkyl, $C_{1-6}$haloalkyl, $OC_{1-6}$haloalkyl, —$NO_2$, —$NH_2$, —CN, —SCN, —COOH and —OH.

In some embodiments, $R^2$ is benzyl optionally substituted with one or more groups selected from halogen, —$NO_2$, —$NH_2$, —CN, —SCN, —COOH and —OH. In some embodiments, $R^2$ is benzyl optionally substituted with one or more groups selected from halogen, —$NO_2$, —$NH_2$, —CN, —SCN, —COOH and —OH. In one embodiment, $R^2$ is benzyl optionally substituted with one or more halogen (e.g. one or more of I, Br, Cl, or Br) or —OH.

In one embodiment, $R^2$ is an aryl or alkylaryl, substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^9$, —C(=O)$OR^9$, —$N(R^9)C(=O)R^9$, and —$OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^2$ is an aryl or alkylaryl, substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^{11}$, —C(=O)$OR^{11}$, —$N(R^{11})C(=O)R^{11}$, and —$OR^1$. In some embodiments, $R^2$ is an aryl or alkylaryl, substituted with one or more groups selected from halogen, $C_{1-6}$alkyl, $OC_{1-6}$alkyl, $C_{1-6}$haloalkyl, $OC_{1-6}$haloalkyl, —$NO_2$, —$NH_2$, —CN, —SCN, —COOH and —OH. In some embodiments, $R^2$ is an aryl or alkylaryl, substituted with one or more groups selected from halogen, —$NO_2$, —$NH_2$, —CN, —SCN, —COOH and —OH. In one embodiment, $R^2$ is an aryl or alkylaryl, substituted with one or more halogen (e.g. one or more of I, Br, Cl, or Br) or —OH.

In one embodiment, $R^2$ is phenyl or benzyl, substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^5$, —C(=O)$OR^9$, —$N(R^9)C(=O)R^9$, and —$OR^9$, wherein each $C_{1-10}$alkyl, $C_{1-10}$haloalkyl, $C_{2-10}$alkenyl and $C_{2-10}$alkynyl is optionally substituted with one or more $R^{10}$. In some embodiments, $R^2$ is phenyl or benzyl, substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^{11}$, —C(=O)$OR^{11}$, —$N(R^{11})C(=O)R^{11}$, and —$OR^{11}$. In some embodiments, $R^2$ is phenyl or benzyl, substituted with one or more groups selected from halogen, $C_{1-6}$alkyl, $OC_{1-6}$alkyl, $C_{1-6}$haloalkyl, $OC_{1-6}$haloalkyl, —$NO_2$, —$NH_2$, —CN, —SCN, —COOH and —OH. In some embodiments, $R^2$ is phenyl or benzyl, substituted with one or more groups selected from halogen, —$NO_2$, —$NH_2$, —CN, —SCN, —COOH and —OH. In some embodiments, $R^2$ is phenyl or benzyl, substituted with one or more groups selected from halogen, —$NO_2$, —$NH_2$, —CN, —SCN, —COOH and —OH. In one embodiment, $R^2$ is phenyl or benzyl, substituted with one or more halogen (e.g. one or more of I, Br, Cl, or Br) or —OH.

In one embodiment, $R^2$ is benzyl substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^9$, —C(=O)$OR^9$, —$N(R^9)C(=O)R^9$, and —$OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In some embodiments, $R^2$ is benzyl substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^{11})_2$, —CN, —SCN, —$N_3$, =O, —C(=O)$R^{11}$, —C(=O)$OR^{11}$, —$N(R^{11})C(=O)R^{11}$, and —$OR^{11}$. In some embodiments, $R^2$ is benzyl substituted with one or more groups selected from halogen, $C_{1-6}$alkyl, $OC_{1-6}$alkyl, $C_{1-6}$haloalkyl, $OC_{1-6}$haloalkyl, —$NO_2$, —$NH_2$, —CN, —SCN, —COOH and —OH. In some embodiments, $R^2$ is benzyl substituted with one or more groups selected from halogen, —$NO_2$, —$NH_2$, —CN, —SCN, —COOH and —OH. In some embodiments, $R^2$ is benzyl substituted with one or more groups selected from halogen, —$NO_2$, —$NH_2$, —CN, —SCN, —COOH and —OH. In one embodiment, $R^2$ is benzyl substituted with one or more halogen (e.g. one or more of I, Br, Cl, or Br) or —OH.

In one embodiment, $R^1$ is a group of the formula:

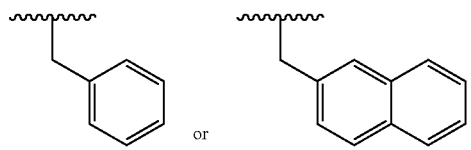 [SMILES: *Cc1ccccc1 ; *Cc1ccc2ccccc2c1]

or and $R^2$ is a group of the formula:

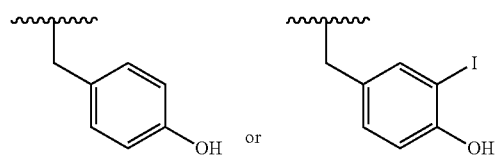 [SMILES: *Cc1ccc(O)cc1 ; *Cc1ccc(O)c(I)c1]

or wherein ∼ represents the bond which attaches $R^1$ and $R^2$, respectively, to the remainder of the compound of Formula (1).

In one embodiment, $R^1$ is a group of the formula:

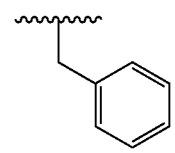 [SMILES: *Cc1ccccc1]

and $R^2$ is a group of the formula:

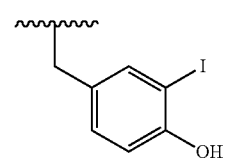 [SMILES: *Cc1ccc(O)c(I)c1]

wherein ∼ represents the bond which attaches $R^1$ and $R^2$, respectively, to the remainder of the compound of Formula (1).

In the above Formula (1), each $R^3$ may be independently optionally substituted with one or more groups H, $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$. In some embodiments, each of $R^3$ may be independently optionally substituted with one or more groups selected from $C_{1-10}$alkyl, $OC_{1-10}$alkyl, $-NH_2$, $-OH$, $-COOH$, $-C(=O)OC_{1-6}$alkyl. In one embodiment, each of $R^3$ is unsubstituted (i.e. substituted with H).

In the above Formula (1), $R^4$ to $R^7$ may be each independently optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$. In one embodiment, $R^4$ to $R^7$ are unsubstituted (i.e. 'substituted' with H).

In the above Formula (1), $R^{12}$ and $R^{13}$ may be each independently optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$. In one embodiment, $R^{12}$ and $R^{13}$ are unsubstituted (i.e. 'substituted' with H).

In the above Formula (1), each $R^{14}$ may be independently optionally substituted with one or more groups selected from halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, $-NO_2$, $-N(R^{11})_2$, $-CN$, $-SCN$, $-N_3$, $=O$, $-C(=O)R^9$, $-C(=O)OR^9$, $-N(R^9)C(=O)R^9$, and $-OR^9$, wherein each $C_{1-10}$alkyl, $C_{1-10}$haloalkyl, $C_{2-10}$alkenyl and $C_{2-10}$alkynyl is optionally substituted with one or more $R^{10}$.

In the above Formula (1), $R^{19}$ to $R^{24}$ may be each independently optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$. In some embodiments, each of $R^{19}$ and $R^{24}$ may be independently optionally substituted with one or more groups selected from $C_{1-10}$alkyl, $OC_{1-10}$alkyl, $-NH_2$, $-OH$, $-COOH$, $-C(=O)OC_{1-6}$alkyl. In one embodiment, each of $R^{19}$ and $R^{24}$ are unsubstituted (i.e. 'substituted' with H).

In the above Formula (1), each of $L^1$, $L^2$ and $L^3$ may be independently optionally substituted with one or more groups selected from $R^8$. In some embodiments, each of $L^1$, $L^2$ and $L^3$ may be independently optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$. In some embodiments, each of $L^1$, $L^2$ and $L^3$ may be independently optionally substituted with one or more groups selected from $C_{1-10}$alkyl, $OC_{1-10}$alkyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$. In some embodiments, each of $L^1$, $L^2$ and $L^3$ may be independently optionally substituted with one or more groups selected from $C_{1-10}$alkyl, $OC_{1-10}$alkyl, $-NH_2$, $-OH$, $-COOH$, $-C(=O)OC_{1-6}$alkyl. In one embodiment, each of $L^1$, $L^2$ and $L^3$ may be independently optionally substituted with one or more $-NH_2$, $-OH$ or $-COOH$. In one embodiment, each of $L^1$, $L^2$ and $L^3$ may be independently optionally substituted with one or more -COOH.

In the above Formula (1), each of $L^1$, $L^2$ and $L^3$ may each be independently optionally substituted with one or more groups selected from $R^8$. In some embodiments, each of $L^1$, $L^2$ and $L^3$ may be independently optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$. In some embodiments, $L^1$ and $L^2$ may each be independently optionally substituted with one or more groups selected from $C_{1-10}$alkyl, $OC_{1-10}$alkyl, $-N(R^9)_2$, $-C(=O)N(R^9)_2$, $-OR^9$, $-OC(=O)R^9$, $-C(=O)R^9$, $-C(=O)OR^9$, and $-N(R^9)C(=O)R^9$. In some embodiments, $L^1$ and $L^2$ may each be independently optionally substituted with one or more groups selected from $C_{1-10}$alkyl, $OC_{1-10}$alkyl, $-NH_2$, $-OH$, $-COOH$, $-C(=O)OC_{1-6}$alkyl. In one embodiment, each of $L^1$, $L^2$ and $L^3$ may be independently optionally substituted with one or more $-NH_2$, $-OH$ or $-COOH$. In one embodiment, $L^1$ and $L^2$ may each optionally substituted with one or more $-COOH$.

In one embodiment, $L^1$ is $-C_{1-20}$alkyl- which is uninterrupted or interrupted with one or more groups selected from $-O-$, $-S-$, $-C(=O)-$, $-C(=O)NH-$, $-NH-$, $-C(=O)O-$, $-C(=O)S-$, $-S(=O)_2-$, $-NHC(=S)NH-$, and $-NHC(=O)NH$, and is optionally substituted with one or more groups selected from $C_{1-10}$alkyl, $OC_{1-10}$alkyl, $-NH_2$, $-OH$, $-COOH$, and $-C(=O)OC_{1-6}$alkyl. In one embodiment, $L^1$ is $-C_{1-20}$alkyl- interrupted with one or more $-C(=O)NR^3-$ (e.g. $-C(=O)NH-$) amide bonds, and is optionally substituted with one or more groups selected from $C_{1-10}$alkyl, $OC_{1-10}$alkyl, $-NH_2$, $-OH$, $-COOH$, $-C(=O)OC_{1-6}$ alkyl. In one embodiment, $L^1$ is $-C_{1-20}$alkyl- interrupted with one or more $-C(=O)NR^3-$ (e.g. $-C(=O)NH-$) amide bonds, and is optionally substituted with one or more groups selected from $-NH_2$, $-OH$, or $-COOH$. In one embodiment, $L^1$ is $-C_{1-20}$alkyl-interrupted with one or more $-C(=O)NR^3-$ (e.g. $-C(=O)NH-$) amide bonds, and is optionally substituted with one or more $-COOH$.

In one embodiment, $L^2$ is —$C_{1-20}$alkyl- which is uninterrupted or interrupted with one or more groups selected from —O—, —S—, —C(=O)—, —C(=O)NH—, —NH—, —C(=O)O—, —C(=O)S—, —S(=O)$_2$—, —NHC(=S)NH—, and —NHC(=O)NH, and is optionally substituted with one or more groups selected from $C_{1-10}$alkyl, $OC_{1-10}$alkyl, —NH$_2$, —OH, —COOH, and —C(=O)OC$_{1-6}$alkyl. In one embodiment, $L^2$ is —$C_{1-20}$alkyl- optionally substituted with one or more groups selected from $C_{1-10}$alkyl, $OC_{1-10}$alkyl, —NH$_2$, —OH, —COOH, —C(=O)OC$_{1-6}$alkyl. In one embodiment, $L^2$ is —$C_{1-20}$alkyl- optionally substituted with one or more groups selected from —NH$_2$, —OH, or —COOH. In one embodiment, $L^2$ is —$C_{1-20}$alkyl- optionally substituted with one or more —COOH.

In one embodiment, $L^3$ is —$C_{1-20}$alkyl- or —$C_{1-10}$alkyl-, which is uninterrupted or interrupted with one or more groups selected from O—, —S—, —C(=O)—, —C(=O)NH—, —NH—, —C(=O)O—, —C(=O)S—, —S(=O)$_2$—, —NHC(=S)NH—, and —NHC(=O)NH, and optionally substituted with one or more groups selected from $C_{1-10}$alkyl, $OC_{1-10}$alkyl, 3-10 membered carbocyclyl, 3-10-membered heterocyclyl, $C_{1-10}$alkyl-3-10-membered-carbocyclyl, $C_{1-10}$alkyl-3-10-membered-heterocyclyl, —N(R$^9$)$_2$, —C(=O)N(R$^9$)$_2$, —OR$^9$, —OC(=O)R$^9$, —C(=O)R$^9$, —C(=O)OR$^9$, and —N(R$^9$)C(=O)R$^9$, wherein each $C_{1-10}$alkyl, $C_{1-10}$haloalkyl, $C_{2-10}$alkenyl, $C_{2-10}$alkynyl, 3-10 membered-carbocyclyl, and 3-10-membered-heterocyclyl is optionally substituted with one or more $R^{10}$.

Compounds of Formula (1)

In some embodiments, the compound of Formula (1) has a structure selected from the following Formula (1C) to (1H)

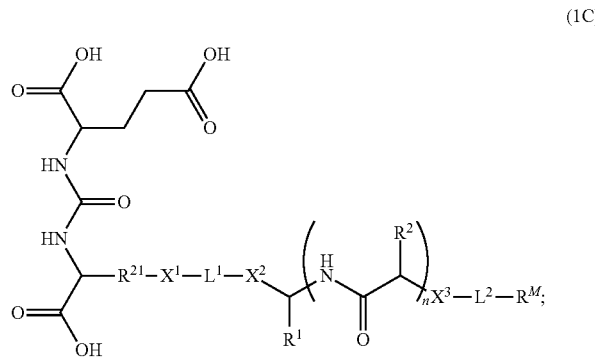
(1C)

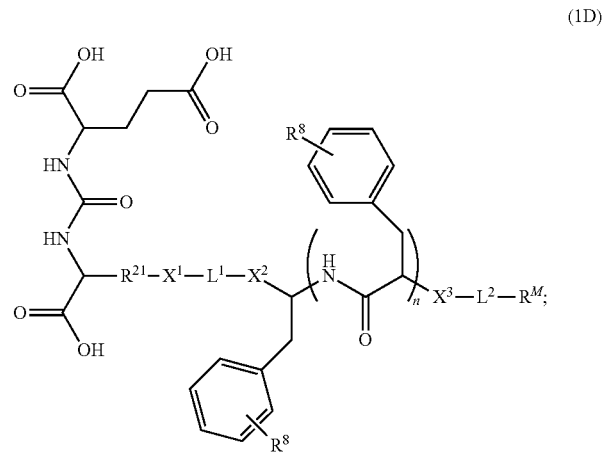
(1D)

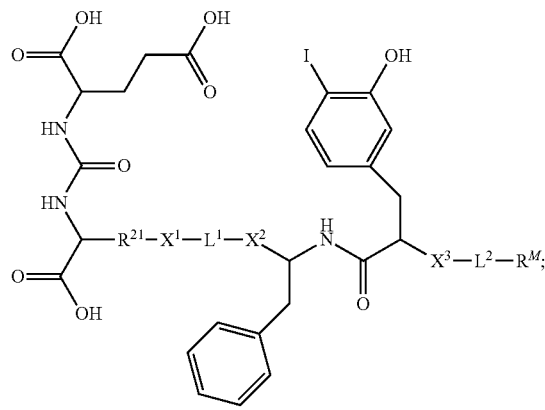
(1E)

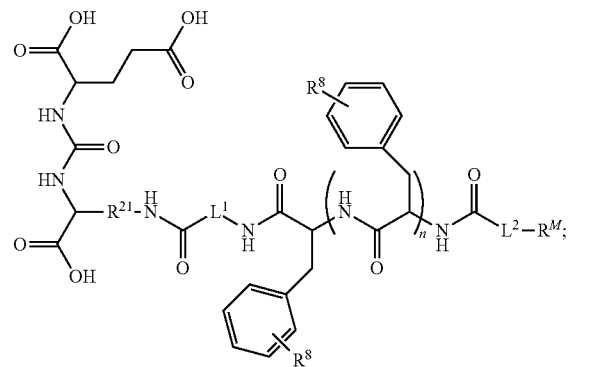
(1F)

(1G)
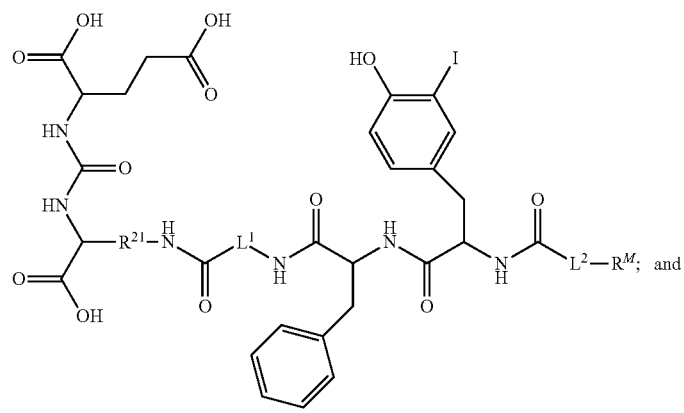
(1H)
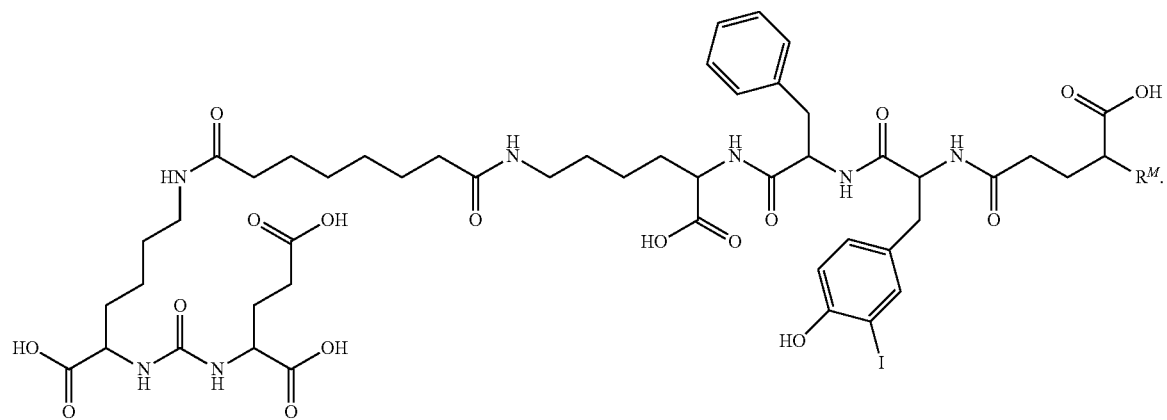
or a pharmaceutically acceptable salt, solvate or stereoisomer thereof;
wherein n, $L^1$, $L^2$, $X^1$, $X^2$, $X^3$, $R^1$, $R^2$, $R^{21}$ and $R^M$ are as described herein.
In some embodiments, the compound of Formula (1) has a structure selected from the following Formula (1I) to (1K):
(1I)
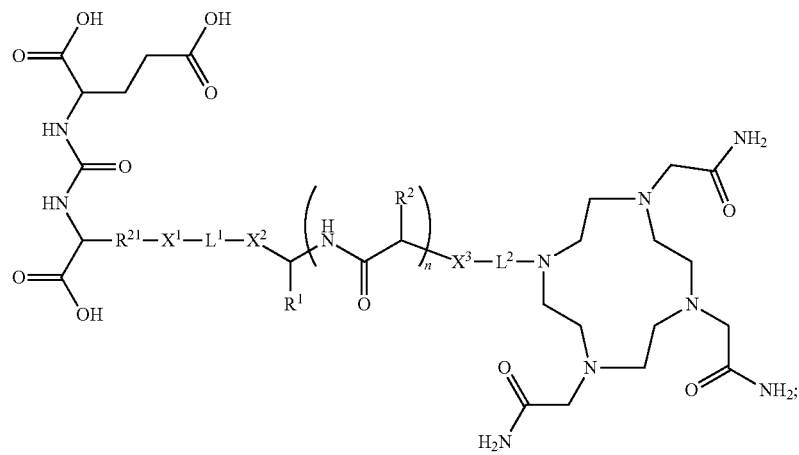

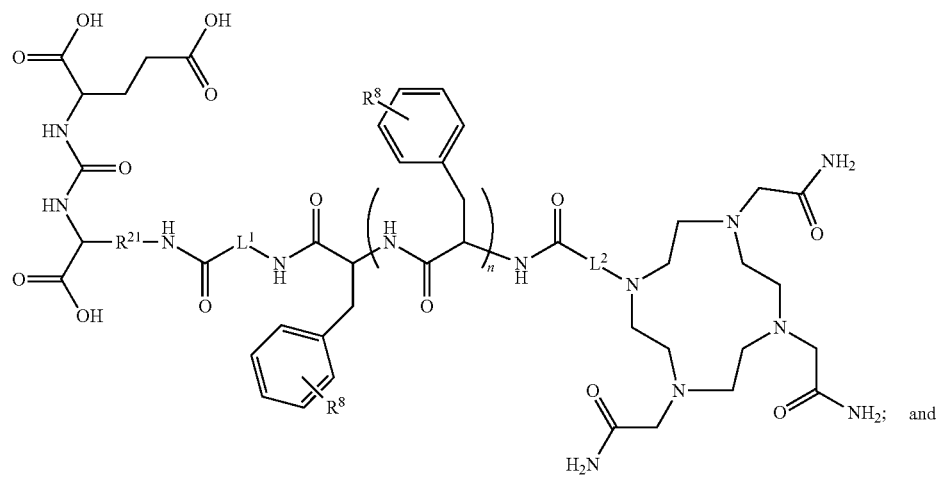
(1J)
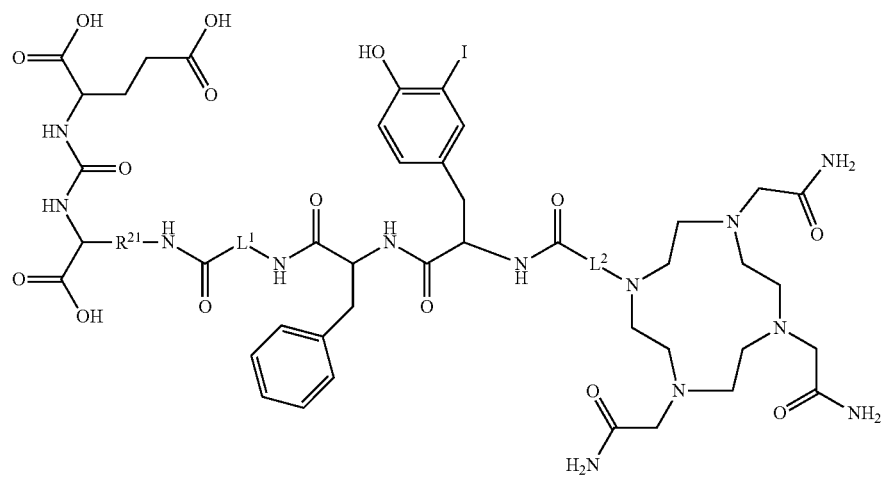
(1K)
or a pharmaceutically acceptable salt, solvate or stereoisomer thereof;
wherein n, $L^1$, $L^2$, $X^1$, $X^2$, $X^3$, $R^1$, $R^2$, $R^{21}$ and $R^M$ are as described herein.
In some embodiments, the compound of Formula (1) has a structure of Formula (1L)
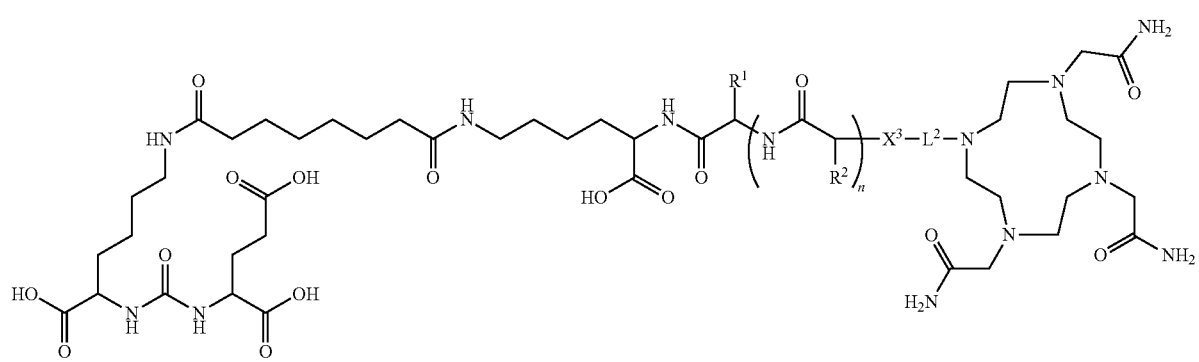
(1L)

or a pharmaceutically acceptable salt, solvate or stereoisomer thereof;
wherein n, $L^2$, $X^3$, $R^1$, and $R^2$ are as described herein.
In one embodiment, the compound of Formula (1) is
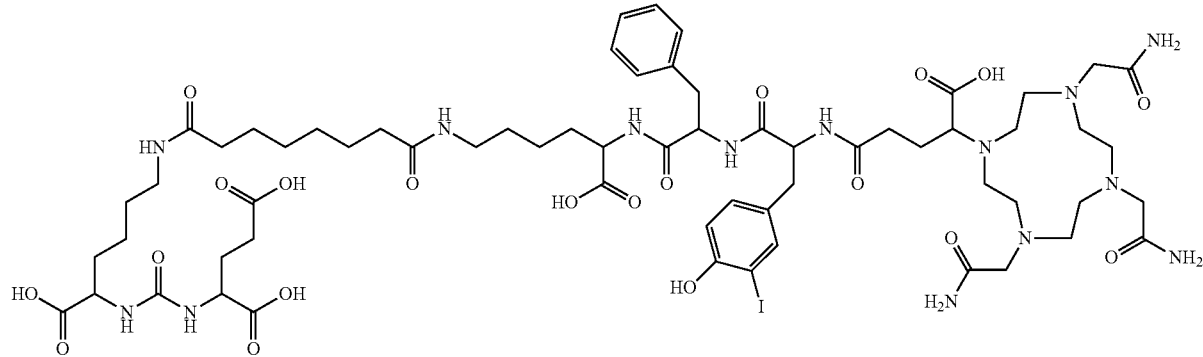 [SMILES: NC(=O)CN1CCN(CC(N)=O)CCN(C(CCC(=O)NC(Cc2ccc(O)c(I)c2)C(=O)NC(Cc2ccccc2)C(=O)NC(CCCCNC(=O)CCCCCCC(=O)NCCCCC(NC(=O)NC(CCC(=O)O)C(=O)O)C(=O)O)C(=O)O)C(=O)O)CCN(CC(N)=O)CC1]
or a pharmaceutically acceptable salt, solvate or stereoisomer thereof.
In some embodiments, the compound of Formula (1) is selected from the group consisting of:
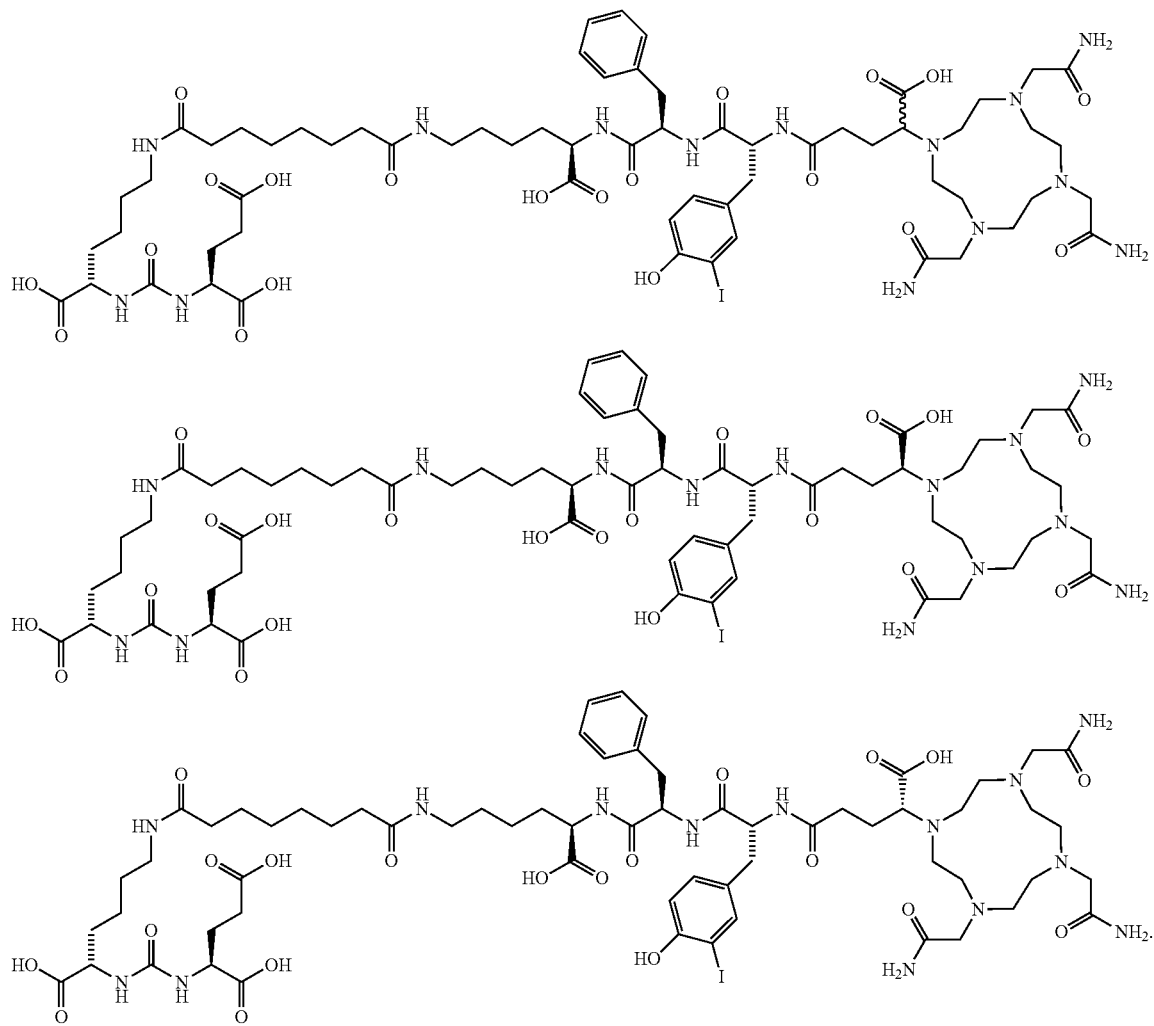

or a pharmaceutically acceptable salt, solvate or stereoisomer thereof.

In some embodiments, the compound of Formula (1) is HO-Glu-CO-Lys[SubA-D-Lys-D-Phe-D-Tyr(3I)-(Pent-$^{212}$Pb-DO3AM)]—OH (chemical name 3S,7S,26S,29R,32R)-29-benzyl-32-(4-hydroxy-3-iodobenzyl)-5,13,20,28,31,34-hexaoxo-37-(4,7,10-tris(2-amino-2-oxoethyl)-1,4,7,10-tetraazacyclododecan-1-yl)-4,6,12,21,27,30,33-heptaazaheptatriacontane-1,3,7,26,37-pentacarboxylic acid) or a pharmaceutically acceptable salt, solvate or stereoisomer thereof.

In some embodiments, the compound of Formula (1) is not:

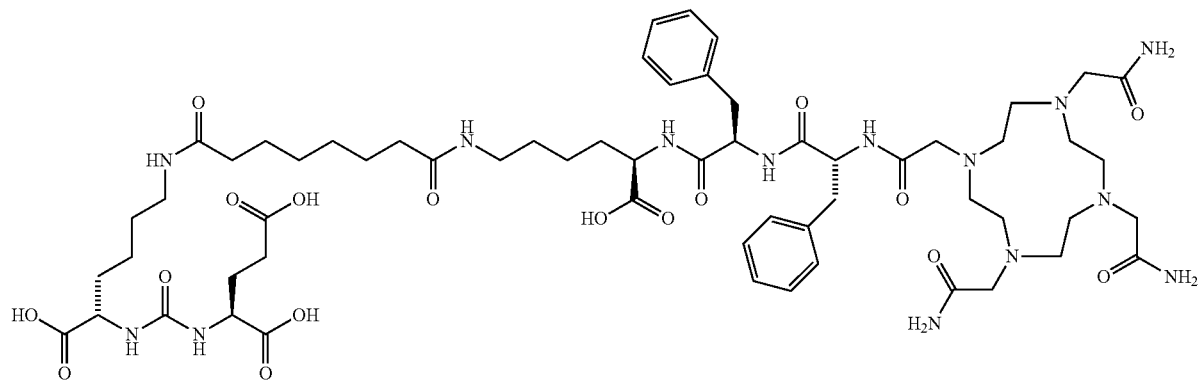 [SMILES: NC(=O)CN1CCN(CC(N)=O)CCN(CC(=O)N[C@H](Cc2ccccc2)C(=O)N[C@H](Cc2ccccc2)C(=O)N[C@H](CCCCNC(=O)CCCCCCC(=O)NCCCC[C@H](NC(=O)N[C@@H](CCC(=O)O)C(=O)O)C(=O)O)C(=O)O)CCN(CC(N)=O)CC1]

or a salt, solvate or stereoisomer thereof.

In some embodiments, the compound of Formula (1) is not:

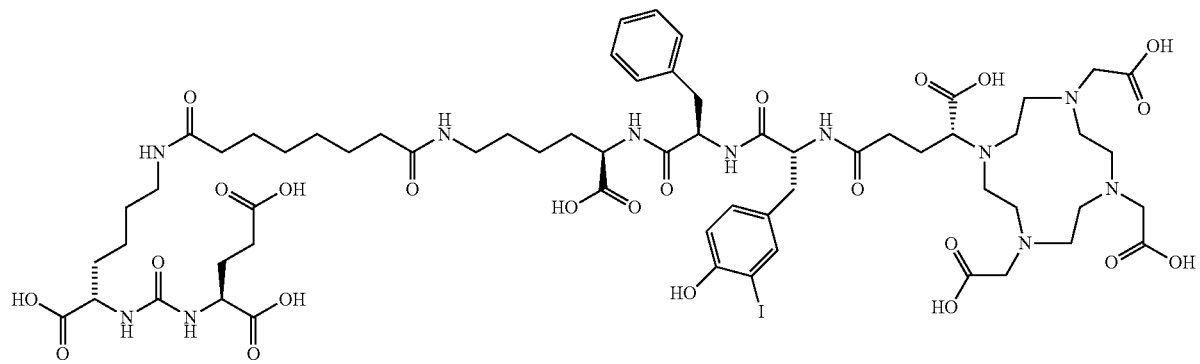 [SMILES: O=C(O)CC[C@H](NC(=O)N[C@@H](CCCCNC(=O)CCCCCCC(=O)NCCCC[C@@H](NC(=O)[C@@H](Cc1ccccc1)NC(=O)[C@@H](Cc1ccc(O)c(I)c1)NC(=O)CC[C@H](C(=O)O)N1CCN(CC(=O)O)CCN(CC(=O)O)CCN(CC(=O)O)CC1)C(=O)O)C(=O)O)C(=O)O]

or a salt, solvate or stereoisomer thereof.

Compositions

Whilst a compound of Formula (1) or a pharmaceutically acceptable salt, solvate, or enantiomer thereof may in some embodiments be administered to a patient in need thereof alone, it is more typically administered as part of a pharmaceutical composition or formulation. Thus, the present disclosure also provides a pharmaceutical composition comprising a compound of Formula (1) or a pharmaceutically acceptable salt, solvate, or enantiomer thereof, and a pharmaceutically acceptable excipient. The pharmaceutical composition comprises one or more pharmaceutically acceptable diluents, carriers or excipients (collectively referred to herein as "excipient" materials).

The present disclosure also provides pharmaceutical compositions, both for veterinary and for human medical use, which comprise compounds of Formula (1) or a pharmaceutically acceptable salt, solvate, or enantiomer thereof, with one or more pharmaceutically acceptable carriers, and optionally any other therapeutic ingredients, stabilisers, or the like. The carrier(s) must be pharmaceutically acceptable in the sense of being compatible with the other ingredients of the formulation and not unduly deleterious to the recipient thereof.

Examples of pharmaceutical compositions include those suitable for parenteral administration, including subcutaneous, intradermal, intramuscular, intravenous, and intraarticular administration. Other less preferred examples of pharmaceutical compositions include those suitable for oral, inhalation, rectal, intraperitoneal and topical administration.

In some embodiments, the pharmaceutical composition comprises the compound of Formula (1) as described herein complexed to a radioisotope (e.g. $^{212}$Pb). In some embodiments, the amount of radioisotope in the composition (in MBq) is at least about 0.1, 1, 5, 10, 20, 30, 40, 50, 60, 70, 80, 90, 100, 120, 150, 200, 300, 400, 500, 600, 800 or 1000. In some embodiments, the amount of radioisotope in the composition (in MBq) is less than about 1000, 800, 600, 500, 400, 300, 200, 150, 120, 100, 90, 80, 70, 60, 50, 40, 30, 20, 10, 5, 1, or 0.1 MBq of radioisotope to the patient. The amount of the radiopharmaceutical may be a range provided by any two of these upper and/or lower values, for example between about 10 MBq to about 500 MBq.

In some embodiments, there is provided a diagnostic composition comprising the compound of Formula (1) or pharmaceutically acceptable salt, solvate, or enantiomer thereof, and a pharmaceutically acceptable carrier.

Therapeutic and Diagnostic Methods and Uses

It has been surprisingly found that compounds of Formula (1) or a pharmaceutically acceptable salt, solvate, stereoisomer thereof, complexed to a radioisotope (such as $^{212}$Pb) show high uptake in PSMA-expressing tumour tissue together with reduced retention in the kidneys following intravenous injection, and in some embodiments demonstrate a much higher tumour to kidney ratio post-injection compared to [$^{212}$Pb]-PSMA-I&T.

Accordingly, there is provided a compound of Formula (1) as described herein, for use in diagnosing, treating and/or preventing a PSMA-expressing cancer.

In some embodiments, there is provided a pharmaceutical composition comprising a compound of Formula (1) as described herein, and a pharmaceutically acceptable excipient.

In another embodiment, there is provided a method for treating and/or preventing a PSMA-expressing cancer in a subject in need thereof, comprising administering a therapeutically effective amount of a compound of Formula (1) as described herein or a pharmaceutical composition as described herein to the subject.

In another embodiment, there is provided use of a compound of Formula (1) as described herein or a pharmaceutical composition as described herein for treating and/or preventing a PSMA-expressing cancer.

In another embodiment, there is provided use of a compound of Formula (1) as described herein or a pharmaceutical composition as described herein in the manufacture of a medicament for treating and/or preventing a PSMA-expressing cancer.

In one embodiment, the PSMA-expressing cancer is selected from the group consisting of prostate cancer, conventional renal cell cancers, cancers of the transitional cells of the bladder, testicular-embryonal cancers, neuroendocrine cancers, colon cancers, brain tumours and breast cancers. In particularly preferred examples, said PSMA-expressing cancer is prostate cancer or breast cancer, in particular prostate cancer. In one example, the PSMA-expressing cancer may be metastatic castrate-resistant prostate cancer (mCRPC).

The amount of the compound of Formula (1) or a pharmaceutically acceptable salt, solvate, or enantiomer thereof that is required to achieve a therapeutic effect will, of course, vary with the particular compound, complexed radioisotope, the route of administration, the subject under treatment, including the type, species, age, weight, sex, and medical condition of the subject being treated, the renal and hepatic function of the subject, and the particular condition, disorder or disease being treated, as well as its severity. An ordinary skilled physician or clinician can readily determine and prescribe the effective amount of the drug required to prevent or treat the condition, disorder or disease.

Dosages of a compound Formula (1), or a pharmaceutically acceptable salt, solvate, or enantiomer thereof, when used for the indicated effects, may range between, for example, about 0.01 mg per kg of body weight per day (mg/kg/day) to about 1000 mg/kg/day. In one embodiment, the dosage of a compound of Formula (1), or a pharmaceutically acceptable salt, solvate, or enantiomer thereof, is between about 0.01 and 1000, 0.1 and 500, 0.1 and 100, 1 and 50 mg/kg/day. In one embodiment, the dosage of a compound of Formula (1), or a pharmaceutically acceptable salt, solvate, or enantiomer thereof, is between about 0.01 and 1000 mg/kg/day. In one embodiment, the dosage of a compound of Formula (1), or a pharmaceutically acceptable salt, solvate, or enantiomer thereof, is between about 0.1 and 100 mg/kg/day. In one embodiment, the dosage of a compound of Formula (1), or a pharmaceutically acceptable salt, solvate, or enantiomer thereof, is greater than about 0.01, 0.1, 1, 10, 20, 50, 75, 100, 500, 1000 mg/kg/day. In one embodiment, the dosage of a compound of Formula (1), or a pharmaceutically acceptable salt, solvate, or enantiomer thereof, is greater than about 0.01 mg/kg/day. In one embodiment, the dosage of a compound of Formula (1), or a pharmaceutically acceptable salt, solvate, or enantiomer thereof, is less than about 5000, 1000, 75, 50, 20, 10, 1, 0.1 mg/kg/day. In one embodiment, the dosage of a compound of Formula (1), or a pharmaceutically acceptable salt, solvate, or enantiomer thereof, is less than about 1000 mg/kg/day.

A compound of Formula (1), or a pharmaceutically acceptable salt, solvate, or enantiomer thereof, may for example be administered as a single daily dose, or otherwise the total daily dosage may be administered in divided doses of two, three, or four times daily. In one embodiment, the compound of Formula (1), or a pharmaceutically acceptable salt, solvate, or enantiomer thereof, may be dosed less frequently than once per day, for example once per two days, three days, four days, five days, six days, or once per week. If administered intravenously, an infusion of the compound of Formula (1) over a period of time may be used, for example, and may include a dose escalation.

In one embodiment, a radiopharmaceutical comprising the compound of Formula (1) complexed to a radioisotope (e.g. $^{212}$Pb) is administered to the patient in need thereof (e.g. via intravenous injection) in an amount effective to prevent and/or treat prostate cancer. In one embodiment, a radiopharmaceutical comprising the compound of Formula (1) complexed to a radioisotope (e.g. $^{212}$Pb) is administered to the patient in need thereof in an amount effective to deliver between about 0.1 MBq to about 1000 MBq of radioisotope to the patient. In one embodiment, a radiopharmaceutical comprising the compound of Formula (1) complexed to a radioisotope (e.g. $^{212}$Pb) is administered to the patient in need thereof in an amount effective to deliver at least about 0.1, 1, 5, 10, 20, 30, 40, 50, 60, 70, 80, 90, 100, 120, 150, 200, 300, 400, 500, 600, 800 or 1000 MBq of radioisotope to the patient. In one embodiment, a radiopharmaceutical comprising the compound of Formula (1) complexed to a radioisotope (e.g. $^{212}$Pb) is administered to the patient in need thereof in an amount effective to deliver less than about 1000, 800, 600, 500, 400, 300, 200, 150, 120, 100, 90, 80, 70, 60, 50, 40, 30, 20, 10, 5, 1, or 0.1 MBq of radioisotope to the patient. The amount of the radiopharmaceutical administered to the patient may be a range provided by any two of these upper and/or lower values, for example between about 10 MBq to about 500 MBq of radioisotope per patient.

In some embodiments, the patient being administered a radiopharmaceutical comprising the compound of Formula (1) complexed to a radioisotope (e.g. $^{212}$Pb) may remain radioactive following administration (e.g. have levels of radioisotope at or above the threshold considered to be radioactive by a medical practitioner) for between about 1 hours to about 96 hours. In some embodiments, the patient being administered a radiopharmaceutical comprising the compound of Formula (1) complexed to a radioisotope may remain radioactive following administration (in hours) for at least about 1, 2, 3, 4, 5, 6, 8, 10, 12, 24, 48, 72, 96 or 120. In some embodiments, the patient being administered a radiopharmaceutical comprising the compound of Formula (1) complexed to a radioisotope may remain radioactive following administration (in hours) for at least about 120, 96, 72, 48, 24, 12, 10, 8, 6, 5, 4, 3, 2 or 1. The patient may remain radioactive for a period of time in a range provided by any two of these upper and/or lower values, for example between about 1 to 24 hours, or between about 1 to 12 hours.

In some embodiments, the PSMA-expressing tumour uptake of the radiopharmaceutical comprising the compound of Formula (1) complexed to a radioisotope (e.g. $^{212}$Pb) following administration (in % ID/g at 24 hours post injection) may be at least about 0.1, 1, 2, 3, 4, 5, 6, 7, 8, 9, 10, 12, 15, 20 or 50. In some embodiments, the PSMA-expressing tumour uptake of the radiopharmaceutical comprising the compound of Formula (1) complexed to a radioisotope following administration (in % ID/g at 24 hours post injection) may be less than about 50, 20, 15, 12, 10, 9, 8, 7, 6, 5, 4, 3, 2, 1 or 0.1. The % ID/g uptake of the radiopharmaceutical may be a range provided by any two of these upper and/or lower values, for example between about 1 to about 20% ID/g at 24 hours post injection.

In some embodiments, the kidney clearance of the radiopharmaceutical comprising the compound of Formula (1) complexed to a radioisotope (e.g. $^{212}$Pb) following administration (in % ID/g at 24 hours post injection) may be at less than about 20, 15, 12, 10, 9, 8, 7, 6, 5, 4, 3, 2, 1, 0.5, 0.1, 0.01 or 0.001. The % ID/g kidney clearance of the radiopharmaceutical may be a range provided by any two of these upper and/or lower values, for example between about 0.01 to about 5% ID/g at 24 hours post injection.

In some embodiments, the compound of Formula (1) may be complexed to a radioisotope suitable for use as an imaging agent. For example, the compound of Formula (1) may be complexed to a positron-emitting radioisotope, such as $^{68}$Ga, $^{64}$Cu, $^{55}$Co or $^{89}$Zr, to provide an imaging agent that can be used as a positron emission tomography (PET) imaging agent. Alternatively, the compound of Formula (1) may be complexed to a gamma-emitting radioisotope, such as $^{203}$Pb, to provide an imaging agent that can be used as a single photon emission computed tomography (SPECT) imaging agent.

In one embodiment, there is provided an imaging agent comprising the compound of Formula (1) as described herein. In one embodiment, $R^M$ is complexed to a radioisotope. In one embodiment, $R^M$ is complexed to a positron-emitting radioisotope, thus providing a positron emission tomography (PET) imaging agent. In one embodiment, the compound is complexed to a radioisotope. In one embodiment, the compound is complexed to a positron-emitting radioisotope, thus providing a positron emission tomography (PET) imaging agent.

As used herein, a "positron emitting radioisotope" refers to radioisotopes that are neutron deficient and achieve stability through nuclear transmutation of a proton into a neutron, leading to emission of a positron (p+) and an electron neutrino (ve). The positron then combines with a nearby electron resulting in the simultaneous emission of two identifiable gamma rays in opposite directions. These can be detected by a PET scanner/multiheaded gamma camera and give very precise indications of their origin. In one embodiment, the positron-emitting radioisotope is selected from the group consisting of $^{68}$Ga, $^{64}$Cu, $^{55}$Co and $^{89}$Zr.

As used herein, a "gamma-emitting radioisotope" refers to radioisotopes that emit gamma radiation, which can be measured directly, in contrast to the positron-emitting radioisotope which emit positrons that annihilate with nearby electrons, causing two gamma photons to be emitted in opposite directions for detection by a gamma camera.

In one embodiment, there is also provided a diagnostic composition comprising the imaging agent described herein and a pharmaceutically acceptable excipient.

In one embodiment, there is provided a method of imaging a tissue in a subject, comprising administering a diagnostically effective amount of the compound of Formula (1), imaging agent or diagnostic composition described herein to the subject.

In another embodiment, there is provided use of a compound of Formula (1), imaging agent or diagnostic composition described herein for imaging a tissue in a subject. In another embodiment, there is provided use of the compound of Formula (1), imaging agent or diagnostic composition described herein in the manufacture of an imaging agent for imaging a tissue in a subject.

In another embodiment, there is provided an ex-vivo method of imaging a tissue sample comprising a diagnostically effective amount of the compound of Formula (1), imaging agent or diagnostic composition described herein.

Imaging may be carried out in the normal manner, for example by injecting a sufficient amount of the imaging composition to provide adequate imaging and then scanning with a suitable imaging or scanning machine, such as a tomograph or gamma camera. In certain embodiments, a method of imaging a region in a patient includes the steps of: (i) administering to a subject a diagnostically effective amount the imaging agent, exposing a region of the subject to the scanning device; and (ii) obtaining an image of the region of the subject.

In some embodiments, the tissue being imaged is a PSMA-expressing tumour tissue. In one embodiment, the PSMA-expressing tumour tissue is prostate cancer, preferably metastatic castrate-resistant prostate cancer (mCRPC).

In one embodiment, there is provided a positron emission tomography (PET) imaging comprising the compound of Formula (1) as described herein, wherein $R^M$ or the compound of Formula (1) is complexed to a positron-emitting radioisotope, e.g. $^{68}$Ga, 25 $^{64}$Cu, $^{55}$Co or $^{89}$Zr.

In some embodiments, there is provided a method of imaging a tissue in a subject, such as PSMA-expressing tumour tissue, comprising contacting the tissue with a PET imaging agent comprising the compound of Formula (1) as described herein complexed to a positron-emitting radioisotope e.g. $^{68}$Ga, $^{64}$Cu, $^{55}$Co or $^{89}$Zr.

In some embodiments, there is provided a method of imaging a tissue in a subject, such as PSMA-expressing tumour tissue, comprising contacting the tissue with a PET imaging agent comprising the compound of Formula (1) as described herein complexed to a positron-emitting radioisotope e.g. $^{68}$Ga, $^{64}$Cu, $^{55}$Co or $^{89}$Zr.

In another embodiment, there is provided use of a PET imaging agent comprising the compound of Formula (1) as described herein complexed to a positron-emitting radioisotope e.g. $^{68}$Ga, $^{64}$Cu, $^{55}$Co or $^{89}$Zr, for imaging a tissue in a subject.

In another embodiment, there is provided use of a PET imaging agent comprising the compound of Formula (1) as described herein complexed to a positron-emitting radioisotope e.g. $^{68}$Ga, 64Cu, $^{55}$Co or $^{89}$Zr, in the manufacture of a PET imaging agent for imaging a tissue in a subject.

In one embodiment, there is provided a single photon emission computed tomography (SPECT) imaging agent comprising the compound of Formula (1) as described herein, wherein $R^M$ is complexed to a gamma-emitting radioisotope e.g. $^{203}$Pb.

In one embodiment, there is provided a single photon emission computed tomography (SPECT) imaging agent comprising the compound of Formula (1) as described herein, wherein the compound of Formula (1) is complexed to a gamma-emitting radioisotope e.g. $^{203}$Pb.

In some embodiments, there is provided a method of imaging a tissue in a subject, such as PSMA-expressing tumour tissue, comprising contacting the tissue with a SPECT imaging agent comprising the compound of Formula (1) as described herein complexed to a gamma-emitting radioisotope e.g. $^{203}$Pb.

In some embodiments, there is provided a method of imaging a tissue in a subject, such as PSMA-expressing tumour tissue, comprising contacting the tissue with a SPECT imaging agent comprising the compound of Formula (1) as described herein complexed to a gamma-emitting radioisotope e.g. $^{203}$Pb.

In another embodiment, there is provided use of a SPECT imaging agent comprising the compound of Formula (1) as described herein complexed to a gamma-emitting radioisotope e.g. $^{203}$Pb, for imaging a tissue in a subject.

In another embodiment, there is provided use of a SPECT imaging agent comprising the compound of Formula (1) as described herein complexed to a gamma-emitting radioisotope e.g. $^{203}$Pb, in the manufacture of a PET imaging agent for imaging a tissue in a subject.

The amount of the imaging agent that is administered to a subject depends on several physiological factors. These factors are known by the physician, including the nature of imaging to be carried out, tissue to be targeted for imaging or therapy and the body weight and medical history of the subject to be imaged or treated using a radiopharmaceutical.

Method of Preparing Compounds of Formula (1)

The present disclosure also provides for a method of preparing a compound of Formula (1) or a salt thereof;

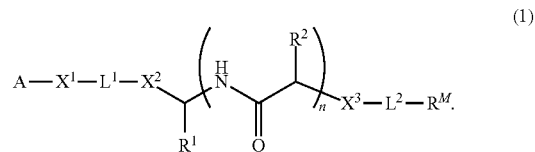

wherein n, A, $L^1$, $L^2$, $X^1$, $X^2$, $X^3$, $R^1$, $R^2$ and $R^M$ are as described herein. It will be appreciated that the embodiments and examples of the compound of Formula (1), including any one of compounds Formula (1A) to (1L), described herein may apply equally to methods described herein.

Any manner of forming a covalent bond between A and $X^1$ or analogues or derivatives thereof, between $X^1$ and $L^1$ or analogues or derivatives thereof, between $L^1$ and $X^2$ or analogues or derivatives thereof, between $X^2$ and the carbon atom to which $R^1$ is attached or analogues or derivatives thereof, between $X^3$ and the carbon atom to which $R^2$ is attached or analogues or derivatives thereof, between $X^3$ and the carbon atom to which $R^1$ is attached or analogues or derivatives thereof (e.g. where n is 0), between $L^2$ and the carbon atom to which $R^2$ is attached or analogues or derivatives thereof (e.g. where $X^3$ is absent), between $L^2$ and the carbon atom to which $R^1$ is attached or analogues or derivatives thereof (e.g. where $X^3$ is absent and n is 0), between $X^3$ and $L^2$ or analogues or derivatives thereof, between $L^2$ and $R^M$ or analogues or derivatives thereof, between $X^3$ and $R^M$ or analogues or derivatives thereof (where $L^2$ is absent), including any intervening heteroatoms, can be utilized in accordance with the present invention. Each covalent bond can be formed by direct conjugation of any of these molecules or analogues or derivatives thereof.

Without intending to limit the scope of the disclosure, covalent bonding can occur through the formation of e.g. amide, ester, ether, thioether, disulfide, imino, sulfonamide groups between e.g. acid, acid chloride, aldehyde, hydroxy, amino, alcohol, alkyl halide, sulfhydryl, or hydrazo groups. Other suitable reactions include, but are not limited to, O-alkylation (etherification); N-alkylation; C-alkylation; chiral alkylation; S-alkylation; esterification; transesterification; displacement (e.g., with cyanide, hydroxide, fluoride, thiocyanate, cyanate, iodide, sulfide, sulfite, azide, nitrite, or nitrate); other nucleophilic aliphatic and aromatic substitutions; oxidation; hydrolysis; epoxidation and chiral epoxidation; Michael addition; aldol condensation; Wittig condensation; Darzens condensation; carbene reactions; thiophosphorylation; reduction; carbonylation; transition metal co-catalysis; HC/HBr/HOCl/$H_2SO_4$ reactions. The person skilled in the art will appreciate that the suitability of a reaction for forming a covalent bond will depend upon the selection of n, A, $L^1$, $L^2$, $X^1$, $X^2$, $X^3$, $R^1$, $R^2$ and $R^M$, as well the functional groups present in any synthetic intermediate. The person skilled in the art will appreciate that a number of synthetic methods are available for the syntheses of A, $L^1$, $L^2$, $X^1$, $X^2$, $X^3$, $R^1$, $R^2$, $R^M$ and analogous or derivatives thereof, or that in many cases, such molecules may be available commercially. Suitable examples may include, but not limited to, amino acids, peptides, amino alcohols, polyethylylene glycols, alkanes, alkenes, alkynes, azide aromatic compounds, carbohydrates, carboxylic acids, esters, organophosphorus compounds, and sulfonates.

The person skilled in the art will appreciate that the overall synthetic method, and any particular reaction or step therein, can be chosen depending upon the selection of the variables n, A, $L^1$, $L^2$, $X^1$, $X^2$, $X^3$, $R^1$, $R^2$ and $R^M$ which may include optional substituent and/or interruption, as is described herein. Non-limiting examples of suitable bond forming reactions are described in Richard C. Larock (ed), 'Comprehensive Organic Transformations: A Guide to Functional Group Preparations,' 4th edition, John Wiley & Sons (2018), and in Theodora E. Greene and Peter G. M. Wuts, 'Protective Groups in Organic Synthesis,' 2nd edition, John Wiley & Sons, Inc. New York (1991), the contents of which are incorporated herein in their entirety.

In one embodiment, the method is for the preparation of a compound of Formula (1L)

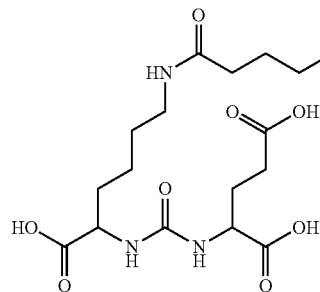
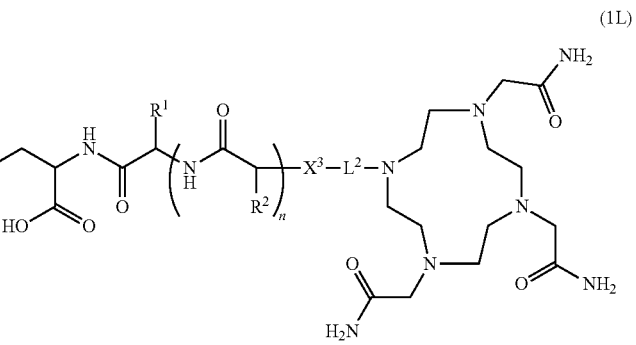

(1L)

or a salt, solvate or stereoisomer thereof;

wherein n, $L^2$, $X^3$, $R^1$, and $R^2$ are as described herein.

It will be appreciated that synthesis of compounds of Formula (1L) may be achieved by one or more coupling steps. A person skilled in the art will appreciate that each amide bond present in compounds of Formula (1L) may be formed via an amide bond forming reaction between an activated carboxylic acid, acid chloride, or mixed anhydride, and an amine. As per above, any manner of forming a covalent bond between $X^3$ and either the carbon atom to which $R^2$ is attached or the carbon atom to which $R^1$ is attached (where n is 0) can be utilized. Moreover, where $X^3$ is absent, any manner of forming a covalent bond between $L^2$ and either the carbon atom to which $R^2$ is attached or the carbon atom to which $R^1$ is attached (where n is 0) can be utilized. Any manner of forming a covalent bond between $L^2$ and the cyclic N can be utilized. Where $L^2$ is absent, any manner of forming a covalent bond between $X^3$ and the cyclic N can be utilized.

In some embodiments at least one, two, three, four, five, or six or more of the coupling steps are amide couplings. It will also be appreciated that synthesis of compounds of Formula (1L) may further require one, two, three, four, or five or more deprotection steps. A deprotection step comprises the removal of at least one protecting group. In some embodiments, the deprotection step comprises removal of at least one Fmoc group. In some embodiments, the deprotection step comprises removal of at least one Dde group. The one or more coupling steps and one or more deprotection steps may be performed as a series of solution phase reactions, a series of reactions performed on a solid support (i.e where at least one of the reactants in each step is supported on a resin), or a combination thereof. In some embodiments, the method is performed at least in part on a solid support. In some embodiments, the method is performed at least in part without a solid support. The term "solid phase" or "solid support" designates any solid material or support to which peptides can be synthesized e.g. via solid-phase peptide synthesis (SPPS). In some embodiments, the method is performed at least in part via solid phase peptide synthesis. In some embodiments, the method is performed at least in part via Fmoc solid-phase peptide synthesis. Solid phase peptide synthesis, including that of compounds of Formula (1L), can be performed either manually, or by using an automated instrument such a peptide synthesiser.

Suitable resins for solid phase synthesis may be selected from the group consisting of chloro- and bromofunctionalized (Merrifield, 4-bromomethylphenoxy)methyl polystyrene, 2-(4-bromomethylphenoxy)ethyl polystyrene, trityl, 2-chlorotrityl chloride, NovaSyn TGT alcohol, NovaSyn TGT bromo), amino- and hydrazine functionalized (AM polystyrene and N-methyl aminomethylpolystyrene, NovaSyn TG amino, MBHA polystyrene, Rink Amide, Siber, amino trityl, sulfamyl-based, WeinrebAM, Fmoc-4-hydrazinobenzoyl, NOVAGel, alkylaminomethyl-indole, hydroxylamine Wang), hydroxyl functionalized (NovSyn hydroxyl, hydroxymethyl-phenyl, oxime), carboxy, aldehyde (benzyloxybenzaldehyde, FMPB AM, FMPB Nova-Gel, NOVAPEG FMBP, FMPE, DFPE, 3-formylindoyl) acetamidomethyl polystyrene-FIA AM resin), enol functionalized (DHP HM resins), thiol functionalized (mercaptomethyl, 3-[4-tritylmercapto)phenylpropionyl AM resins), carbonate functionalized, alkenylcarbonyl functionalized. Resins may be pre-functionalised with one or more amino acids or derivatised amino acids (and may be referred to as a resin-bound derivative), such as those amino acids described herein. In some embodiments, the solid phase is any resin suitable for solid-phase peptide synthesis. In some embodiments, the solid phase is an acid labile resin. In some embodiments, the solid phase is a 2-chlorotrityl chloride resin. In some embodiments, the compound of Formula 1L, precursor or derivative thereof, is linked to the solid support through a 2-chlorotrityl moiety. It will be understood that the solid support is typically loaded with a plurality of the compound of Formula 1L, precursor or derivative thereof.

In some embodiments, one or more coupling steps are performed using standard solid phase peptide-compatible conditions. Suitable Fmoc-compatible conditions are described in Chen, W. C. and White, P. D. 'Fmoc Solid Phase Peptide Sythesis: A Practical Approach' 2000 (Oxford University Press; Hames, B. D. (Ed.)) ISBN 0199637245, the contents of which is incorporated herein by reference in its entirety. Suitable conditions typically include contacting the amine reactant with a carboxyl reactant presented as an appropriately substituted carboxylic acid (typically in an activated form such as acid chloride, mixed anhydride, etc.) or in the presence of one or more coupling reagent(s) suitable for forming an amide bond, such as 1,1-carbonyl-diimidazole (CDI), diisopropylcarbodiimide (DIC), dicyclohexyl carbodiimide (DCC), 1-Ethyl-3-(3-dimethylaminopropyl)carbodiimide (EDC), hydroxybenzotiazole (HOBt), 1-[bis(dimethylamino)methylene]-1H-1,2,3-triazolo[4,5-b]pyridinium 3-oxide hexafluorophosphate (HATU), [benzotriazol-1-yloxy(dimethylamino)methylidene]-dimethylazanium;hexafluorophosphate (HBTU), (benzotriazol-1-yloxy)tripyrrolidinophosphonium hexafluorophosphate (PyBOP) and the like, optionally together with a catalyst such as 4-dimethylaminopyridine (DMAP) or diisopropylethylamine (DIPEA), or ethyl cyano(hydroxyimino)acetate (OxymaPure®) to form an amide bond. In some embodiments, one or more coupling steps are performed with any coupling reagent suitable for forming an amide bond. In some embodiments, one or more coupling steps are performed with CDI, DIC, PyBOP, HBTU or HATU. Suitable solvents include, but are not limited to, DMF, DCM and combinations thereof. The reaction may also be carried out at elevated temperature achieved either through heating (e.g. to a temperature of about 30-70° C.) or through microwave irradiation. The reaction may be also be carried out with constant or periodic agitation. It will be appreciated that independent conditions and reagents may be selected for each coupling step. The contacting of the two reagents may be performed for any particular length of time between 1 minute and 24 hours, which the person skilled in the art will appreciate may be optimised depending on the selection of reaction conditions, reagents, and reactants.

In some embodiments, the one or more coupling steps are performed with a coupling reagent used in molar excess relative to the bound species of at least about 1, 1.1, 1.5, 2.0, 2.5, 5, 10, 15, 20, 25, 50, 100 or 1000 in molar equivalents. In some embodiments, the one or more coupling steps are performed with a catalyst or base used in molar excess relative to the bound species of at least about 1, 1.1, 1.5, 2.0, 2.5, 5, 10, 15, 20, 25, 50, 100 or 1000 in molar equivalents. In some embodiments, coupling reagents, catalysts and bases may be used in molar excess relative to the bound species in a range between any of the above values, for example from about 1 to about 1000 molar equivalents, or about 2 to about 20 molar equivalents.

Optionally, the solid phase synthetic methods described herein may comprise a capping step (for example with an excess acetic anhydride or other activated capping agent) after each coupling step to cap any unprotected sites and prevent synthesis of compounds potentially lacking a single moiety, which may be hard to separate from the desired product.

In some embodiments, the method comprises providing $PG^1$-Lys($PG^2$)—OH or H-Lys($PG^2$)—OH or a salt or resin-bound derivative thereof. In some embodiments, the method comprises a coupling step with $PG^1$-Lys($PG^2$)—OH or H-Lys($PG^2$)—OH or a salt or resin-bound derivative thereof, wherein $PG^1$ and $PG^2$ are independent amine protecting groups. In some embodiments, the $PG^1$-Lys($PG^2$)—OH or H-Lys($PG^2$)—OH is the L-stereoisomer thereof. The term "amine protecting group" as used herein is intended to refer to a group that is capable of being readily removed to provide the corresponding NH or $NH_2$ group of an amine, which and protects the amine group against undesirable reactions that may otherwise occur during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504, the contents of which are incorporated herein by reference in their entirety. Non-limiting examples of amine protecting groups include, acyl and acyloxy groups, for example acetyl, chloroacetyl, trichloroacetyl, o-nitrophenylacetyl, o-nitrophenoxy-acetyl, trifluoroacetyl, acetoacetyl, 4-chlorobutyryl, isobutyryl, picolinoyl, aminocaproyl, benzoyl, methoxy-carbonyl, 9-fluorenylmethoxycarbonyl (Fmoc), 2,2,2-trifluoroethoxycarbonyl, 2-trimethylsilylethoxy-carbonyl, tert-butyloxycarbonyl (BOC), allyloxycarbonyl (alloc), benzyloxycarbonyl, p-nitrobenzyloxycarbonyl, 2,4-dichloro-benzyloxycarbonyl, and the like. Further examples include Cbz (carboxybenzyl), Nosyl (o- or p-nitrophenylsulfonyl), Bpoc (2-(4-biphenyl)isopropoxycarbonyl) and Dde (1-(4,4-dimethyl-2,6-dioxohexylidene)ethyl). In some embodiments $PG^1$ and $PG^2$ are different amine protecting groups. In some embodiments, $PG^1$ is Fmoc. In some embodiments, $PG^2$ is an amine protecting group that can be selectively removed in the presence of an Fmoc protecting group. In some embodiments, $PG^2$ is Dde.

In one embodiment, the method comprises a coupling step with H-Glu($PG^3$)—O-$PG^4$, wherein $PG^3$ and $PG^4$ are independent carboxyl protecting groups. In some embodiments, the H-Glu($PG^3$)—O-$PG^4$ is the L-stereoisomer thereof. The term "carboxyl protecting group" as used herein is intended to refer to a group that is capable of being readily removed to provide the a COOH group, and which protects the carboxyl group against undesirable reactions that may otherwise occur during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Non-limiting examples of carboxyl protecting groups include alkyl and silyl groups, for example methyl, ethyl, tert-, butyl, methoxymethyl, 2,2,2-trichloroethyl, benzyl, diphenylmethyl, trimethylsilyl, and tert-butyldimethylsilyl, and the like. In one embodiment, $PG^3$ and $PG^4$ are the same carboxyl protecting group. In some embodiments, $PG^3$ is tert-Bu. In some embodiments, $PG^4$ is tert-Bu. In some embodiments, $PG^3$ and $PG^4$ are tert-Bu.

In one embodiment, the method comprises a coupling step with suberic acid. In one embodiment, the method comprises a coupling step with $PG^1$-Lys-O-$PG^6$, wherein $PG^5$ is an amine protecting group, and wherein $PG^6$ is a carboxyl protecting group. In some embodiments, the $PG^5$-Lys-O-$PG^6$ is the D-stereoisomer thereof. In some embodiments, $PG^5$ is Fmoc. In some embodiments, $PG^6$ is tert-Bu.

In one embodiment, the method comprises a coupling step with $PG^7$-NH—CH($R^1$)—COOH, wherein $PG^7$ is an amine protecting group, and $R^1$ is as described herein. In some embodiments, the $PG^7$-NH—CH($R^1$)—COOH is the D-stereoisomer thereof. In some embodiments, $PG^7$ is Fmoc. In one embodiment, the method comprises a coupling step with $PG^7$-Phe-OH, wherein $PG^7$ is an amine protecting group.

In one embodiment, the method optionally comprises one or more coupling steps with $PG^8$-NH—CH($R^2$)—COOH, wherein $PG^8$ is an amine protecting group, and $R^2$ is as described herein. In one embodiment, the method comprises one or more coupling steps with $PG^8$-NH—CH($R^2$)—COOH, wherein $PG^8$ is an amine protecting group, and $R^2$ is as described herein. In some embodiments, the $PG^8$-NH—CH($R^2$)—COOH is the D-stereoisomer thereof. In some embodiments, PG⁸ is Fmoc. In one embodiment, the method comprises one or more a coupling steps with PG⁸-3-Iodo-Tyr-OH, wherein PG⁸ is an amine protecting group. It will be appreciated that where the method comprises one or more coupling steps with PG⁸-NH—CH(R²)—COOH, that each coupling step may be followed by a step to remove the PG⁸ protecting group. That is to say, in some embodiments, the method optionally comprises one, two or three coupling steps with PG⁸-NH—CH(R²)—COOH, and optionally comprises one, two or three deprotection steps to remove a PG⁸ protecting group.

In one embodiment, the method comprises a coupling step with a compound of Formula (R-1):

$$RG^1\text{-}L^2\text{-}R^M \qquad (R\text{-}1)$$

wherein $RG^1$ is a reactive coupling group; and $L^2$ and $R^M$ are described herein.

In one embodiment, the method comprises a coupling step with a compound of Formula (S-1):

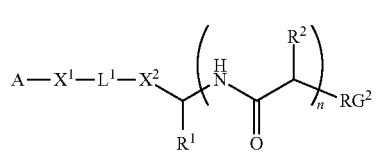

(S-1)

wherein $RG^2$ is a reactive coupling group; and n, A, $X^1$, $L^1$, $X^2$, $R^1$ and $R^2$ are defined herein.

In one embodiment, the compound of Formula (S-1) is optionally attached to a solid support. For example, A may be a solid support derivative thereof. In some embodiments, the compound of Formula (S-1) is attached to a solid support (viz. is a solid supported derivative of Formula S-1). The person skilled in the art will appreciate that a variety of positions may be selected for attachment to the solid support.

It will be understood that a reactive coupling group refers to a functional group that is suitable for performing a coupling step or coupling reaction. It will be understood that a reactive coupling groups will be suitable for performing a coupling with certain other reactive coupling groups, and that a person skilled in the art will be able select an appropriate pair of complementary reactive coupling groups (viz. select a suitable combination of $RG^1$ and $RG^2$ as used herein) with which to perform a coupling step or coupling reaction. Non-limiting examples of suitable reactive coupling groups may include, but are not limited to, epoxides, peroxides, alkyl boranes, halides, thiols, amines, amides, aldehydes, —OH, —COOH, esters, diazo, isocyanates, silanes, phosphorous-containing groups, dithioesters, dithiocarbamates, dithiocarbonates, trithiocarbonates, alkoxyamines, formyl azides, sulfonyl halide, aryl sulfonyl groups (such as aryl sulfonyl halides or aryl sulfonyl azides), phosphoryl azides, vinyls (such as vinyl, alkyl vinyls, vinylidenes, or aryl vinyls), dienes, dyes, porphyrins, alkyl azides, aryl azide, or combinations or derivatives thereof. In some embodiments, $RG^1$ and $RG^2$ are each independently selected from thiols, amines, amides, aldehydes, —OH, —COOH, esters, dithiocarbonate, diazo, or sulfonyl halide. In some embodiments, $RG^1$ and $RG^2$ are each independently selected from amines, amides, aldehydes, —OH, —COOH, esters. In some embodiments, $RG^1$ and $RG^2$ are each independently selected from amines, amides, aldehydes, —OH, —COOH. In some embodiments, $RG^1$ and $RG^2$ are each independently selected from amines and COOH. In some embodiments, $RG^1$ is —COOH, and $RG^2$ is an amine.

In one embodiment, the method comprises coupling a compound of Formula (R-1) with a compound of Formula (S-1). It will be appreciate that $RG^1$ and $RG^2$ couple together (e.g. react together) to form the compound of Formula (1), including any one of compounds Formula (1A) to (1L).

In one embodiment, there is provided a method for preparing a compound of Formula (1), including any one of compounds of Formula (1A) to (1L), or a salt or solid supported derivative thereof, comprising coupling a compound of Formula (R-1) with a compound of Formula (S-1):

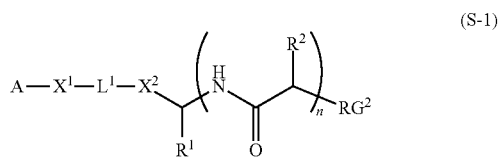

(S-1)

$$RG^1\text{—}L^2\text{—}R^M \qquad (R\text{-}1)$$

wherein:

$RG^1$ and $RG^2$ are each independently a reactive coupling group;

n, A, $X^1$, $L^1$, $X^2$, $R^1$, $R^2$, $L^2$ and $R^M$ are described herein, and wherein the compound of Formula (S-1) is optionally attached to a solid support.

It will be appreciated that the compound of (S-1) and the compound of (R-1) couple together to form the compound of Formula (1), including any one of compounds of Formula (1A) to (1L). In one embodiment, $RG^1$ and $RG^2$ couple together to form $X^3$ in the compound of Formula (1), including any one of compounds of Formula (1A) to (1L). In one embodiment, A is a solid support derivative thereof.

In one embodiment, compound (R-1) has a structure of Formula (R-2):

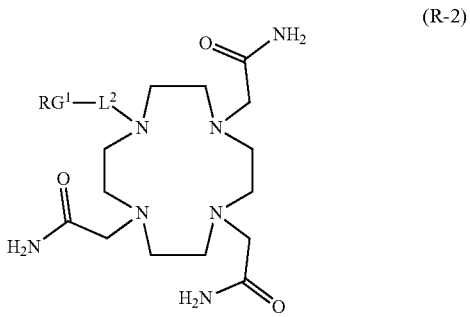

(R-2)

wherein $RG^1$ is a reactive coupling group, and $L^2$ is described herein.

In one embodiment, the compound of (S-1) has a structure of Formula (S-2):

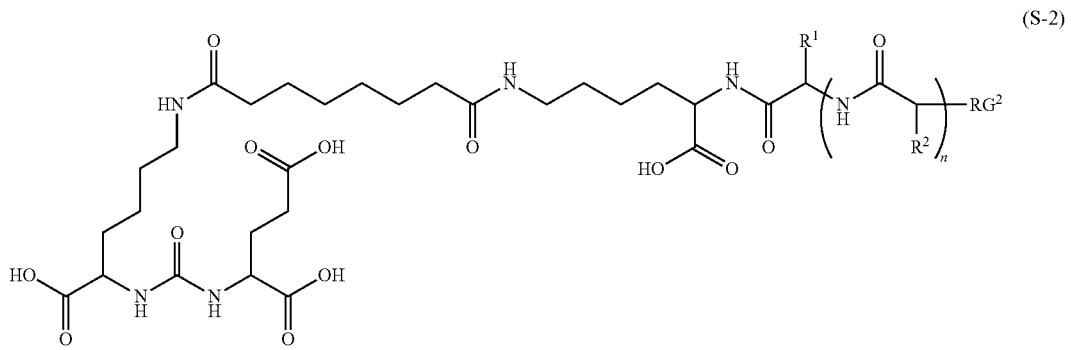

(S-2)

wherein $RG^2$ is a reactive coupling group; and n, $R^1$ and $R^2$ are defined herein.

In some embodiments, the compound of Formula (S-1) is optionally attached to a solid support. In some embodiments, the compound of Formula (S-2) is attached to a solid support (viz. is a solid supported derivative of Formula S-1). The person skilled in the art will appreciate that a variety of positions may be selected for attachment to the solid support. In some embodiments, the compound is attached to the solid support via an amino acid carboxylic acid. In some embodiments, the compound is attached to the solid support via a lysine carboxylic acid.

In one embodiment, there is provided a method of preparing a compound of Formula (1L), or a salt or solid supported derivative thereof, the method comprising coupling a compound of Formula (R-2) with a compound of Formula (S-2):

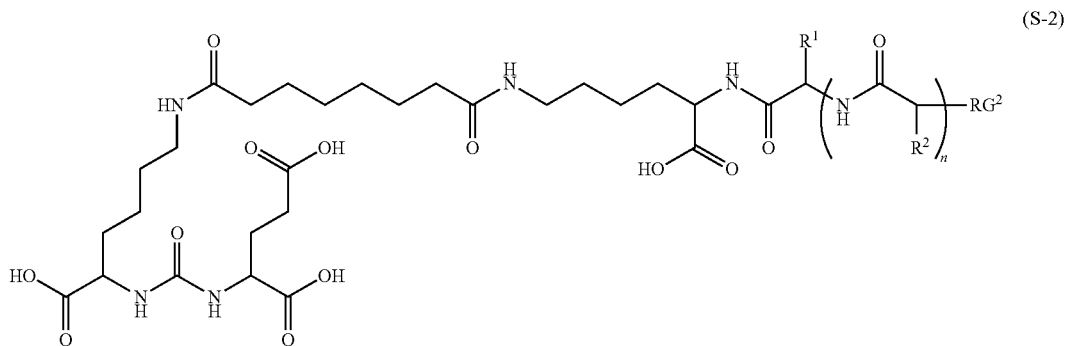

(S-2)

(R-2)

wherein:

RG$^1$ and RG$^2$ are each independently a reactive coupling group; and n, L$^2$, R$^1$ and R$^2$ are described herein, wherein the compound of Formula (S-2) is optionally attached to a solid support.

In one embodiment, the compound of (S-1) has a structure of Formula (S-2A)

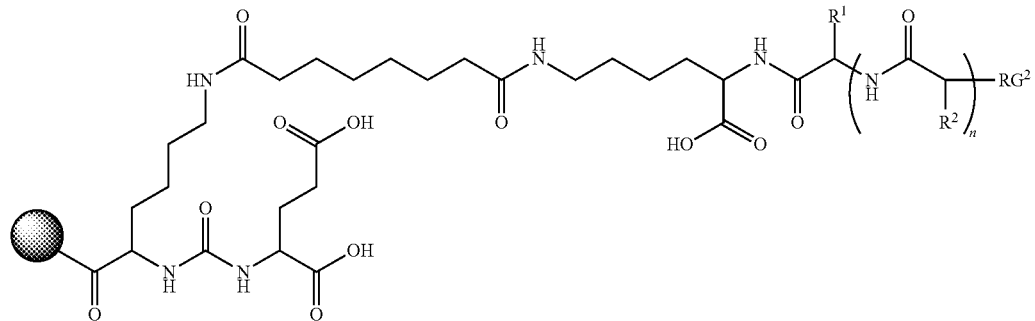

wherein

denotes a solid support,

RG$^2$ is a reactive coupling group, n, R$^1$ and R$^2$ are defined herein.

In one embodiment, there is provided a method for preparing a compound of Formula (1L), or a salt or solid supported derivative thereof, comprising coupling a compound of Formula (R-2) with a compound of Formula (S-2) or (S-2A):

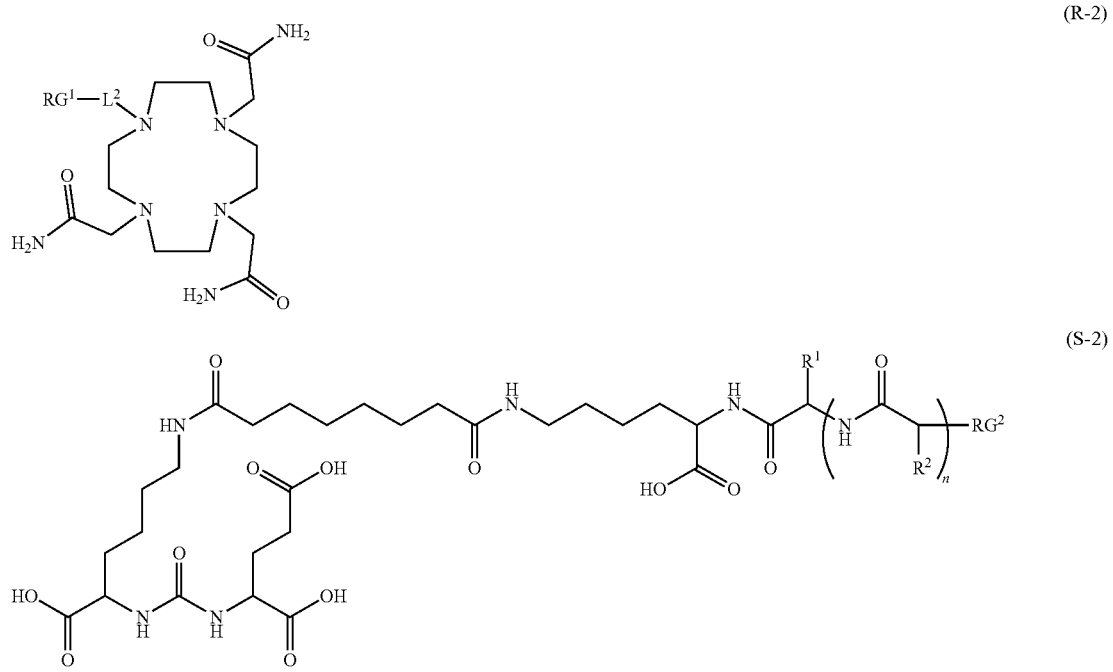

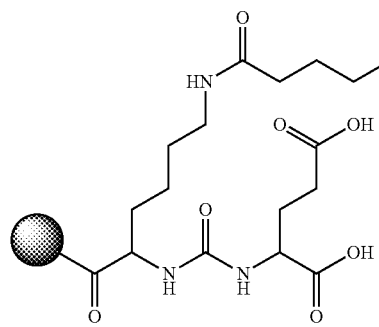

(S-2A)

wherein

   20 denotes a solid support,
$RG^1$ and $RG^2$ are each independently a reactive coupling group,
n, $R^1$, $R^2$ and $L^2$ are defined herein.

It will be appreciated that the compound of (R-2) couples with the compound of (S-2) or (S-2A) to form the compound of Formula (1L). In one embodiment, the coupling forms $X^3$ in the compound of Formula (1L).

In one embodiment, the method comprises a coupling step with a compound selected from the group consisting of Formula (R-3) or (R-4):

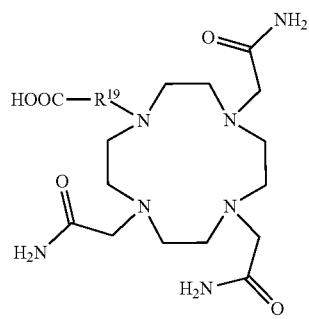

(R-3)

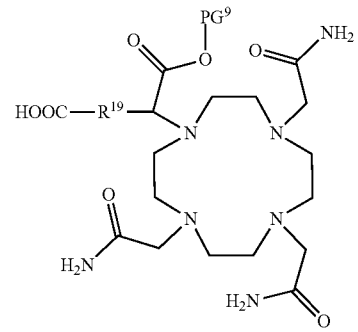

(R-4)

wherein $R^{19}$ is as described herein, and $PG^9$ is a carboxyl protecting group. In some embodiments, $PG^9$ is tert-Bu.

In one embodiment, there is provided a method for preparing a compound of Formula (1L), or a salt or solid supported derivative thereof, comprising coupling a compound of Formula (R-3) with a compound of Formula (S-2) or (S-2A):

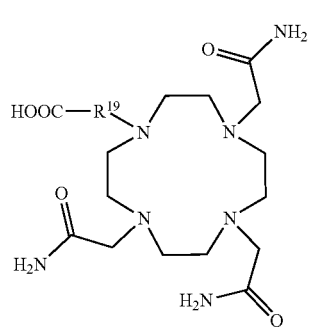

(R-3)

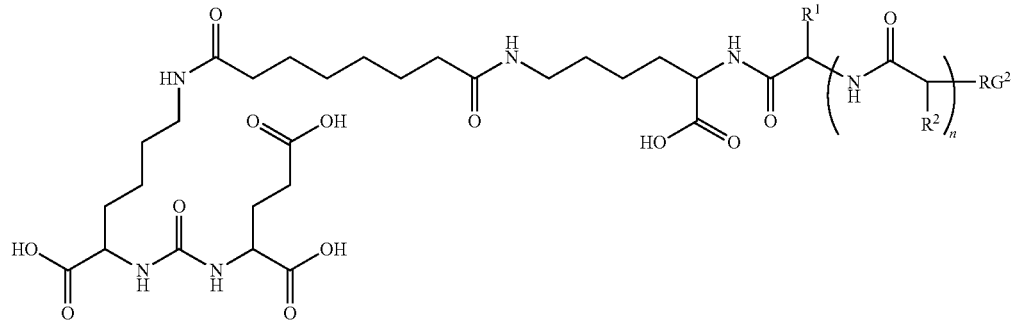

(S-2)

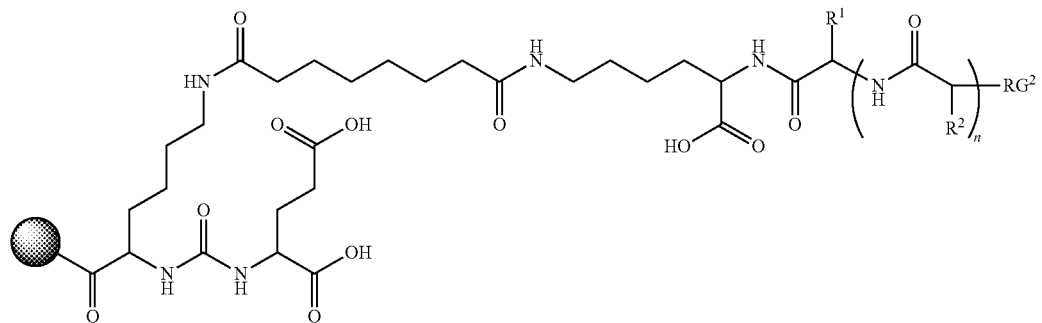

(S-2A)

wherein

denotes a solid support,
$RG^1$ and $RG^2$ are each independently a reactive coupling group,
n, $R^1$, $R^2$ and $R^{19}$ are defined herein.

It will be appreciated that the compound of (R-3) couples with the compound of (S-2) or (S-2A) to form the compound of (Formula (L). In one embodiment, the coupling forms $X^3$ in the compound of Formula (1L).

In one embodiment, there is provided a method for preparing a compound of Formula (1L), or a salt or solid supported derivative thereof, comprising coupling a compound of Formula (R-4) with a compound of Formula (S-2) or (S-2A):

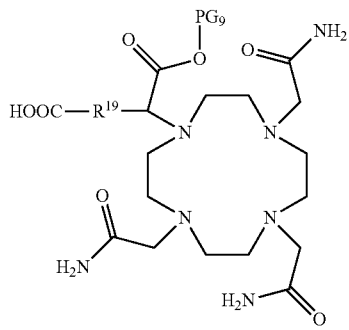

(R-4)

-continued

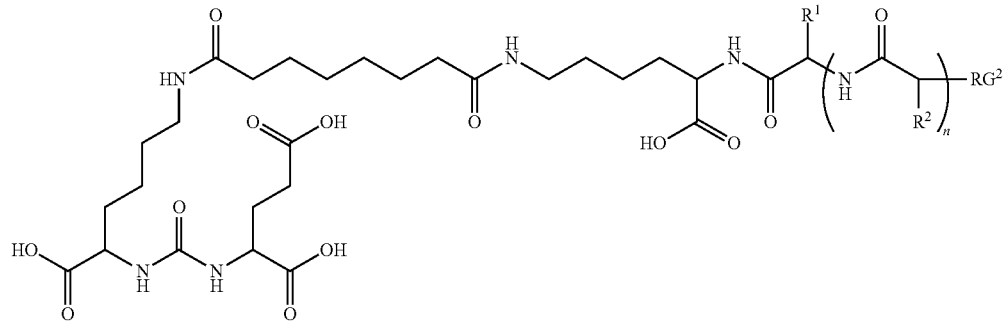
(S-2)

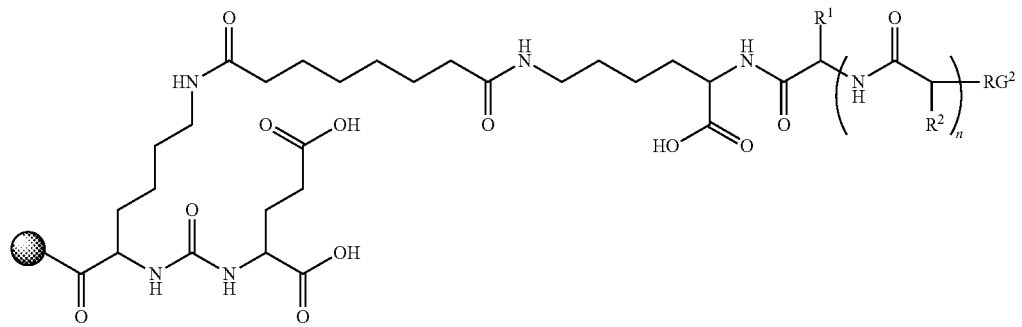
(S-2A)

wherein denotes a solid support,
RG¹ and RG² are each independently a reactive coupling group,
n, $R^1$, $R^2$, $R^{19}$ and $PG^9$ are defined herein.

It will be appreciated that the compound of (R-4) couples with the compound of (S-2) or (S-2A) to form the compound of Formula (1L). In one embodiment, the coupling forms $X^3$ in the compound of Formula (1L).

In one embodiment, the method comprises a coupling step with a compound of Formula (R-5):

(R-5)

wherein $PG^9$ is a carboxyl protecting group. In some embodiments, $PG^9$ is tert-Bu.

In one embodiment, there is provided a method for preparing a compound of Formula (1L), or a salt or solid supported derivative thereof, comprising coupling a compound of Formula (R-5) with a compound of Formula (S-2) or (S-2A):

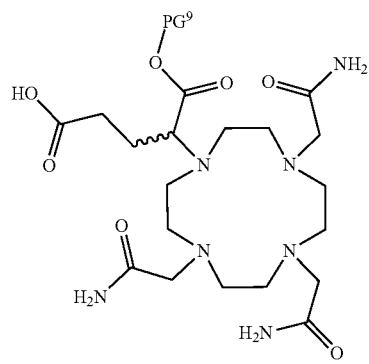

(R-5)

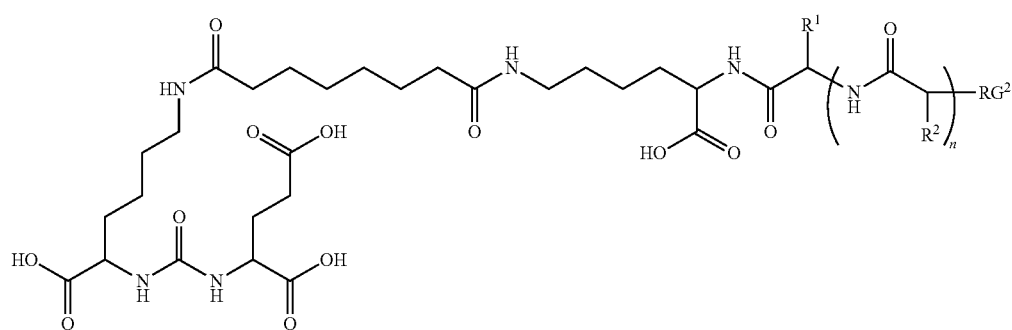

(S-2)

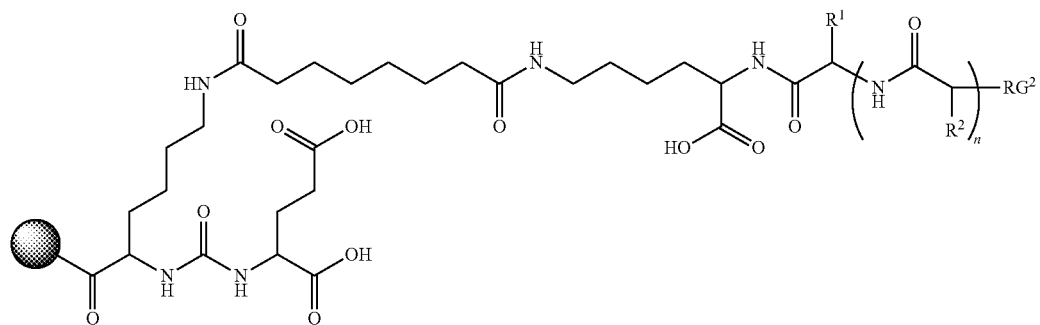

(S-2A)

wherein

denotes a solid support, $RG^1$ and $RG^2$ are each independently a reactive coupling group, n, $R^1$, $R^2$, and $PG^9$ are defined herein.

It will be appreciated that the compound of (R-5) couples with the compound of (S-2) or (S-2A) to form the compound of Formula (1L). In one embodiment, the coupling forms $X^3$ in the compound of Formula (1L).

The person skilled in the art will appreciate that compounds with structures R-1, R-2 R-3, R-4, and R-5 may be readily prepared from DO3AM. The full chemical name of DO3AM is 1,4,7,10-tetraazacyclododecane-1,4,7-triacetamide;2,2',2''-(1,4,7,10-tetraazacyclododecane-1,4,7-triyl)triacetamide. Without intending to limit the scope of any of the aspects, embodiments, or examples described herein, a compound of R-1, R-2, R-3, or R-4 may be prepared by nucleophilic substitution, with e.g. $HOOC-R^{19}-X$, $HOOC-R^{19}-CH(COO-PG^9)X$, or $HOOCCH_2CH_2CH(COO-PG^9)X$, wherein X is a halide (e.g. Br, Cl, and I) and $R^{19}$ is as described according to any aspect, embodiment, or example herein.

Conditions to carry out the deprotection step(s) depend on the selection of the protecting groups, and the desired site of deprotection. Typically, deprotection includes treating the protected compound (which may be bound to a solid support) with an acid, base (e.g. secondary amine, primary amine, piperidine, piperazine, 1,8-diazabicyclo[5.4.0]undec-7-ene), metal-catalyst, or other reactive compound such as hydrazine, for a period of time. The deprotection may also be carried out at elevated temperature achieved either through heating (e.g. to a temperature of about 30-70° C.) or through microwave irradiation. The deprotection may be also be carried out with constant or periodic agitation. There are usually multiple conditions possible to cleave a protecting group and the skilled person will be able to determine appropriate conditions depending on the solid support selected, the protecting group to be removed and the remaining functionality in the compound (including other protecting groups that are present). Selective deprotecting steps require the selection of conditions able to cleave a protecting group in the presence of one or more further protecting groups, e.g. the deprotection of $PG^2$ in the presence of $PG^1$. Accordingly, in some embodiments, $PG^1$ is not the same as $PG^2$. In some embodiments, $PG^1$, $PG^5$, $PG^7$ and $PG^8$ are the same.

In some embodiments, the method comprises removing the $PG^1$ protecting group. In some embodiments, the method comprises removing the $PG^2$ protecting group. In some embodiments, the method comprises removing the $PG^3$ protecting group. In some embodiments, the method comprises removing the $PG^4$ protecting group. In some embodiments, the method comprises removing the $PG^5$ protecting group. In some embodiments, the method comprises removing the $PG^6$ protecting group. In some embodiments, the method comprises removing the $PG^7$ protecting group. In some embodiments, the method comprises removing the $PG^8$ protecting group. In some embodiments, the method comprises one or more steps comprising removing the $PG^8$ protecting group. In some embodiments, the method comprises removing the $PG^9$ protecting group. In some embodiments, removing the $PG^1$, $PG^5$, $PG^7$ or $PG^8$ protecting group comprises contacting the molecule comprising the protecting group with a base. In some embodiments, removing the $PG^1$, $PG^5$, $PG^7$ or $PG^8$ protecting group comprises contacting the molecule comprising the protecting group with a solution comprising piperidine (for example a 20% piperidine solution in DMF). In some embodiments, removing the $PG^2$ protecting group comprises contacting the molecule comprising the protecting group with a solution comprising hyrazine. It will be understood that multiple deprotection steps may be necessary to effect complete removal of a protecting group, and that various methods are known in the art for monitoring completion.

In some embodiments, the method comprises and/or consists of:
(a) providing $PG^1$-Lys($PG^2$)—OH or H-Lys($PG^2$)—OH or a salt thereof or resin-bound derivative thereof;
(b) optionally, removing the $PG^1$ protecting group if present;
(c) coupling to H-Glu($PG^3$)—O-$PG^4$ or salt thereof;
(d) removing the $PG^2$ protecting group;
(e) coupling to suberic acid or salt thereof;
(f) coupling to $PG^1$-Lys-O-$PG^6$ or salt thereof;
(g) removing the $PG^5$ protecting group;
(h) coupling to $PG^7$-NH—CH($R^1$)—COOH or salt thereof;
(i) removing the $PG^7$ protecting group;
(j) optionally, coupling to $PG^8$-NH—CH($R^2$)—COOH or salt thereof;
(k) optionally, removing the $PG^8$ protecting group if present;
(l) optionally, repeating step (j) followed by step (k) once or twice; and
(m) coupling to a compound of R-1, R-2, R-3, R-4, R-5 or salt thereof, wherein $PG^1$, $PG^2$, $PG^3$, $PG^4$, $PG^5$, $PG^6$, $PG^7$, $PG^8$ and $PG^9$ are as described herein.

In some embodiments, the method comprises one, two, three, four, five, six, seven or more of the following steps:
(a) providing $PG^1$-Lys($PG^2$)—OH or H-Lys($PG^2$)—OH or a salt thereof or resin-bound derivative thereof;
(c) coupling to H-Glu($PG^3$)—O-$PG^4$ or salt thereof;
(e) coupling to suberic acid or salt thereof;
(f) coupling to $PG^5$-Lys-O-$PG^6$ or salt thereof;
(h) coupling to $PG^7$-NH—CH($R^1$)—COOH or salt thereof;
(j) coupling to $PG^8$-NH—CH($R^2$)—COOH or salt thereof;
(l) optionally, repeating step (j) once or twice; and
(m) coupling to a compound of R-1, R-2, R-3, R-4, R-5 or salt thereof, wherein $PG^1$, $PG^2$, $PG^3$, $PG^4$, $PG^5$, $PG^6$, $PG^7$, $PG^8$ and $PG^9$ are as described herein.

In some embodiments, the method comprises and/or consists of:
(a) providing $PG^1$-Lys($PG^2$)—OH or H-Lys($PG^2$)—OH or a salt thereof or resin-bound derivative thereof;
(b) optionally, removing the $PG^1$ protecting group if present;
(c) coupling to H-Glu($PG^3$)—O-$PG^4$ or salt thereof;
(d) removing the $PG^2$ protecting group;
(e) coupling to suberic acid or salt thereof;
(f) coupling to $PG^5$-Lys-O-$PG^6$ or salt thereof;
(g) removing the $PG^5$ protecting group;
(h) coupling to $PG^7$-NH—CH($R^1$)—COOH or salt thereof;
(i) removing the $PG^7$ protecting group;
(j) optionally, coupling to $PG^8$-NH—CH($R^2$)—COOH or salt thereof;
(k) optionally, removing the $PG^8$ protecting group if present;
(l) optionally, repeating step (j) followed by step (k) once or twice; and
(m) coupling to a compound of R-1, R-2, R-3, R-4, R-5 or salt thereof;
(n) optionally, cleaving the synthesised peptide from the resin to obtain a crude peptide and optionally, precipitating; and
(o) optionally, purifying the crude peptide to obtain a pure product, wherein $PG^1$, $PG^2$, $PG^3$, $PG^4$, $PG^5$, $PG^6$, $PG^7$, $PG^8$ and $PG^9$ are as described herein.

The person skilled in the art will appreciate that the order in which steps (a) to (o) are performed may be varied, with multiple variations possible to prepare the same desired compound. That is to say, that the order of the coupling steps may be varied, and yet the same compound of Formula (1) or Formula (1A) to (1L) arrived at.

In some embodiments, $PG^1$-Lys($PG^2$)—OH or H-Lys($PG^2$)—OH are bound to a solid support. In some embodiments, providing $PG^1$-Lys($PG^2$)—OH or H-Lys($PG^2$)—OH comprises coupling $PG^1$-Lys($PG^2$)—OH or H-Lys($PG^2$)—OH to a solid support. In some embodiments, providing H-Lys($PG^2$)—OH comprises removing the $PG^1$ protecting group from $PG^1$-Lys($PG^2$)—OH.

In some embodiments, the method comprises one, two, three, four, five, six, seven, eight, nine, ten or more amide coupling steps. In some embodiments, all coupling steps are amide coupling steps.

In some embodiments, the method further comprises cleaving the synthesised peptide from the solid phase carrier or resin to obtain a crude peptide. Thus in some embodiments, the method is for providing a synthesised peptide. Conditions required to cleave the growing compounds from the solid support depend on the solid support selected. Typically, cleavage conditions include exposing the resin, optionally at an elevated temperature, to a composition that comprises an acid (for example, trifluoroacetic acid, also known as TFA) or base, water, and optionally a scavenger (such as triisopropylsilane, also known as TIPS) and/or reducing agent (e.g. such as EDTA or DTT). In some embodiments, the conditions to cleave the compound from the solid support are also capable of global deprotection of any remaining protecting groups within the compound (for example tert-Bu carboxyl protecting groups). The obtained crude peptide may optionally be precipitated from the cleavage mixture e.g. by addition of a solvent such as diethyl ether, and then separated by centrifugation and filtration. The crude peptide may be lyphophilised.

In one embodiment, the method further comprises purifying the crude peptide to obtain a pure product. The peptide may be purified by any means known in the art, e.g., by one or more chromatographic methods(s), one or more filtration methods(s), one or more electrophoretic methods(s), one or more precipitation-based method(s) and/or one or more dialysis method(s). In one embodiment, the purifying the crude peptide comprises one or more chromatographic method(s). In one embodiment, the purifying the crude peptide comprises one or more precipitation-based methods. In one embodiment, the purifying the crude peptide comprises reverse phase high-performance liquid chromatography. In one embodiment, purifying the crude peptide comprises one or more precipitation-based method(s) and reverse-phase high-performance liquid chromatography. It will be appreciated that one or more counterions may be introduced in the course of peptide synthesis and/or purification, e.g. trifluoroacetic acid or phosphates. The person skilled in the art will appreciate that it may be desirable to replace the peptide counterion at some point during or after the peptide synthesis and/or purification, e.g. with a pharmaceutically acceptable counterion such as acetate or chloride. The counterion may be replaced by any means known in the art for ion exchange, examples of which include, but are not limited to, ion exchange chromatography, precipitation-based methods, dialysis, ultrafiltration, chemical reaction, and combinations thereof.

In some embodiments, the method provides the compound of Formula (1) in a purity (in %) of at least about 50, 55, 60, 65, 70, 75, 80, 85, 90, 95, or 98.

In some embodiments, the method provides the compound of Formula (1) in a yield (in %) of at least about 20, 25, 30, 35, 40, 50, 55, 60, 65, 70, 75, 80, 85, 90, 95, or 98.

In some embodiments, the method is for the preparation of a compound of Formula (1), wherein the compound is

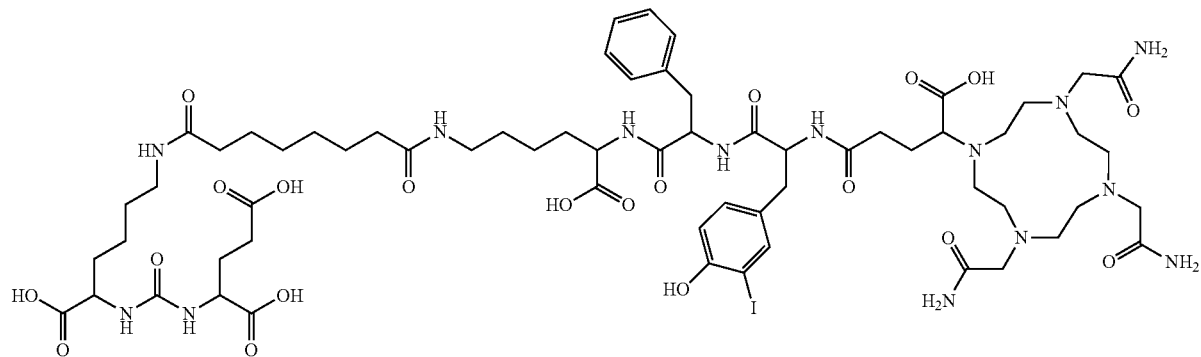 [SMILES: NC(=O)CN1CCN(CC(N)=O)CCN(C(CCC(=O)NC(Cc2ccc(O)c(I)c2)C(=O)NC(Cc2ccccc2)C(=O)NC(CCCCNC(=O)CCCCCCC(=O)NCCCCC(NC(=O)NC(CCC(=O)O)C(=O)O)C(=O)O)C(=O)O)C(=O)O)CCN(CC(N)=O)CC1]

or a salt, solvate or stereoisomer thereof.

In some embodiments, the method is for the preparation of a compound of Formula (1), wherein the compound is selected from:

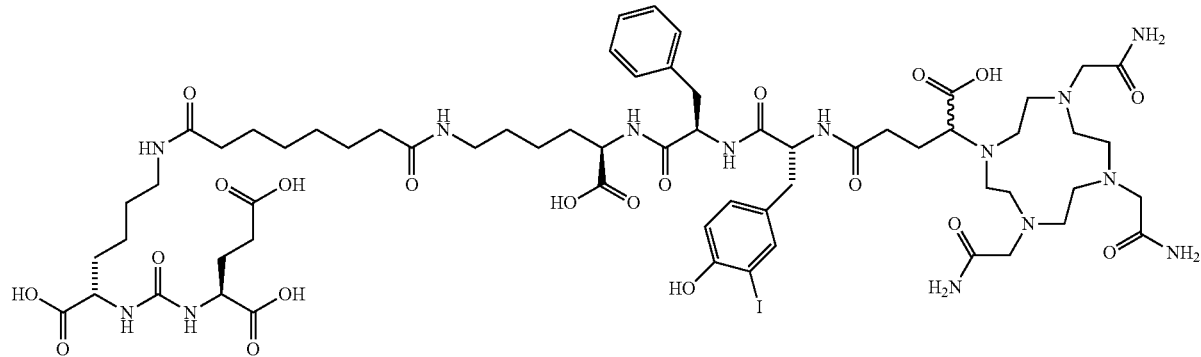

-continued

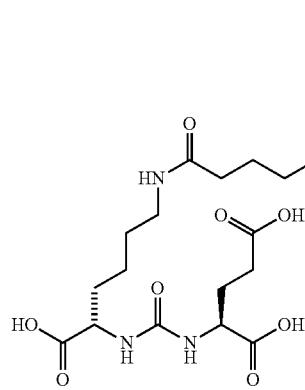
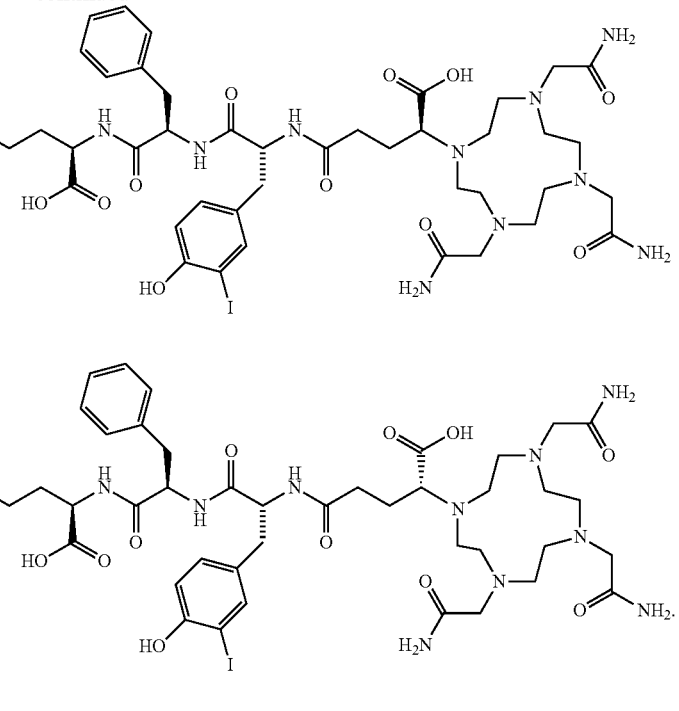

or a salt, solvate or stereoisomer thereof.

In some embodiments, the method further comprises radiolabelling the compound of Formula (1) with a radioisotope, which may be any radioisotope as described herein. In some embodiments, radiolabelling the compound of Formula (1) with a radioisotope comprises contacting the compound of Formula (1) with a solution comprising the radioisotope. In some embodiments, the solution comprising the radioisotope comprises the radioisotope as a salt, for example a chloride salt. In some embodiments, contacting the compound of Formula (1) with a solution comprising the radioisotope is for a period of time (in minutes) greater than about 1, 5, 10, 30, 60, 120, 180, or 360. In some embodiments, contacting the compound of Formula (1) with a solution comprising the radioisotope is at ambient temperature. In some embodiments, contacting the compound of Formula (1) with a solution comprising the radioisotope is at a temperature greater than ambient temperature. In some embodiments, the solution comprising the radioisotope has a pH greater than about 1, 2, 3, 4, 5, 6, 7, 8, 9, 10, 11, 12, 13, or 14. In some embodiments, the solution comprising the radioisotope is substantially comprises an aqueous solvent. In some embodiments, the solution comprising the radioisotope is substantially comprised of an aqueous salt acetate solvent.

The present disclosure can also be described by reference to one or more of the following example embodiments. It will be appreciated that the specific embodiments presented below are not intended to be limiting to the scope. It will be appreciated that persons skilled in the art may incorporate one or more of the elements, features or embodiments in the listing below (indeed, any such aspect or embodiment described herein) into combinations not specifically set forth herein. All such embodiments are considered to be within the scope of the disclosure.

1. A compound of Formula (1), or a pharmaceutically acceptable salt, solvate or stereoisomer thereof;

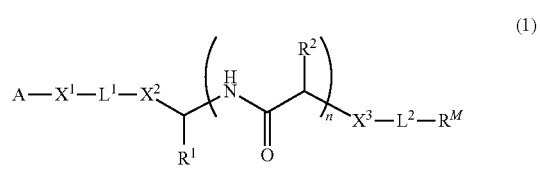

wherein:

n is 0 to 3;

A is a PSMA targeting ligand;

$X^1$ to $X^3$ are each independently absent or selected from the group consisting of —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O)NR$^3$—, —OS(=O)$_2$—, —N(R$^3$)C(=S)N(R$^3$)— and —N(R$^3$)C(=O)N(R$^3$)—;

$L^1$ and $L^2$ are each independently absent or a divalent linking moiety;

$R^1$ and each $R^2$ are independently selected from the group consisting of aryl, alkylaryl, heteroaryl and alkylheteroaryl, each of which is optionally substituted.

$R^3$ is selected from the group consisting of H, alkyl, alkenyl, alkynyl, carbocyclyl, heterocyclyl, alkylcarbocyclyl, and alkylheterocyclyl, each of which is optionally substituted; and $R^M$ is chelating moiety having the structure of Formula (M-1)

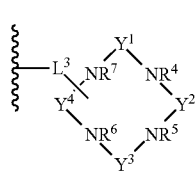

(M-1)

wherein:
Y$^1$ to Y$^4$ are each independently an optionally substituted —C$_{1-6}$alkyl-;
R$^4$ to R$^7$ are each independently selected from the group consisting of —C(=O)N(R$^3$)$_2$, —P(=O)(OR$^3$)$_2$, —P(=O)OR$^3$(R$^3$), —P(=O)(R$^3$)$_2$, —C$_{1-10}$alkylC(=O)N(R$^3$)$_2$, —C$_{1-10}$alkylP(=O)(OR$^3$)$_2$, —C$_{1-10}$alkylP(=O)OR$^3$(R$^3$) and —C$_{1-10}$alkylP(=O)(R$^3$)$_2$, or one of R$^4$ and R$^6$ or R$^5$ and R$^7$ together from a —(CH$_2$)$_m$— bridge; wherein each C$_{1-10}$alkyl is optionally substituted.
L$^3$ is absent or a divalent linking moiety connecting the ring to L$^2$ in Formula (1) via any ring heteroatom or any one of Y$^1$ to Y$^4$;
⌇ represents the bond which attaches R$^M$ to L$^2$ in Formula (1);
m is 1 to 3; and
wherein R$^M$ is optionally complexed to a radioisotope.

2. The compound of example embodiment 1, wherein X$^1$ to X$^3$ are each independently absent or selected from the group consisting of —O—, —S—, —C(=O)—, —C(=O)NR$^3$—, —NR$^3$—, —C(=O)O—, —C(=O)S—, —S(=O)$_2$—, —S(=O)$_2$NR$^3$—S(=O)NR$^3$—, —OS(=O)$_2$—, —N(R$^3$)C(=S)N(R$^3$)— and —N(R$^3$)C(=O)N(R$^3$)—;
R$^1$ and each R$^2$ are independently selected from the group consisting of aryl, alkylaryl, heteroaryl and alkylheteroaryl,
R$^3$ is selected from the group consisting of H, alkyl, alkenyl, alkynyl, carbocyclyl, heterocyclyl, alkylcarbocyclyl, and alkylheterocyclyl,
R$^4$ to R$^7$ are each independently selected from the group consisting of —C(=O)N(R$^3$)$_2$, —P(=O)(OR$^3$)$_2$, —P(=O)OR$^3$(R$^3$), —P(=O)(R$^3$)$_2$, —C$_{1-10}$alkylC(=O)N(R$^3$)$_2$, —C$_{1-10}$alkylP(=O)(OR$^3$)$_2$, —C$_{1-10}$alkylP(=O)OR$^3$(R$^3$) and —C$_{1-10}$alkylP(=O)(R$^3$)$_2$, or one of R$^4$ and R$^6$ or R$^5$ and R$^7$ together from a —(CH$_2$)$_m$— bridge; wherein each C$_{1-10}$alkyl is optionally substituted with one or more R$^8$.
Y$^1$ to Y$^4$ are each independently —C$_{1-6}$alkyl-;
wherein each of Y$^1$ to Y$^4$ and R$^1$ to R$^7$ is optionally substituted with one or more R$^8$;
each R$^8$ is independently selected from the group consisting of H, halogen, C$_{1-10}$alkyl, OC$_{1-10}$alkyl, C$_{1-10}$haloalkyl, OC$_{1-10}$haloalkyl, C$_{2-10}$alkenyl, C$_{2-10}$alkynyl, OC$_{2-10}$alkenyl, OC$_{2-10}$alkynyl, 3-10 membered carbocyclyl, 3-10-membered heterocyclyl, C$_{1-10}$alkyl-3-10-membered-carbocyclyl, C$_{1-10}$alkyl-3-10-membered-heterocyclyl, —NO$_2$, —CN, —SCN, —N$_3$, =O, —N(R$^9$)$_2$, —C(=O)N(R$^9$)$_2$, —S(=O)N(R$^9$)$_2$, —S(=O)$_2$N(R$^9$)$_2$, —OR$^9$, —SR$^9$, —OC(=O)R$^9$, —C(=O)R$^9$, —C(=O)OR$^9$—S(=O)R$^9$, —S(=O)$_2$R$^9$, —S(=O)OR$^9$, —S(=O)$_2$OR$^9$, —S(=O)(OR$^9$)$_2$, —OS(=O)R$^9$, —OS(=O)$_2$R$^9$, —OS(=O)OR$_9$, —OS(=O)$_2$OR$^9$, —OS(=O)(OR$^9$)$_2$, —N(R$^9$)C(=O)R$^9$, —N(R$^9$)S(=O)R$^9$, —N(R$^9$)C(=O)N(R$^9$)$_2$, —N(R$^9$)S(=O)$_2$R$^9$, —P(=O)(OR$^9$)$_2$, —P(=O)OR$^9$(R$^9$), —P(=O)(R$^9$)$_2$, —OP(=O)(OR$^9$)$_2$, —OP(=O)OR$^9$(R$^9$) and —OP(=O)(R$^9$)$_2$, wherein each C$_{1-10}$alkyl, C$_{1-10}$haloalkyl, C$_{2-10}$alkenyl, C$_{2-10}$alkynyl, 3-10 membered-carbocyclyl, and 3-10-membered-heterocyclyl is optionally substituted with one or more R$^{10}$;

each R$^9$ is independently selected from the group consisting of H, C$_{1-6}$alkyl, 3-10 membered carbocyclyl, 3-10-membered heterocyclyl, C$_{1-6}$alkyl-3-10-membered-carbocyclyl, and C$_{1-6}$alkyl-3-10-membered-heterocyclyl; wherein each C$_{1-6}$alkyl, 3-10-membered-carbocyclyl, and 3-10-membered heterocyclyl is optionally substituted with one or more R$^{10}$;

each R$^{10}$ is independently selected from the group consisting of H, halogen, —NO$_2$, —N(R$^{11}$)$_2$, —CN, —SCN, —N$_3$, =O, —C(=O)R$^{11}$, —C(=O)OR$^{11}$, —C(=O)N(R$^{11}$)$_2$, —N(R$^{11}$)C(=O)R$^{11}$, —OR$^{11}$, —P(=O)(OR$^{11}$)$_2$, —P(=O)OR$^{11}$(R$^{11}$), —P(=O)(R$^{11}$)$_2$, C$_{1-6}$alkyl, and —OC$_{1-6}$alkyl, each R$^{11}$ is independently selected from the group consisting of H, C$_{1-10}$alkyl, C$_{1-10}$alkyl, C$_{2-10}$alkenyl, C$_{2-10}$alkynyl, 3-10 membered carbocyclyl, 3-10 membered heterocyclyl, C$_{1-10}$alkyl-3-10-membered carbocyclyl, C$_{1-10}$alkyl-3-10-membered heterocyclyl.

3. The compound of example embodiment 1 or example embodiment 2, wherein R$^M$ is a chelating moiety having a structure selected from the group consisting of Formula (M-1A) to (M-1D):

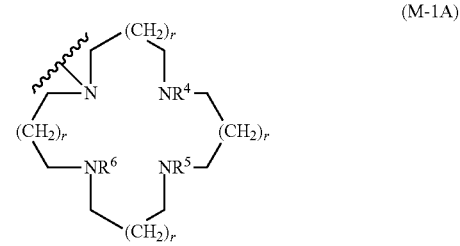

(M-1A)

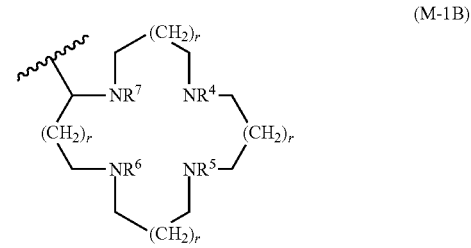

(M-1B)

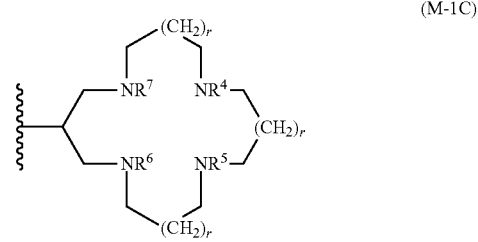

(M-1C)

(M-1D)

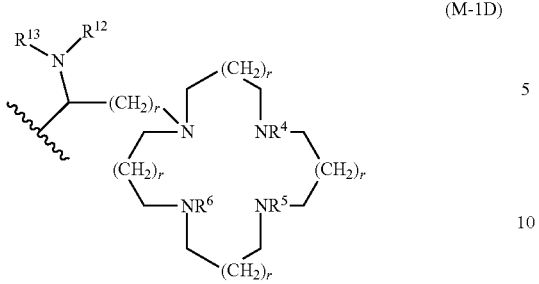

wherein:
$R^4$ to $R^7$ are each independently selected from the group consisting of —C(=O)N($R^{14}$)$_2$, —P(=O)(O$R^{14}$)$_2$, —P(=O)O$R^3$($R^{14}$), —P(=O)($R^{14}$)$_2$, —$C_{1-10}$alkylC(=O)N($R^{14}$)$_2$, —$C_{1-10}$alkylP(=O)(O$R^{14}$)$_2$, —$C_{1-10}$alkylP(=O)O$R^{14}$($R^{14}$) and —$C_{1-10}$alkylP(=O)($R^{14}$)$_2$, or one of $R^4$ and $R^6$ or $R^5$ and $R^7$ together from a —(CH$_2$)$_m$— bridge; wherein each $C_{1-6}$alkyl is optionally substituted with one or more $R^8$;
$R^{12}$ and $R^{13}$ are each independently selected from the group consisting of H, —C(=O)O$R^{14}$, —C(=O)N($R^{14}$)$_2$, —$C_{1-6}$alkylC(=O)O$R^{14}$, —$C_{1-6}$alkylC(=O)N($R^{14}$)$_2$—P(=O)(O$R^{14}$)$_2$—P(=O)O$R^{14}$($R^{14}$), —P(=O)($R^{14}$)$_2$, —$C_{1-6}$alkylP(=O)O$R^{14}$($R^{14}$) and —$C_{1-6}$ alkylP(=O)($R^{14}$)$_2$, wherein each $C_{1-6}$alkyl is optionally substituted with one or more $R^8$, or $R^{12}$ and $R^{13}$ together form an optionally substituted heterocyclyl.
each $R^{14}$ is independently selected from the group consisting of H, $C_{1-10}$alkyl, $C_{2-10}$alkenyl, $C_{2-10}$alkynyl, 3-10 membered carbocyclyl, 3-10 membered heterocyclyl, $C_{1-10}$alkyl-3-10-membered carbocyclyl, $C_{1-10}$alkyl-3-10-membered heterocyclyl, wherein each alkyl, alkenyl, alkynyl carbocyclyl, and heterocyclyl is optionally substituted with one or more $R^8$;
⌇ represents the bond which attaches $R^M$ to $L^2$ in Formula (1); r is 0 or 1; and
m is 1 to 3.
4. The compound of any one of example embodiments 1 to 3, wherein $R^M$ is a chelating moiety, having a structure selected from the group consisting of Formula (M-1Ai) to (M-1Dii):

(M-1Ai)

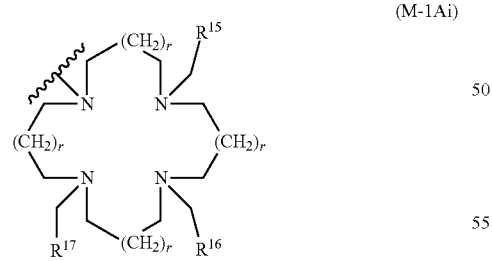

(M-1Bi)

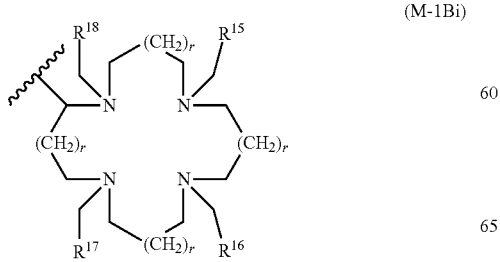

(M-1Ci)

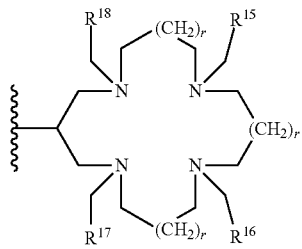

(M-1Di)

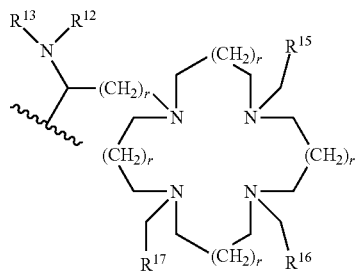

(M-1Aii)

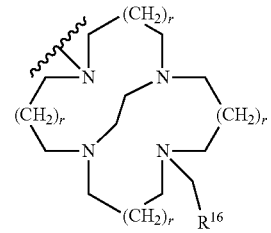

(M-1Bii)

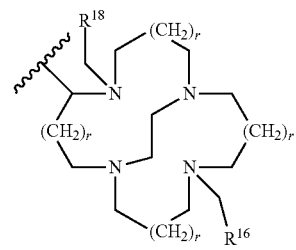

(M-1Biii)

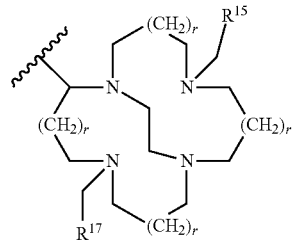

(M-1Cii)

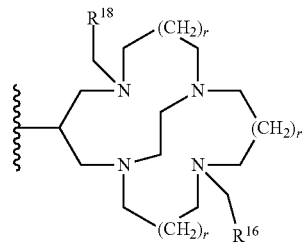

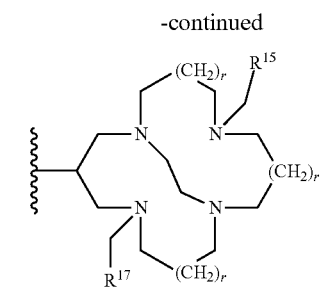

(M-1Ciii)

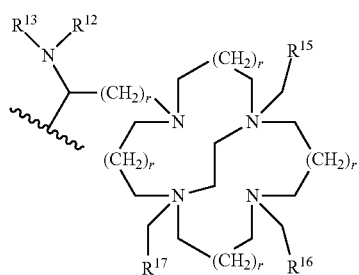

(M-1Dii)

wherein:
$R^{12}$ and $R^{13}$ are each independently selected from the group consisting of H, —C(=O)OR$^{14}$, —C(=O)N(R$^{14}$)$_2$, —C$_{1-6}$alkylC(=O)OR$^{14}$, —C$_{1-6}$alkylC(=O)N(R$^{14}$)$_2$—P(=O)(OR$^{14}$)$_2$—P(=O)OR$^{14}$(R$^{14}$), —P(=O)(R$^{14}$)$_2$, —C$_{1-6}$alkylP(=O)OR$^{14}$(R$^{14}$) and —C$_{1-6}$ alkylP(=O)(R$^{14}$)$_2$, wherein each C$_{1-6}$alkyl is optionally substituted with one or more R$^8$, or R$^{12}$ and R$^{13}$ together form an optionally substituted heterocyclyl; and $R^{15}$ to $R^{18}$ are each independently selected from the group consisting of —C(=O)N(R$^{14}$)$_2$, —P(=O)(OR$^{14}$)$_2$, —P(=O)OR$^{14}$(R$^{14}$), and —P(=O)(R$^{14}$)$_2$;

⁓ represents the bond which attaches R$^M$ to the L$^2$ in Formula (1); and r is 0 or 1.

5. The compound of example embodiment 4, wherein:
$R^{12}$ and $R^{13}$ are each independently —C(=O)OH or —C(=O)NH$_2$; and
$R^{15}$ to $R^{18}$ are each independently selected from the group consisting of —C(=O)NH$_2$, —P(=O)(OH)$_2$, —P(=O)(OH)H, and —P(=O)(OH)OC$_{1-6}$alkyl.

6. The compound of any one of example embodiments 1 to 5, wherein R$^M$ is a chelating moiety having a structure of Formula (M-1E), wherein ⁓ represents the bond which attaches R$^M$ to L$^2$ in Formula (1):

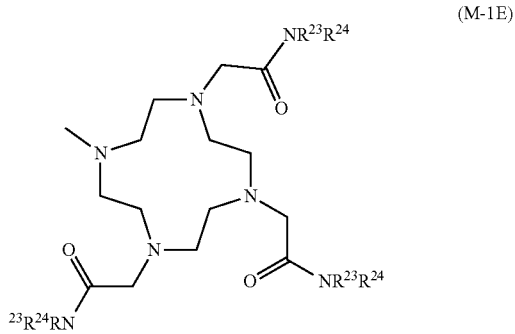

(M-1E)

wherein R$^{23}$ and R$^{24}$ are each independently selected from the group consisting of H alkyl, alkenyl, alkynyl, carbocyclyl, heterocyclyl, alkylcarbocyclyl, and alkylheterocyclyl, each of which is optionally substituted or at least one R$^{23}$ and R$^{24}$ together form an optionally substituted 3-10-membered heterocyclyl.

7. The compound of any one of example embodiments 1 to 6, wherein R$^M$ is a chelating moiety having a structure of Formula (M-1F), wherein ⁓ represents the bond which attaches R$^M$ to L$^2$ in Formula (1):

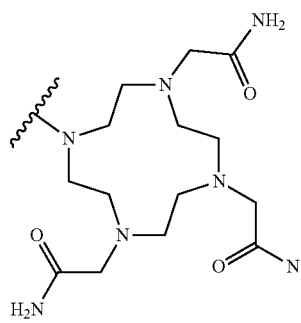

(M-1F)

8. The compound of any one of example embodiments 1 to 7, wherein L$^1$ and L$^2$ are each independently an aliphatic linker group which is uninterrupted or interrupted with one or more groups selected from —O—, —S—, —C(=O)—, —C(=O)NR$^3$—, —NR$^3$—, —C(=O)O—, —C(=O)S—, —S(=O)$_2$—, —N(R$^3$)C(=S)N(R$^3$)—, and —N(R$^3$)C(=O)N(R$^3$)—, and is optionally substituted with one or more R$^8$.

9. The compound of example embodiment 8, wherein L$^1$ is —C$_{1-20}$alkyl- which is uninterrupted or interrupted with one or more groups selected from —O—, —S—, —C(=O)—, —C(=O)NH—, —NH—, —C(=O)O—, —C(=O)S—, —S(=O)$_2$—, —NHC(=S)NH—, and —NHC(=O)NH—; and L$^2$ is —C$_{1-10}$alkyl-, wherein each alkyl is optionally substituted with one or more R$^8$.

10. The compound of example embodiment 8 or example embodiment 9, wherein each of L$^1$ and L$^2$ are independently optionally substituted with one or more groups selected from H, C$_{1-10}$alkyl, OC$_{1-10}$alkyl, 3-10 membered carbocyclyl, 3-10-membered heterocyclyl, C$_{1-10}$alkyl-3-10-membered-carbocyclyl, C$_{1-10}$alkyl-3-10-membered-heterocyclyl, —N(R$^9$)$_2$, —C(=O)N(R$^9$)$_2$, —OR$^9$, —OC(=O)R$^9$, —C(=O)R$^9$, —C(=O)OR$^9$, and —N(R$^9$)C(=O)R$^9$, wherein each C$_{1-10}$alkyl, C$_{1-10}$haloalkyl, C$_{2-10}$alkenyl, C$_{2-10}$alkynyl, 3-10-membered-carbocyclyl, and 3-10-membered-heterocyclyl is optionally substituted with one or more R$^{10}$.

11. The compound of any one of example embodiments 1 to 10, wherein X$^1$ to X$^3$ are each independently selected from the group consisting of —O—, —S—, —C(=O)—, —C(=O)NH—, —NH—, —C(=O)O—, —C(=O)S—, —S(=O)$_2$—, —NHC(=S)NH—, and —NHC(=O)NH—.

12. The compound of any one of example embodiments 1 to 11, wherein X$^1$ to X$^3$ are each —C(=O)NH—

13. The compound of any one of example embodiments 1 to 12, wherein the moiety —X$^1$-L$^1$-X$^2$— in Formula (1) has a structure (L-1):

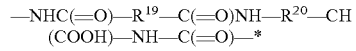

—NHC(=O)—R$^{19}$—C(=O)NH—R$^{20}$—CH(COOH)—NH—C(=O)—*  (L-1)

wherein:
* indicates the bond which is attached to the carbon atom carrying R$^1$ in Formula (1); and $R^{19}$ and $R^{20}$ are each independently selected from a $C_{1-20}$alkyl optionally substituted with one or more $R^8$.

14. The compound of any one of example embodiments 1 to 13, wherein the moiety —$X^3$-$L^2$- in Formula (1) has the structure (L-2) or (L-3):

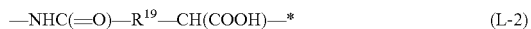  (L-2)

  (L-3)

wherein:
* indicates the bond which is attached to $R^M$ in Formula (1).

15. The compound of any one of example embodiments 1 to 14, wherein —$X^3$-$L^2$-$R^M$ in Formula (1) is 2(R, S)-[1,4,7,10-tetraazacyclododecane-4,7,10-triacetamido]-5-amidopentanoic acid.

16. The compound of any one of example embodiments 1 to 15, wherein $R^1$ and $R^2$ are each independently an optionally substituted alkylaryl or an optionally substituted alkylheteroaryl.

17. The compound of example embodiment 16, wherein $R^1$ and $R^2$ are each independently an optionally substituted alkylaryl.

18. The compound of example embodiment 16 or example embodiment 17, wherein $R^1$ and $R^2$ are each independently an optionally substituted benzyl.

19. The compound of any one of example embodiments 16 to 18, wherein $R^1$ and $R^2$ are each independently optionally substituted with one or more groups selected from H, halogen, $C_{1-10}$alkyl, $OC_{1-10}$alkyl, $C_{1-10}$haloalkyl, $OC_{1-10}$haloalkyl, $C_{2-10}$alkenyl, $C_{2-10}$alkynyl, $OC_{2-10}$alkenyl, $OC_{2-10}$alkynyl, —$NO_2$, —$N(R^1)_2$, —CN, —SCN, —$N_3$, =O, —C(=O)$R^1$, —C(=O)O$R^1$, —N($R^{1'}$)C(=O)$R^1$, and —O$R^1$.

20. The compound of any one of example embodiments 1 to 19, wherein A is a PSMA targeting ligand having the structure of Formula (A-2):

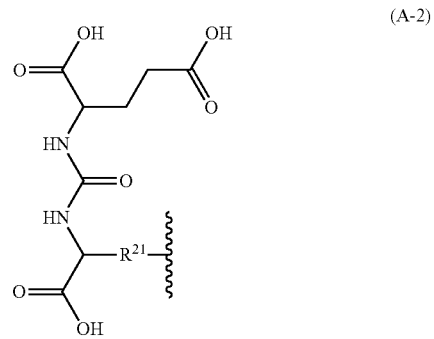  (A-2)

wherein:
⸺ represents the bond which attaches A to the $X^1$ in Formula (1); and
$R^{21}$ is $C_{1-20}$alkyl optionally substituted with one or more $R^8$.

21. The compound of any one of example embodiments 1 to 20, wherein the compound of Formula (1) is

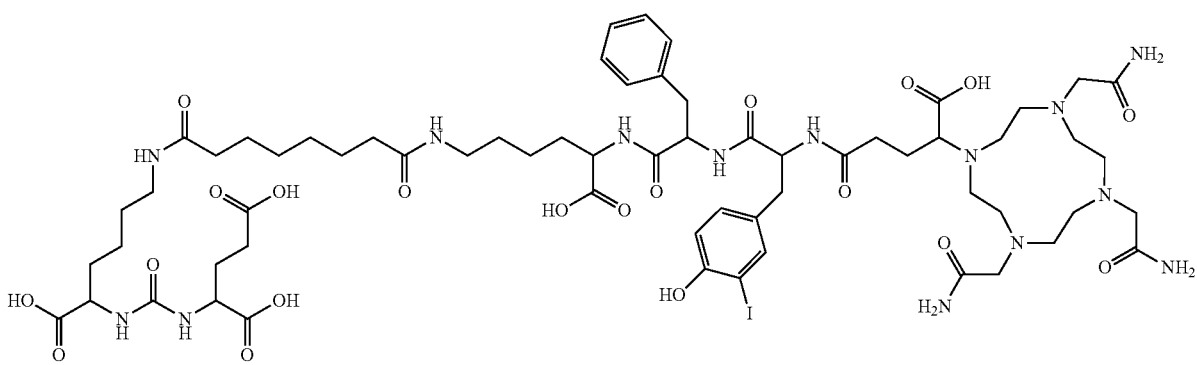 [SMILES: NC(=O)CN1CCN(CC(N)=O)CCN(C(CCC(=O)NC(Cc2ccc(O)c(I)c2)C(=O)NC(Cc2ccccc2)C(=O)NC(CCCCNC(=O)CCCCCCC(=O)NCCCCC(NC(=O)NC(CCC(=O)O)C(=O)O)C(=O)O)C(=O)O)C(=O)O)CCN(CC(N)=O)CC1]

22. The compound of any one of example embodiments 1 to 21, wherein the compound of Formula (1) is selected from the group consisting of:

29. A method for treating and/or preventing a PSMA-expressing cancer in a subject in need thereof, comprising administering a therapeutically effective amount of a com-

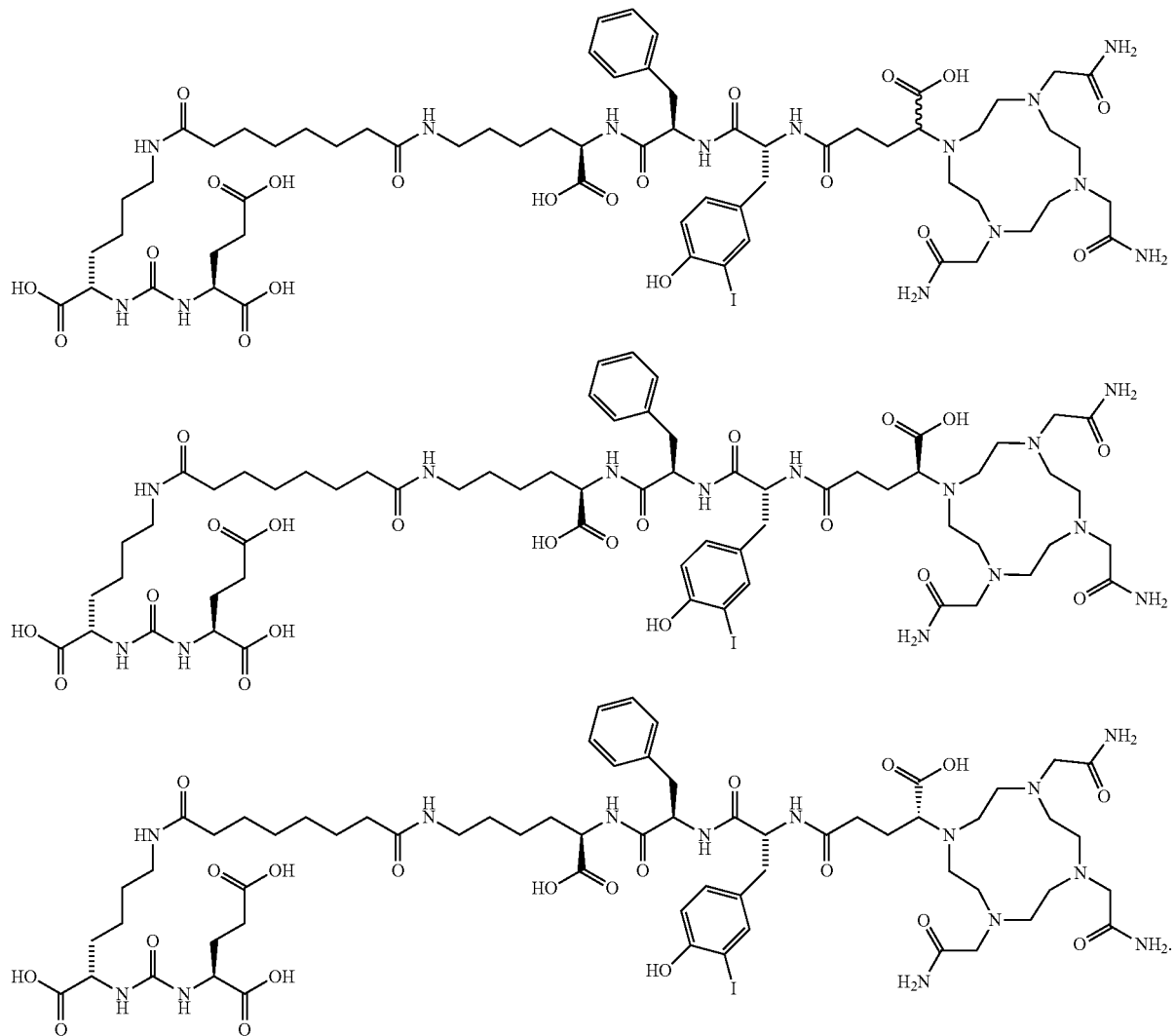

23. The compound of any one of example embodiments 1 to 22, wherein $R^M$ is complexed to a radioisotope.

24. The compound of example embodiment 23, wherein the radioisotope is selected from the group consisting of $^{44}$Sc, $^{47}$Sc, $^{51}$Mn, $^{52m}$Mn, $^{52g}$Mn, $^{55}$Co, $^{58}$Co, $^{58m}$Co, $^{61}$Co, $^{61}$Cu $^{62}$Cu $^{64}$Cu $^{67}$Cu $^{68}$Ga, $^{86}$Y $^{90}$Y$^{89}$Zr, $^{111}$In, $^{134}$La, $^{152}$Eu, $^{149}$Tb, $^{152}$Tb, $^{155}$Tb, $^{161}$Tb, $^{177}$Lu, $^{203}$Pb, $^{211}$Pb, $^{212}$Pb, $^{212}$Bi, $^{213}$Bi, $^{225}$Ac, and $^{227}$Th.

25. The compound of example embodiment 23 or example embodiment 24, wherein the radioisotope is $^{212}$Pb.

26. A compound of any one of example embodiments 1 to 25 for use in diagnosing, treating and/or preventing a PSMA-expressing cancer.

27. The compound of example embodiment 26, wherein the PSMA-expressing cancer is prostate cancer, preferably metastatic castrate-resistant prostate cancer (mCRPC).

28. A pharmaceutical composition comprising the compound of any one of example embodiments 1 to 27, and a pharmaceutically acceptable excipient.

pound of any one of example embodiments 1 to 27 or a pharmaceutical composition of example embodiment 28 to the subject.

30. Use of a compound of any one of example embodiments 1 to 27 or a pharmaceutical composition of example embodiment 28 for treating and/or preventing a PSMA-expressing cancer.

31. Use of a compound of any one of example embodiments 1 to 27 or a pharmaceutical composition of example embodiment 26 in the manufacture of a medicament for treating and/or preventing a PSMA-expressing cancer.

32. The method or use of any one of example embodiments 29 to 31, wherein the PSMA-expressing cancer is prostate cancer, preferably metastatic castrate-resistant prostate cancer (mCRPC).

33. An imaging agent comprising the compound of any one of example embodiments 1 to 27.

34. The imaging agent of example embodiment 33, wherein $R^M$ is complexed to a positron-emitting radioisotope or a gamma-emitting radioisotope.

35. The imaging agent of example embodiment 34, wherein the positron-emitting radioisotope is selected from the group consisting of $^{68}$Ga, $^{64}$Cu, $^{55}$Co and $^{89}$Zr.

36. A diagnostic composition comprising the imaging agent of any one of example embodiments 33 to 35 and a pharmaceutically acceptable excipient.

37. A method of imaging a tissue in a subject, comprising administering a diagnostically effective amount of the imaging agent of any one of example embodiments 33 to 35 or the diagnostic composition of example embodiment 36 to the subject.

38. Use of an imaging agent of any one of example embodiments 33 to 35 or a diagnostic composition of example embodiment 36 for imaging a tissue in a subject.

39. An ex-vivo method of imaging a tissue sample comprising a diagnostically effective amount of the imaging agent of any one of example embodiments 33 to 35 or the diagnostic composition of example embodiment 36.

40. Use of a compound of any one of example embodiments 1 to 27, a pharmaceutical composition of example embodiment 26, in the manufacture of an imaging agent for imaging a tissue in a subject.

41. The method or use of any one of example embodiments 37 to 40, wherein the tissue is a PSMA-expressing tumour tissue.

42. The method or use of example embodiment 41, wherein the PSMA-expressing tumour tissue is prostate cancer, preferably metastatic castrate-resistant prostate cancer (mCRPC).

EXAMPLES

In order that the disclosure may be more clearly understood, particular embodiments of the invention are described in further detail below by reference to the following non-limiting experimental materials, methodologies and examples.

General Materials and Methods

Fmoc-(9-fluorenylmethoxycarbonyl-) amino acids, resins and cyclen were purchased from Chem-Impex International (Illinois, USA). All other reagents and solvents were purchased from Sigma-Aldrich or ChemPep (China). The chelator DO3AM was purchased from Chematech (Dijon, France). Analytical reversed-phase high-performance liquid chromatography (RP-HPLC) was performed on a Phenomonex Jupiter@Proteo C18 (4 μm, 90 Å, 150×4.6 mm) column using a Shimadzu Prominence HPLC. The peptides were eluted with different gradients of 0.1% (v/v) trifluoroacetic acid (TFA) in H$_2$O (solvent A) and 0.1% TFA in acetonitrile (solvent B). HPLC-UV detection was performed at 220 and 254 nm. For radioactive detection, a PMT/NaI (Tl) type counter was connected to a Shimadzu Prominence HPLC. ESI-mass spectra were acquired on a Varian 500-MS IT mass spectrometer (Agilent Technologies, Santa Clara, USA) and NMR spectra were obtained using a Varian 500 MHz Inova.

Example 1: Synthesis of 5-(tert-butoxy)-5-oxo-4-(4,7,10-tris(2-amino-2-oxoethyl)-1,4,7,10-tetraazacyclododecan-1-yl)pentanoic acid (Pent(OtBu)-DO3AM) 3

DO3AM 1 (100 mg, 0.29 mmol, 1.0 equiv), bromide 2 (110 mg, 0.32 mmol, 1.1 equiv) and K$_2$CO$_3$ (40 mg, 0.79 mmol, 2.0 equiv) in DMF (1 mL) was stirred overnight. The solution was filtered to remove insoluble salt and the filtrate was concentrated in vacuo. The residual was purified by semi-prep HPLC to give a yellow gum (60 mg). The benzyl protected pent(OtBu)-DO3AM was confirmed by ESI-MS (M+H$^+$): 619.7 and purity by UV-HPLC was >98%. 20% Pd/C (20% w/w, 10 mg) was suspended in a stirring solution of Pent(OtBu)-DO3AM-OBn (50 mg, 0.08 mmol, 1 equiv) in methanol (5 mL) under a hydrogen atmosphere. The solution was stirred for 4 h and carefully filtered to remove the Pd/C. The residual was concentrated in vacuo to give the title compound (22 mg, 51%). $^1$H NMR (D$_2$O/CD$_3$OD, 500 MHz): δ 4.84 (s, 6H), 3.71-3.43 (m, 2H), 3.35 (s, 16H), 3.30-3.30 (s, 1H), 2.39-2.29 (m, 2H), 1.49 (s, 9H). $^1$H NMR (D$_2$O/CD$_3$OD, 125 MHz): δ 83.26, 57.86, 56.87, 54.17, 53.76, 52.45, 49.85, 33.80, 28.53, 28.41.

Example 2: Synthesis of ADVC001

A non-limiting illustration of the overall synthesis used to obtain a compound, ADVC001, with respect to the below Examples and compounds of Formula (1) is provided below as Scheme 1:

Scheme 1
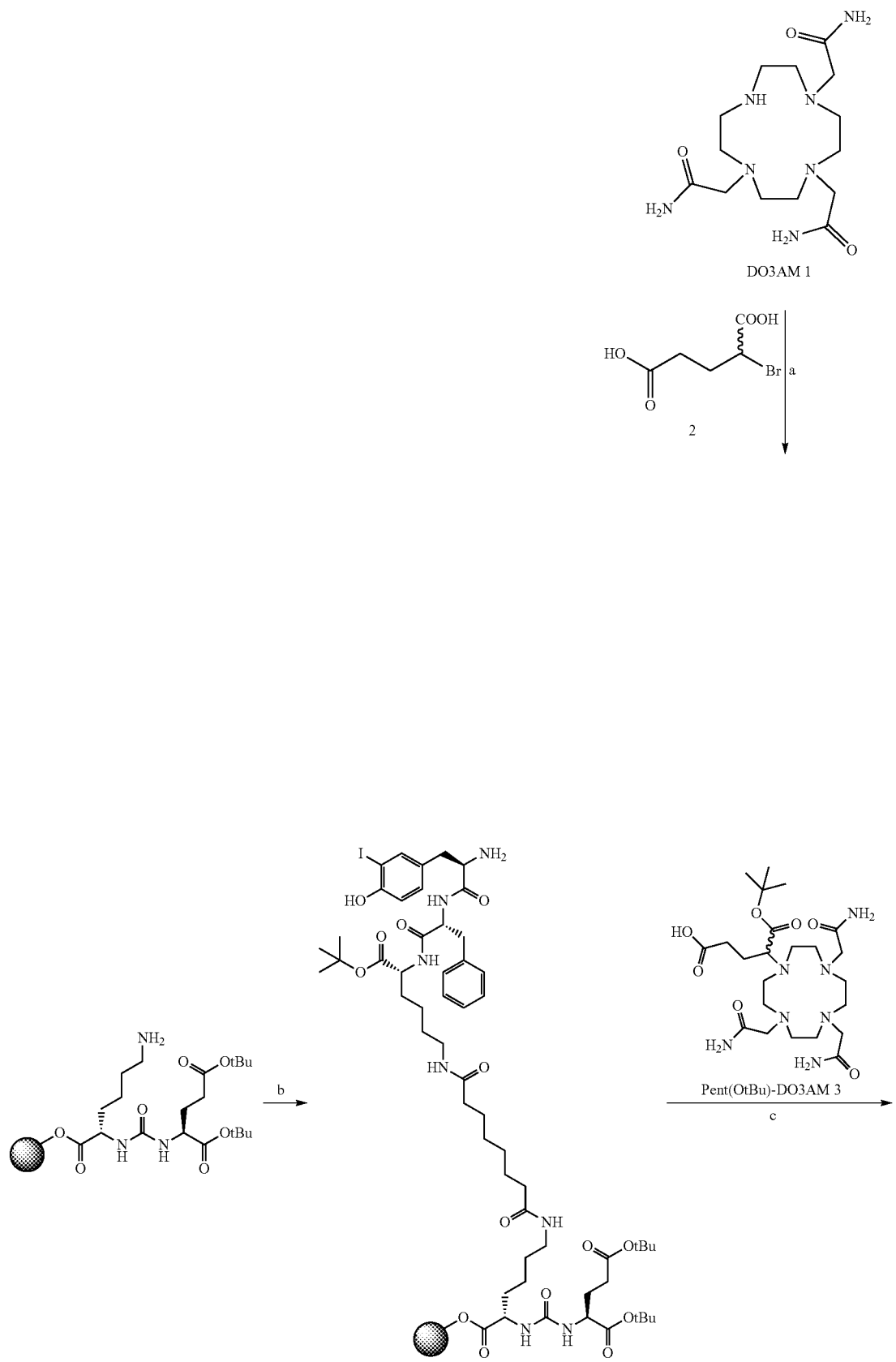

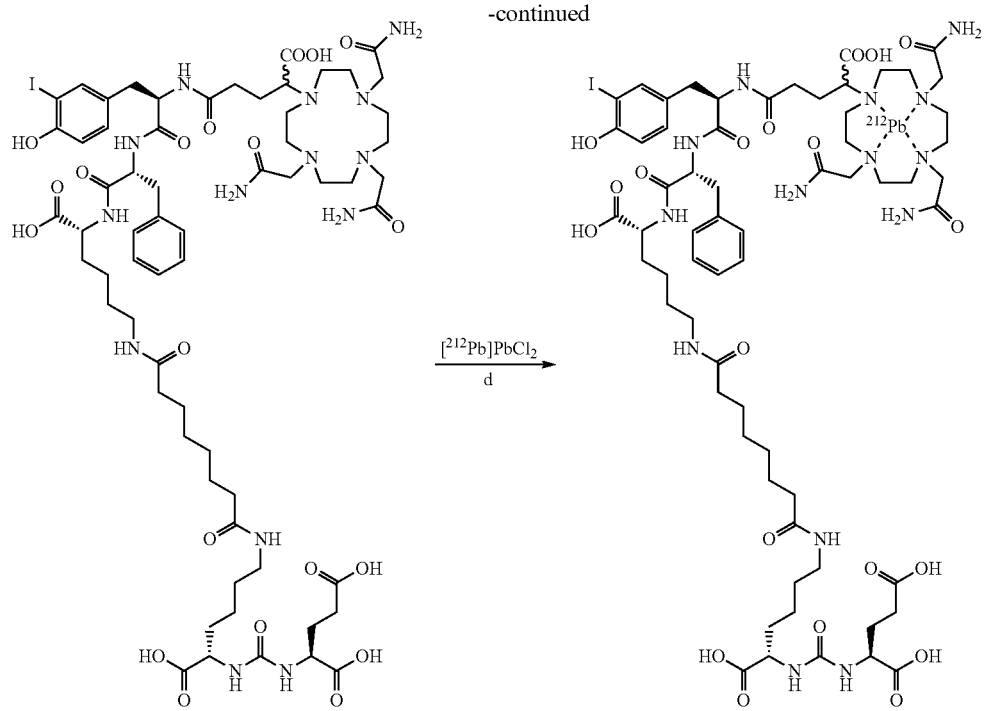

(reagents and conditions): a) K$_2$CO$_3$, DMF; b) i) suberic acid, HBTU, DIPEA, DMF, ii) Fmoc-D-Lys-OtBu•HCl, HBTU, DIPEA, DMF, iii) 20% piperidine, DMF, iv) Fmoc-D-Phe-OH, HBTU, DIPEA, DMF, iii) 20% piperidine, DMF, iv) Fmoc-3-Iodo-D-Tyr-OH, HBTU, DIPEA, DMF, DMF; c) i) 3, HBTU, DIPEA, DMF; ii) 88:2:5:5 TFA/TIPS/DTT/H$_2$O; d) [$^{212}$Pb]PbCl$_2$, NaOAc (pH 5.5).

The solid-phase synthesis of the peptidomimetic glutamate-urea-lysine binding motif is summarized in Scheme 1. The ensuing coupling of the linker was performed according to standard fluorenylmethoxycarbonyl (Fmoc) protocol (Wellings et al. *Methods in Enzymology*, 1997, 289, 44-67, which is herein incorporated by reference) and starting with reported compound 4 (Benesova et al. *J. Med. Chm.* 2016, 59, 5, 1761-1775 which is herein incorporated by reference). Finally, conjugation of the Pent(OtBu)-DO3AM chelator (Scheme 1) was realized using a HATU-activation in the presence of DIPEA in DMF on resin. Final cleavage off-resin and deprotection was achieved with TFA/TIPS/H$_2$O/DTT mix. The crude peptide conjugate was purified by HPLC and lyophilised to give white powder. Purity of ADVC001 was 98.6% by HPLC (Rt=4.6 min, 18% Solvent B for 5 min, 40% solvent B over 6 min) and as HCl salt. Calculated mass (C$_{63}$H$_{95}$IN$_{14}$O$_{20}$)=1494.6, found m/z [M+H$^+$]: 1495.1.

Example 2.1: Alternative Synthesis of Non-Complexed ADVC001

A non-limiting illustration of an alternative overall synthesis used to obtain the non-complexed form of ADVC001, with respect to the below Examples and compounds of Formula (1) is provided below as Scheme 2:

Scheme 2
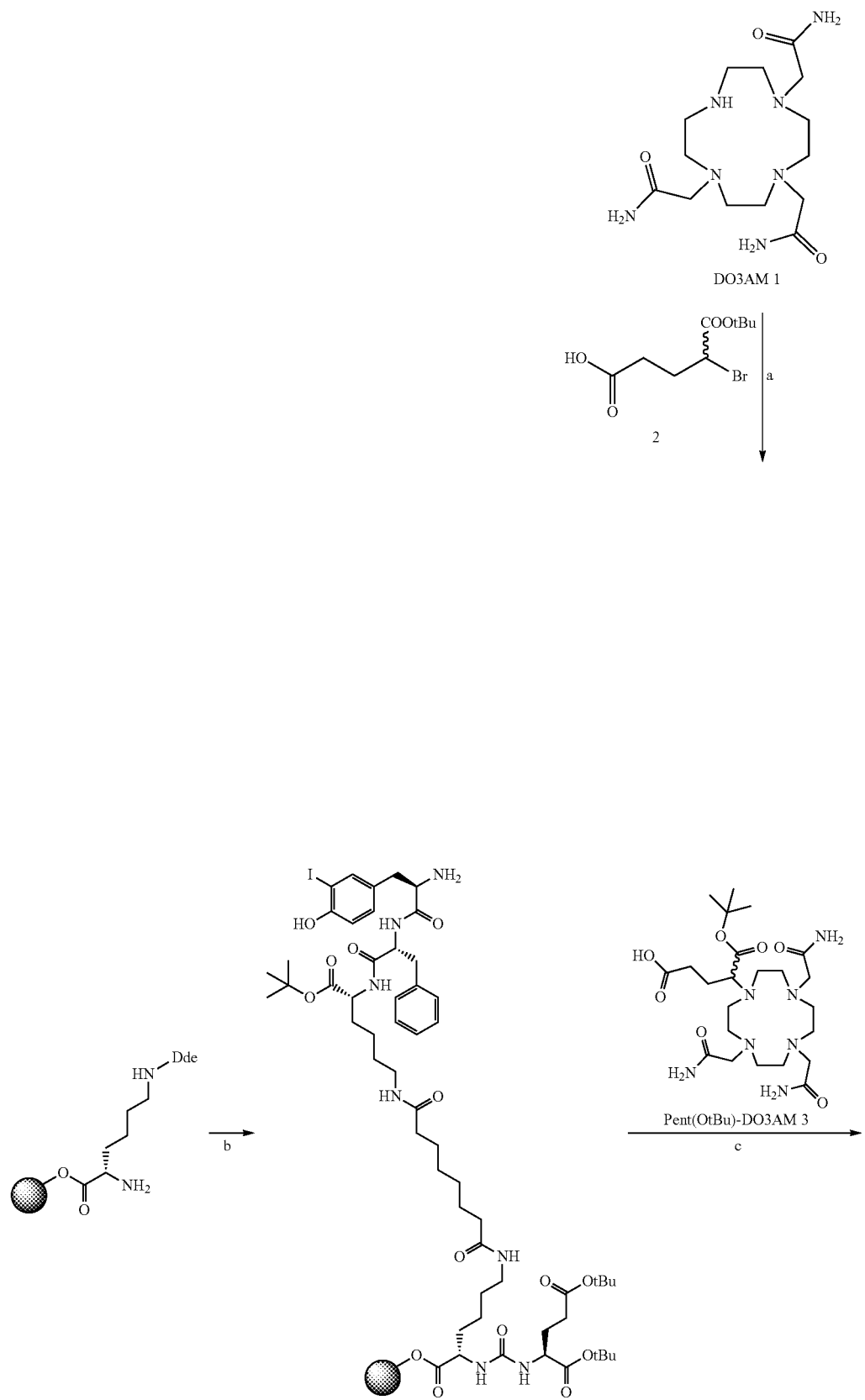

-continued

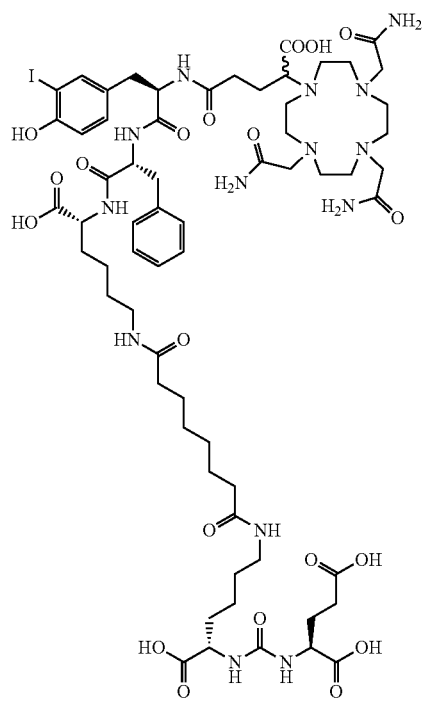

(reagents and conditions): a) K$_2$CO$_3$, DMF; b) i) H-L-Glu(OtBu)-OtBu·HCl, CDI, DMF, ii) 3% hydrazine, iii) suberic acid, OxymaPure®, DIC, DMF, iv) Fmoc-D-Lys-OtBu·HCl, PyBOP, DIPEA, DMF, v) 20% piperidine, DMF, vi) Fmoc-D-Phe-OH, HBTU, DIPEA, DMF, vii) 20% piperidine in DMF, then Fmoc-3-Iodo-D-Tyr-OH, OxymaPure®, DIC, DMF; c) i) 20% piperidine in DMF then 3, HATU, DIPEA, DMF; ii) 92.5:5:2.5 TFA/H$_2$O/TIPS.

H-L-Lys(Dde)-2-chloro-trityl functionalised polystyrene resin (at either 0.26 mmol/g or 0.59 mmol/g) was swelled in DMF for 30 to 120 minutes, after which the DMF was drained. A solution of H-L-Glu(OtBu)-OtBu·HCl (2 equiv) was dissolved in DMF using sonication and 1,1-carbonyldiimidazole (2 equiv) was added. The solution was transferred to resin and periodically agitated over 16 to 24 h. The resin was drained and washed with DMF. This was followed by selective removal of the Dde protecting group with a solution of 3% hydrazine in DMF. The resin was drained, washed with DMF, and a solution of suberic acid (5 equiv), ethyl cyano(hydroxyimino)acetate (10 equiv; also known as OxymaPure®) and DIC (10 equiv) in DMF was added. The resin was agitated for 24 h, drained, and rinsed with DMF. A solution of Fmoc-D-Lys-OtBu·HCl (2 equiv), PyBOP (2 equiv) and DIPEA (4 equiv) in DMF was added to the resin and periodically agitated over 24 h. The resin was again drained, washed with DMF, and the exposed Fmoc group was removed using 20% piperidine in DMF, followed by washing with DMF. The resin was treated with a solution of Fmoc-D-Phe-OH (2 equiv), HBTU (2 equiv) and DIPEA (4 equiv) in DMF, with periodic agitation over 24 h (complete coupling achieved after 2 h), followed by Fmoc deprotection using 20% piperidine and subsequent rinses with DMF. A solution of Fmoc-3-Iodo-D-Tyr-OH (2 equiv), ethyl cyano (hydroxyimino)acetate (2 equiv) and DIC (4 equiv) in DMF was added to the resin and the resin was periodically agitated for 24 h (complete coupling achieved after 2 h). The remaining Fmoc group was removed using 20% piperidine and the resin was rinsed with DMF. A solution of Pent (OtBu)-DO3AM (2 equiv), HATU (6 equiv) and DIPEA (4 equiv) in DMF was added to the resin and the resin was periodically agitated until monitoring via regular (approximately every 10 min) ninhydrin tests indicated reaction completion. The resin was washed with DMF, DCM and diethyl ether. Cleavage and deprotection of peptide was achieved using an 92.5:5:2.5 mix of TFA/H$_2$O/TIPS, for at least 16 hours. The crude peptide conjugate was precipitated with diethyl ether, separated by centrifugation, and purified by preparative TFA-based HPLC over reversed-phase C18 silica (Eluent A: 0.1% TFA/Milli-Q water; Eluent B: 0.1% TFA/50% CH$_3$CN/Milli-Q water; Gradient: hold at 20% B for 20 minutes, then 20-70% B over 75 minutes) and lyophilized to give a white powder. The purified peptide conjugate was dissolved at 1 mg/mL concentration in 2 mM HCl in 25% ACN/Milli-Q water, filtered through a sterile disposable 0.22 micron filter, and lyophilised for at least 24 h. Purity of ADVC001 was 98.6% by HPLC (Rt=4.6 min, 18% Solvent B for 5 min, 40% solvent B over 6 min) and as HCl salt. Calculated mass (C$_{63}$H$_{95}$IN$_{14}$O$_{20}$)=1494.6, found m/z [M+H$^+$]: 1495.1.

Example 3: Radiolabeling of ADVC001 with $^{212}$Pb

A solution of [$^{212}$Pb]PbCl$_2$ was buffered with 0.25 M NaOAc to pH 5.0-6.0 as judged by pH strip. A freshly prepared solution of ADVC001 in 0.25 M NaOAc (20 uL, 1 mg/mL) was added to the radioactive solution and the resulting reaction mixture was allowed to stand at ambient temperature for 30 min or until completion of reaction. An iTLC developing with 25 mM EDTA (pH 5.0) was used to monitor the reaction (unbound $^{212}$Pb R$_f$>0.7, bound $^{212}$Pb R$_f$<0.3). The reaction was formulated with sodium ascorbate (100 mg/mL). Radio-HPLC confirmed radiochemical identity against $^{nat}$Pb standard (Rt=4.83 min, 18% Solvent B for 5 min, 40% solvent B over 6 min)) and radiochemical purity >90%.

Example 4: Biodistribution of [$^{212}$Pb]Pb-ADVC001

Figure 3:
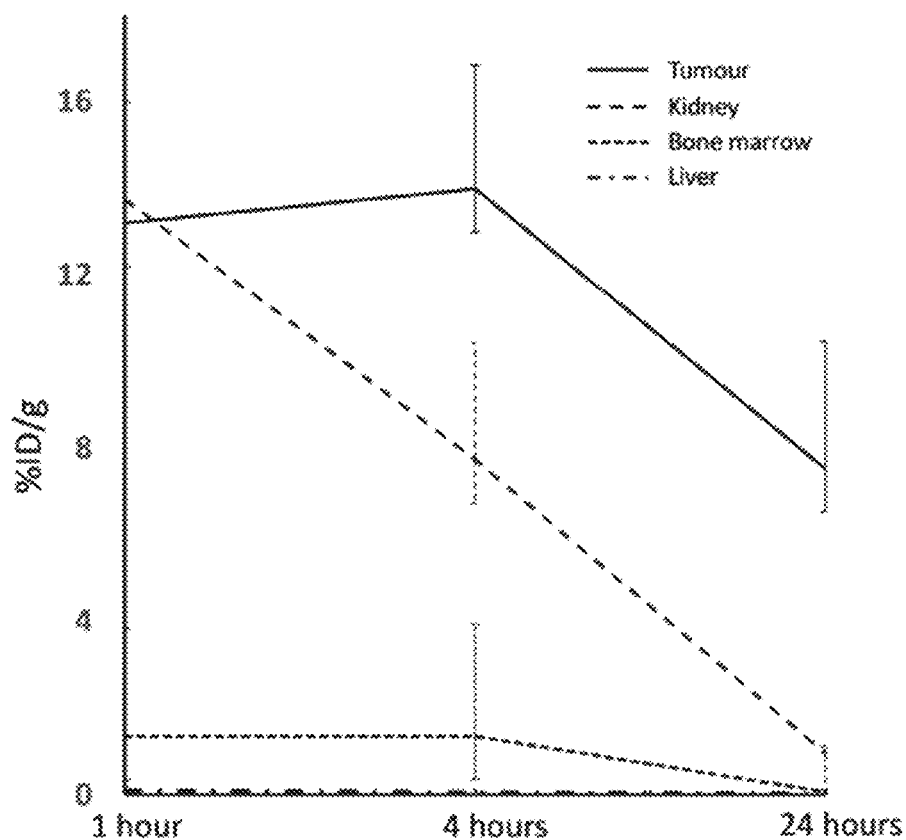
FIG. 3: [$^{212}$Pb]Pb-ADVC001 accumulation over time within PSMA expressing tumour and key organs.

In vivo biodistribution studies of [$^{212}$Pb]Pb-ADVC001 were performed using an animal model of prostate cancer. Tumour xenographs were grown on opposite flanks of male BALB/c nude mice after inoculation with $10^6$ PC3-PIP (PSMA expressing) and PC3 (PSMA deficient) cell lines. In this model, the PC3 tumours act as a control to assess the specificity of [$^{212}$Pb]Pb-ADVC001 uptake within PSMA expressing tumours. Once the tumours had reached 5-10 mm in size, 3 groups (representing 3 different time points) of 5 mice were injected with 300-325 kBq of [$^{212}$Pb]Pb-ADVC001 via the lateral tail vein. At 1, 4 and 24 hours after injection, mice were euthanised and multiple organs collected and weighed. Radioactivity in each organ was counted using a well-type gamma counter (counting window 218-258 keV). Activity levels of [$^{212}$Pb]Pb-ADVC001 expressed as percent injected dose/gram of tissue (% ID/g) measured from each organ over the 3 time points are given in Table 1 with the biodistribution plots presented in FIG. 1A. Activity accumulation over time of [$^{212}$Pb]Pb-ADVC001 for major organs (kidney, liver and bone marrow) along with tumour uptake is provided in FIG. 3.

TABLE 1

Activity (mean percent injected dose per gram) of [$^{212}$Pb]Pb-ADVC001

| % ID/g | 1 hour Mean | SD | 4 hours Mean | SD | 24 hours Mean | SD |
|---|---|---|---|---|---|---|
| Liver | 0.096 | 0.049 | 0.046 | 0.005 | 0.028 | 0.004 |
| Spleen | 0.964 | 0.144 | 0.182 | 0.039 | 0.072 | 0.013 |
| Kidney | 13.738 | 4.002 | 7.730 | 2.686 | 0.950 | 0.182 |
| Heart | 0.292 | 0.191 | 0.108 | 0.080 | 0.034 | 0.008 |
| Lungs | 0.308 | 0.081 | 0.234 | 0.210 | 0.066 | 0.019 |
| Pancreas | 0.292 | 0.304 | 0.080 | 0.018 | 0.022 | 0.013 |
| Stomach | 0.118 | 0.069 | 0.176 | 0.149 | 0.038 | 0.030 |
| Muscle | 0.172 | 0.052 | 0.534 | 0.911 | 0.024 | 0.005 |
| Bone/Marrow | 1.346 | 2.485 | 1.356 | 2.575 | 0.070 | 0.035 |
| Blood | 0.770 | 0.817 | 0.168 | 0.064 | 0.068 | 0.022 |
| PSMA negative tumour | 0.292 | 0.206 | 0.756 | 1.349 | 0.044 | 0.011 |
| PSMA positive tumour | 13.196 | 2.775 | 13.988 | 2.847 | 7.516 | 2.938 |
| Brain | 0.046 | 0.009 | 0.060 | 0.048 | 0.018 | 0.008 |
| Gut | 0.234 | 0.283 | 0.196 | 0.140 | 0.086 | 0.081 |
| Tail | 0.580 | 0.177 | 0.302 | 0.131 | 0.040 | 0.023 |
| Carcass | 1.498 | 1.204 | 1.022 | 1.029 | 0.016 | 0.005 |

In vivo biodistribution studies over a 24-hour period for [$^{212}$Pb]Pb-ADVC001 revealed high specific uptake of the radiopharmaceutical within PSMA positive tumours with very low uptake in other organs including the control tumour site. The agent is rapidly cleared from the body as evidenced by the significant reduction in activity within the kidneys over a 24-hour period. The activity ratio of PSMA expressing tumours versus PSMA deficient tumours was 44.9, 18.5 and 170.8 at 1, 4 and 24 hours respectively. These results highlight the high specific uptake and retention of [$^{212}$Pb]Pb-ADVC001 in PSMA expressing tumours with minimal binding in the kidneys.

Figure 1B:
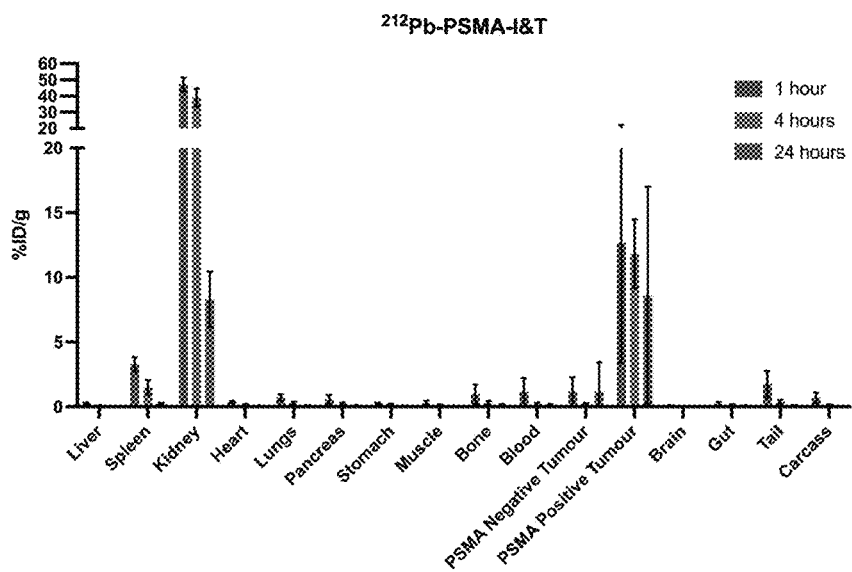
Figure 2A:
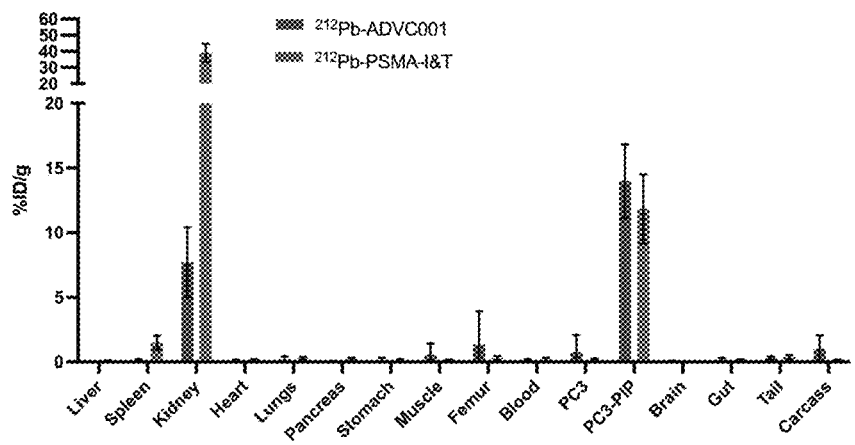
FIGS. 2A and 2B: A) Uptake and retention of [$^{212}$Pb]Pb-ADVC001 (green) and [$^{212}$Pb]Pb-PSMA-I&T (blue) in kidneys (% ID/g) 4 hours post-injection. B) Tumour:kidney ratio of $^{212}$Pb-ADVC001 (green) and [$^{212}$Pb]Pb-PSMA-I&T (blue) 1 hour, 4 hours and 24 hours post-injection. B) [$^{212}$Pb]Pb-ADVC001 exhibits high uptake and retention in PSMA-expressing tumour tissue with very fast systemic and renal clearance and minimal retention in kidney tissue leading a higher tumour:kidney ratio compared to [$^{212}$Pb]Pb-PSMA-I&T.
Figure 2B:
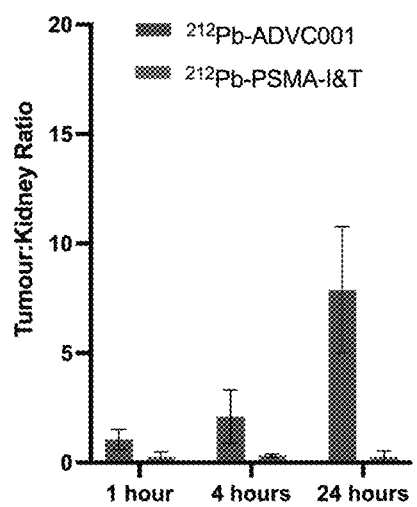

Example 7: Biodistribution of [$^{212}$Pb]Pb-ADVC001 Compared to [$^{212}$Pb]Pb-PSMA The biodistribution study of Example 7 was repeated using [$^{212}$Pb]-PSMA-I&T instead of [$^{212}$Pb]Pb-ADVC001. The biodistribution of [$^{212}$Pb]Pb-PSMA-I&T expressed as percent injected dose/gram of tissue (% ID/g) measured from each organ over the 3 time points is presented in FIG. 1B. FIG. 2A compares the biodistribution of [$^{212}$Pb]Pb-ADVC001 and [$^{212}$Pb]Pb-PSMA-I&T in each organ at 4 hours after injection The tumour to kidney activity ratio provides a measure to compare the uptake and clearance of different radiopharmaceuticals in relevant animal models. The tumour to kidney activity ratios for [$^{212}$Pb]Pb-ADVC001 and [$^{212}$Pb]Pb-PSMA-I&T are summarised in FIG. 2B. [$^{212}$Pb]Pb-ADVC001 presents with a significantly higher tumour to kidney activity ratio across all time points compared to [$^{212}$Pb]Pb-PSMA-I&T.

Overall, [$^{212}$Pb]Pb-ADVC001 exhibits high uptake and retention in PSMA positive tumour tissue with very fast systemic and renal clearance and minimal retention in kidney tissue leading to a high tumour:kidney ratio compared to [$^{212}$Pb]Pb-PSMA I&T. This surprising result is demonstrates the utility of [$^{212}$Pb]Pb-ADVC001 as a therapeutic radiopharmaceutical for the treatment of PSMA expressing cancer as high uptake and retention in the kidneys can lead to damage and subsequent nephrotoxicity, limiting the dose that can be administered which would ultimately limit the efficacy of the therapy. Based on the biodistribution data, [$^{212}$Pb]Pb-ADVC001 is expected to be a more efficacious therapy than [$^{212}$Pb]Pb-PSMA-I&T.

Example 8: Dosimetry of [$^{212}$Pb]Pb-ADVC001

Dosimetry estimates in animal model organs were calculated using the Organ Level Internal Dose Assessment (OLINDA) method which is recognised by the FDA for dosimetry modelling (Stabin, M. et al. OLINDA/EXM: *The Second-Generation Personal Computer Software for Internal Dose Assessment in Nuclear Medicine*). Activity levels were fitted using an exponential function to derive Time-Integrated Activity Coefficients (TIAC) which represent the area under the time-activity curve or absorbed dose for each organ. The internal dose (mSv/MBq) was then calculated based on the organ weight and radiation emission profile of $^{212}$Pb. In this case, the dose from all daughter nuclides ($^{212}$Pb, $^{212}$Bi, $^{212}$Po and $^{208}$Tl) were summed to provide a dose estimate for each organ which are provided in Table 2. The biodistribution data derived for [$^{212}$Pb]Pb-ADVC001 identified the kidneys as the organ at most risk of radiation injury. The dose estimates for the kidney's for [$^{212}$Pb]Pb-ADVC001 was 0.04406 mSv/MBq. These very favourable dose estimates reflect the rapid clearance of [$^{212}$Pb]Pb-ADVC001 from the kidneys. The mean percent injected dose per gram (% ID/g) of [$^{212}$Pb]Pb-ADVC001 at 1 and 24 hours were 13.73 and 0.95, respectively. These dose estimates derived for [$^{212}$Pb]Pb-ADVC001 are very favourable in terms of reduced risk to sensitive organs.

TABLE 2

| Dose estimates of [$^{212}$Pb]Pb-ADVC001 | |
|---|---|
| Organ | Dose (mSv/MBq) |
| Adrenals | 0.00110 |
| Brain | 0.00006 |
| Esophagus | 0.00434 |
| Gallbladder wall | 0.00100 |
| Left colon | 0.00534 |
| Small Intestine | 0.00100 |
| Stomach wall | 0.01209 |
| Right colon | 0.00531 |
| Rectum | 0.00250 |
| Heart wall | 0.00049 |
| Kidneys | 0.04406 |
| Liver | 0.00081 |
| Lungs | 0.00206 |
| Pancreas | 0.00106 |
| Prostate | 0.00050 |
| Salivary glands | 0.00109 |
| Red marrow | 0.01546 |
| Osteogenic cells | 0.00472 |
| Spleen | 0.00153 |
| Testes | 0.00434 |
| Thymus | 0.00100 |
| Thyroid | 0.00434 |
| Urinary bladder wall | 0.00438 |
| Effective Dose | 0.1197 |

The invention claimed is:

1. A compound of Formula (II) having the following structure:

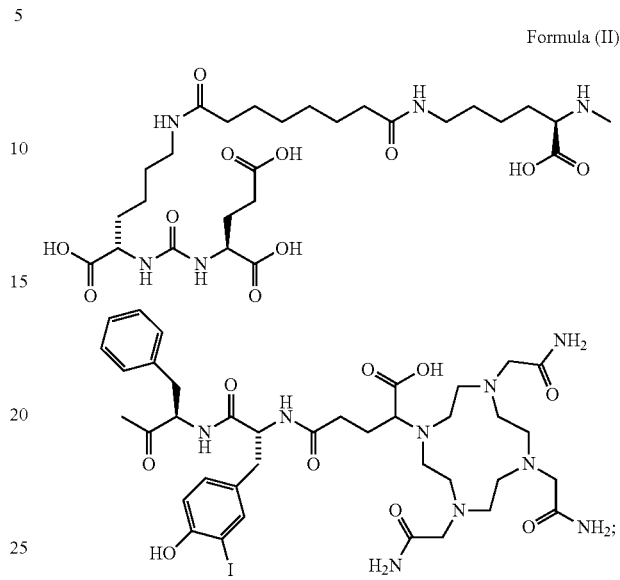

Formula (II)

wherein the compound of Formula (II) is also referred to as (3S,7S,26R,29R,32R)-29-benzyl-32-(4-hydroxy-3-iodobenzyl)-5,13,20,28,31,34-hexaoxo-37-(4,7,10-tris(2-amino-2-oxoethyl)-1,4,7,10-tetraazacyclododecan-1-yl)-4,6, 12,21,27,30,33-heptaazaheptatriacontane-1,3,7,26,37-pentacarboxylic acid, or a pharmaceutically acceptable salt or solvate, thereof; where the compound of Formula (II) is complexed to $^{212}$Pb.

2. A compound of Formula (III) having the following structure:

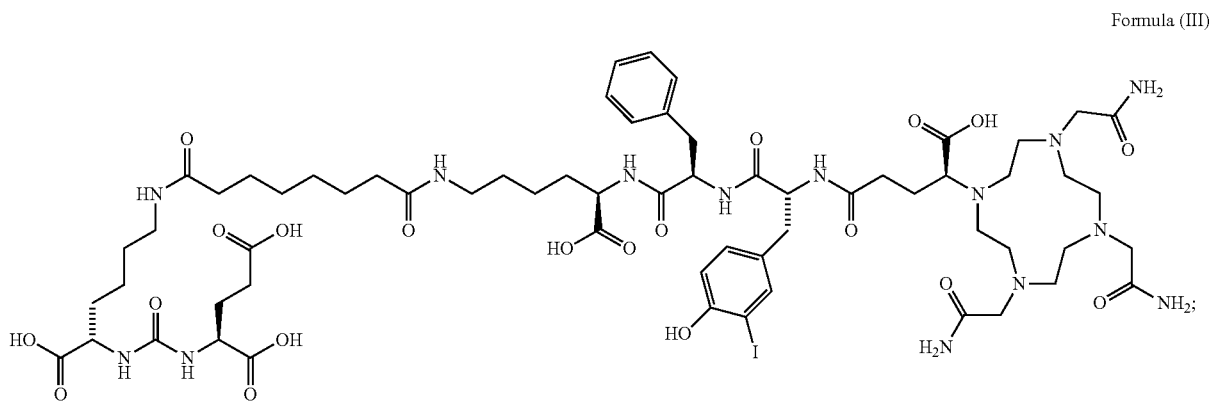

Formula (III)

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof, wherein the compound of Formula (III) is complexed to $^{212}$Pb.

3. The compound of claim 2, comprising a compound of Formula (III) having the following structure:

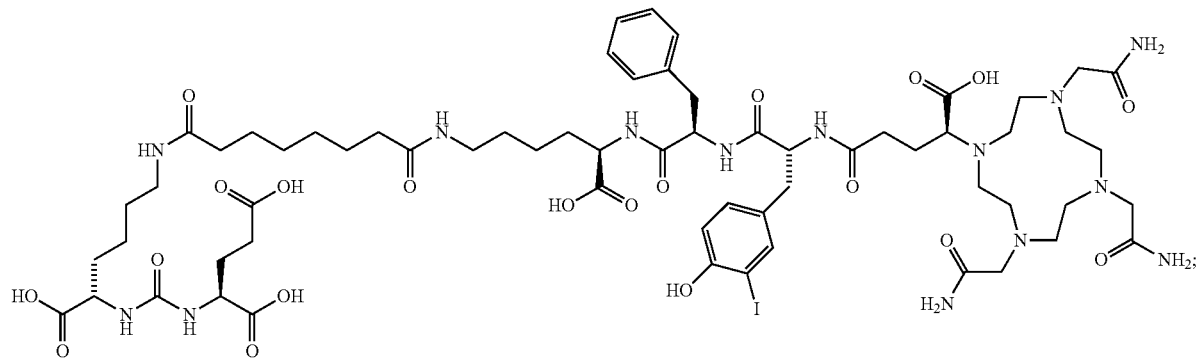

Formula (III)

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, wherein the compound of Formula (III) is complexed to $^{212}$Pb.

4. A comprising a compound of Formula (IV) having the following structure:

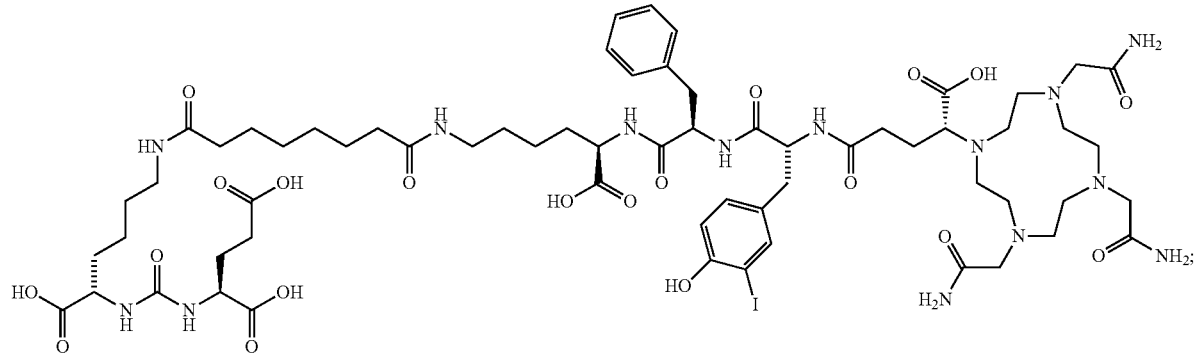

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7, 10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof, wherein the compound of Formula (IV) is complexed to $^{212}$Pb.

5. The compound of claim 4, comprising a compound of Formula (IV) having the following structure:

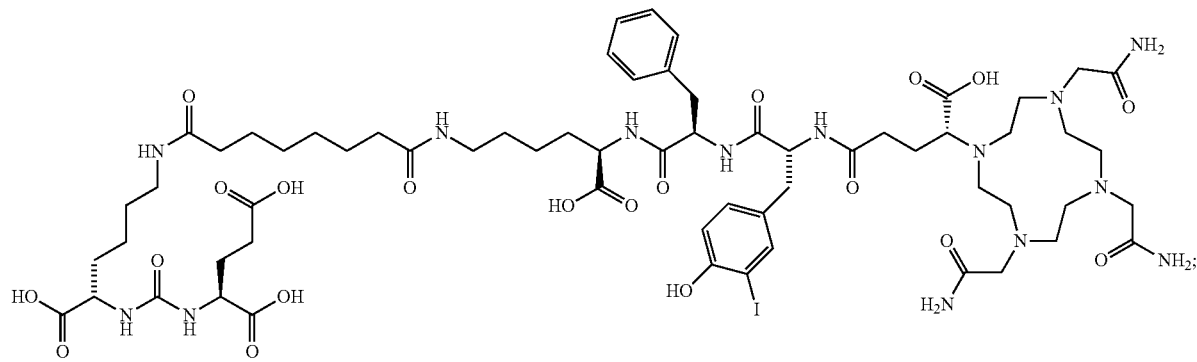

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, wherein the compound of Formula (IV) is complexed to $^{212}$Pb.

6. A pharmaceutical composition comprising a therapeutically effective amount of a compound of Formula (II) having the following structure:

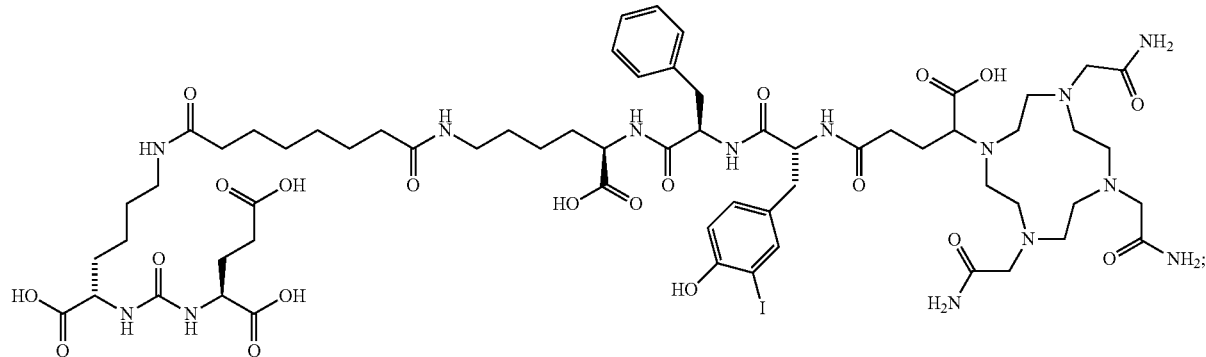

Formula (II)

wherein the compound of Formula (II) is also referred to as (3S,7S,26R,29R,32R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof, where the compound of Formula (II) is complexed to 2 a pharmaceutically acceptable excipient.

7. The pharmaceutical composition of claim 6, wherein the compound of Formula (II) comprises at least 50% of a compound of Formula (III) having the following structure:

Formula (III)

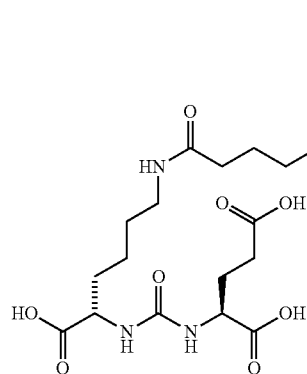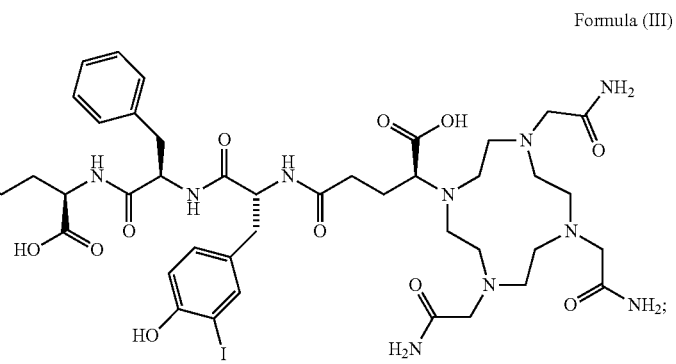

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

8. The pharmaceutical composition of claim 6, wherein the compound of Formula (II) comprises at least 50% of a compound of Formula (III) having the following structure:

Formula (III)

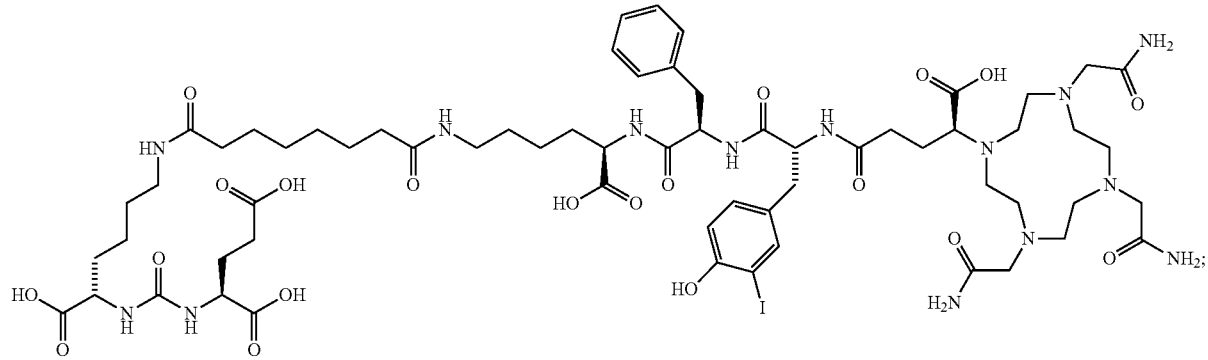

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid.

9. The pharmaceutical composition of claim 6, wherein the compound of Formula (II) comprises at least 50% of a compound of Formula (IV) having the following structure:

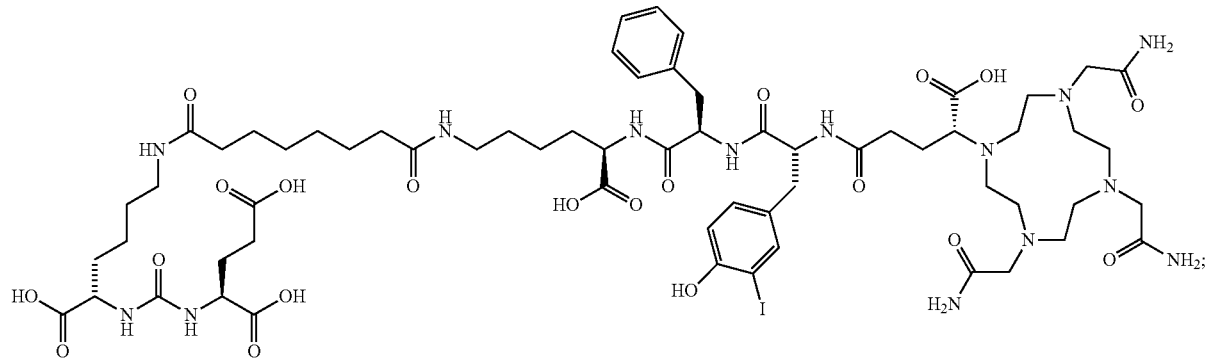

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid,
or a pharmaceutically acceptable salt or solvate thereof.

10. The pharmaceutical composition of claim 6, wherein the compound of Formula (II) comprises at least 50% of a compound of Formula (IV) having the following structure:

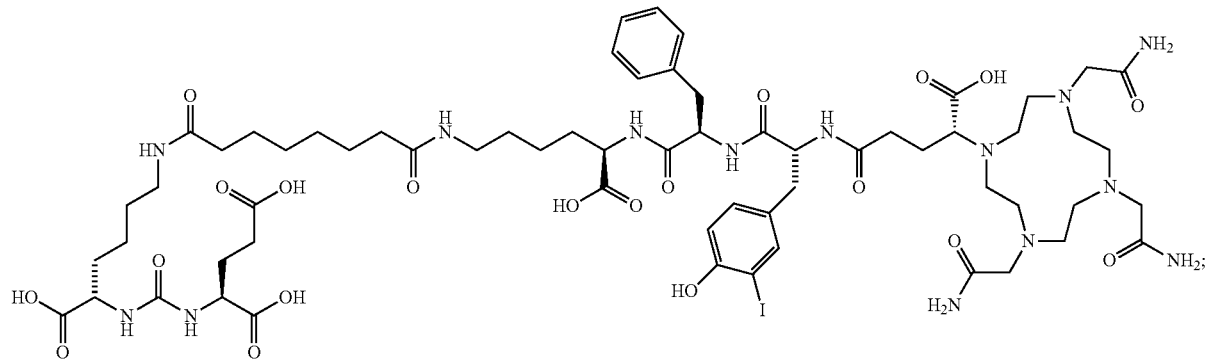

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid.

11. The pharmaceutical composition of claim 6, wherein the compound of Formula (II) comprises a compound of Formula (III) having the following structure:

Formula (III)

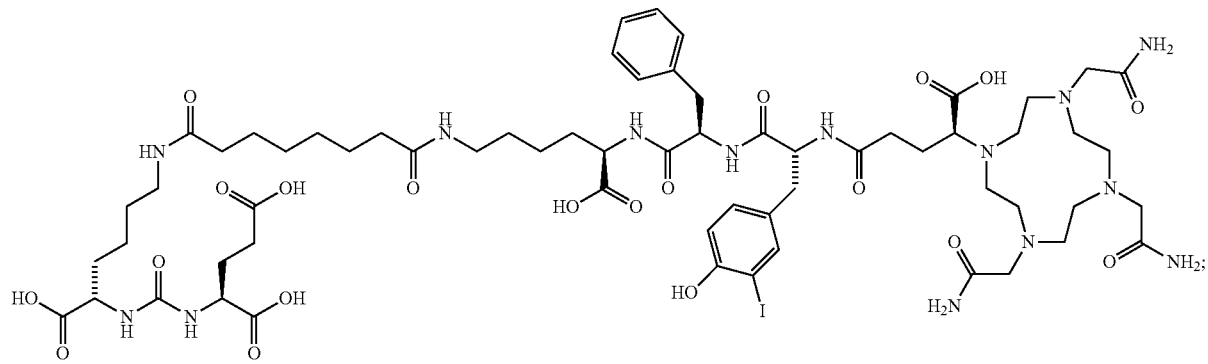

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof, and a compound of Formula (IV) having the following structure:

Formula (IV)

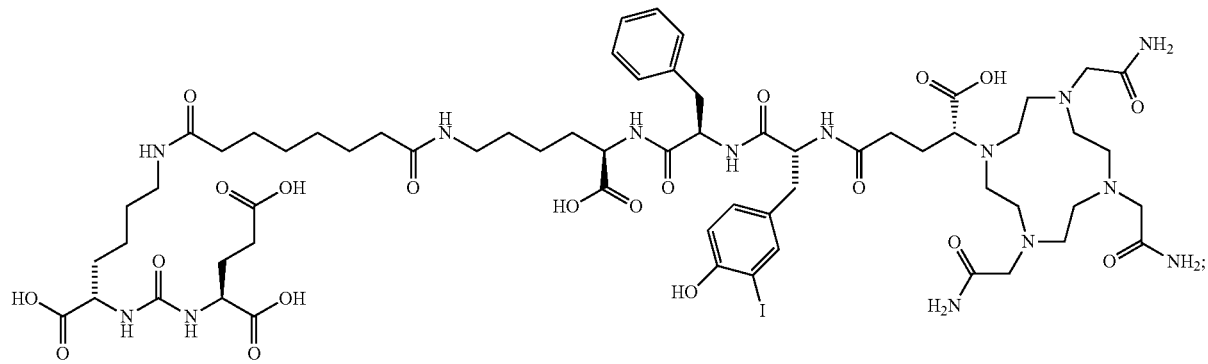

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

12. A method of treating a PSMA-expressing cancer in a patient in need thereof, comprising administering to the patient a therapeutically effective amount of a compound of Formula (II) having the following structure:

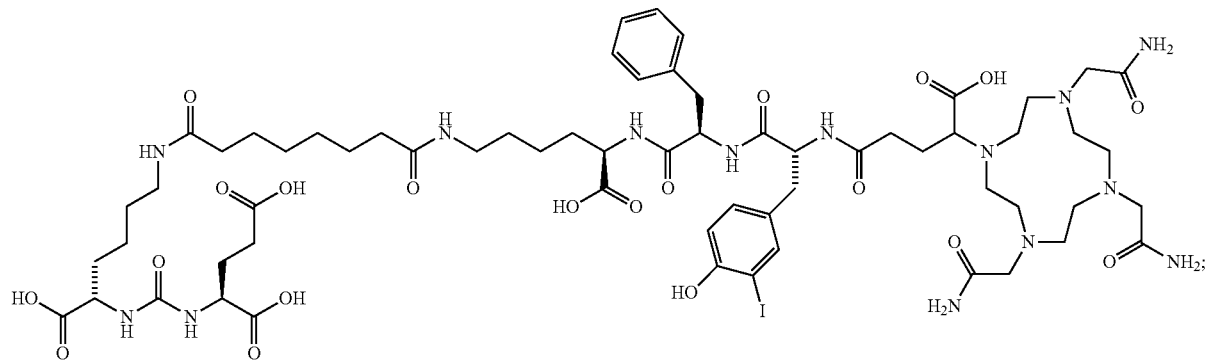

Formula (II)

wherein the compound of Formula (II) is also referred to as (3S,7S,26R,29R,32R)-29-benzyl-32-(4-hydroxy-3-iodobenzyl)-5, 13,20,28,31,34-hexaoxo-37-(4,7,10-tris(2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate, thereof, wherein the compound of Formula (II) is complexed to $^{212}$Pb, thereby treating the PSMA-expressing cancer in the patient.

13. The method of claim 12, wherein the PSMA-expressing cancer is prostate cancer.

14. The method of claim 12, wherein the compound of Formula (II) comprises at least 50% of a compound of Formula (III) having the following structure:

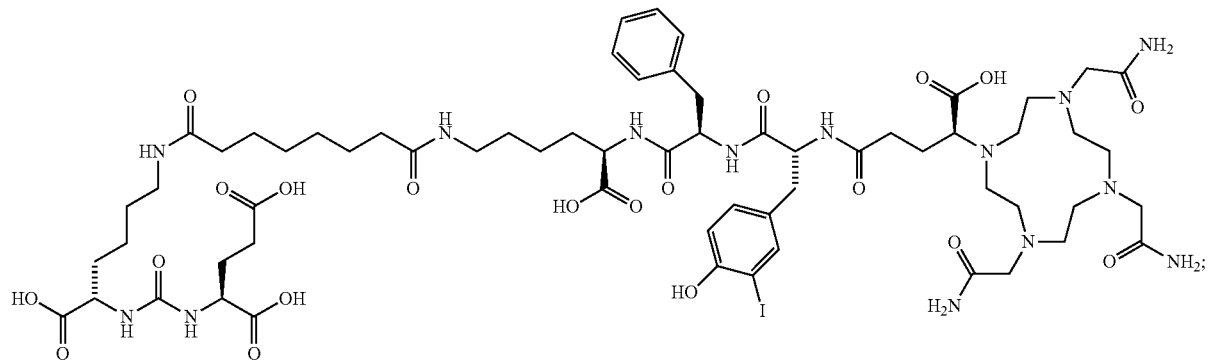

Formula (III)

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

15. The method of claim 12, wherein the compound of Formula (II) comprises at least 50% of a compound of Formula (III) having the following structure:

Formula (III)

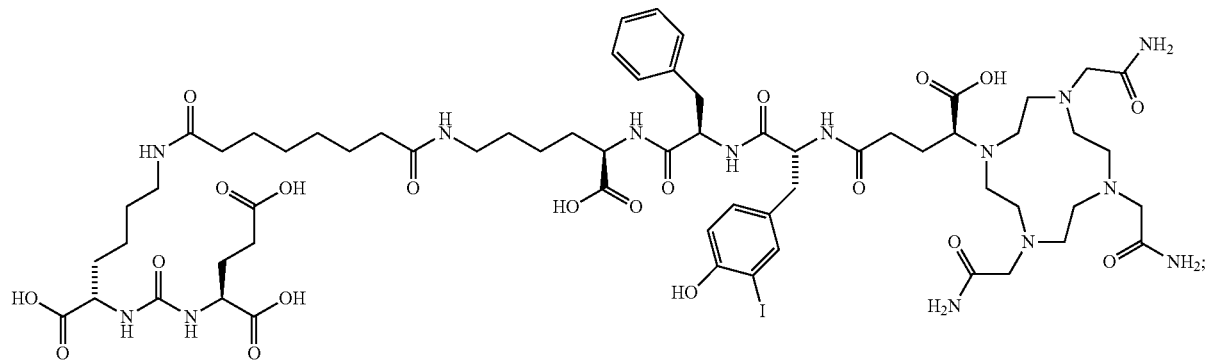

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid.

16. The method of claim 12, wherein the compound of Formula (II) comprises at least 50% of a compound of Formula (IV) having the following structure:

Formula (IV)

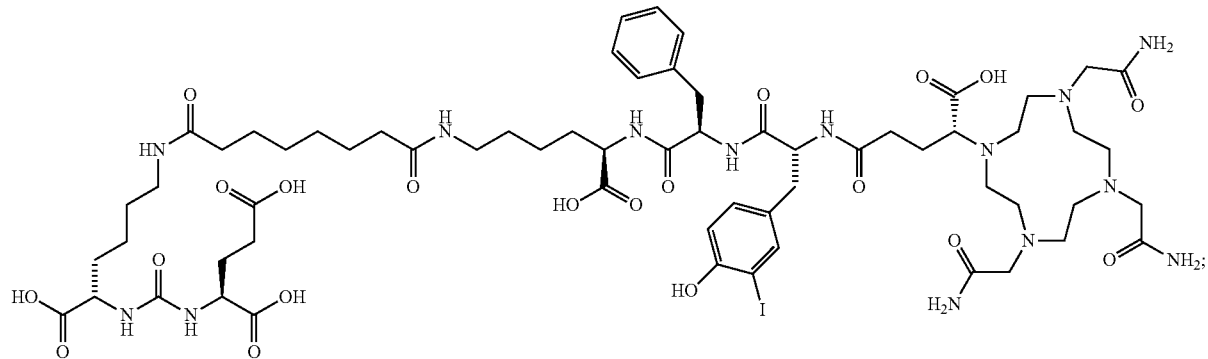

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

17. The method of claim 12, wherein the compound of Formula (II) comprises at least 50% of a compound of Formula (IV) having the following structure:

Formula (IV)

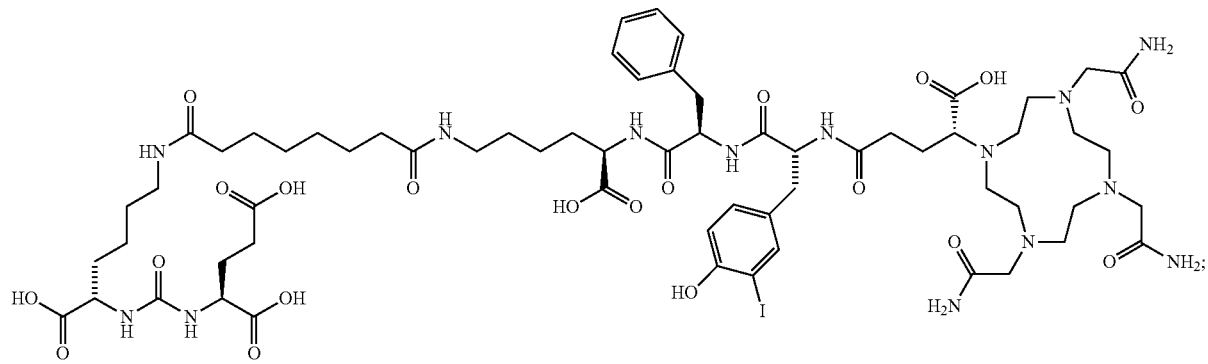

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid.

18. The method of claim 12, wherein the compound of Formula (II) comprises a compound of Formula (III) having the following structure:

Formula (III)

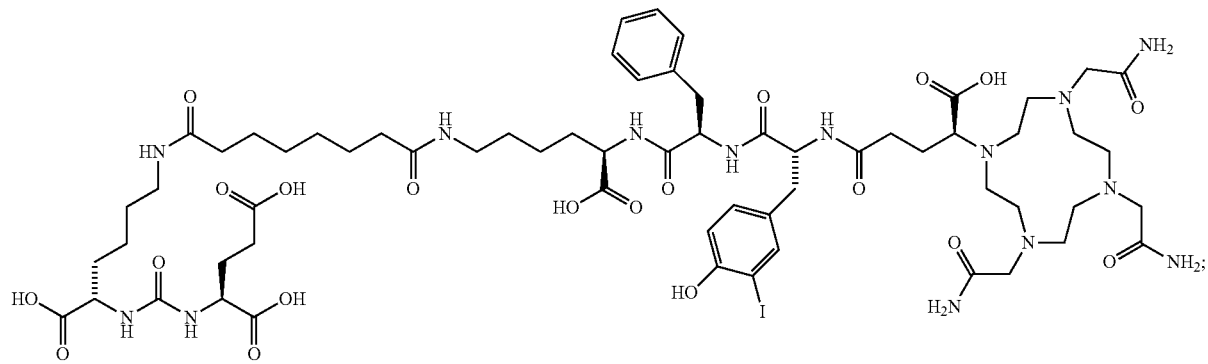

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7, 10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof, and a compound of Formula (IV) having the following structure:

Formula (IV)

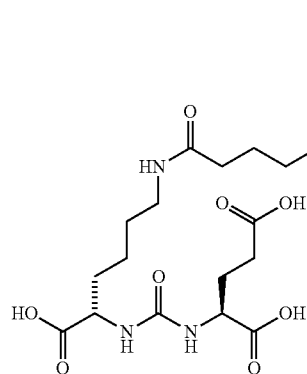
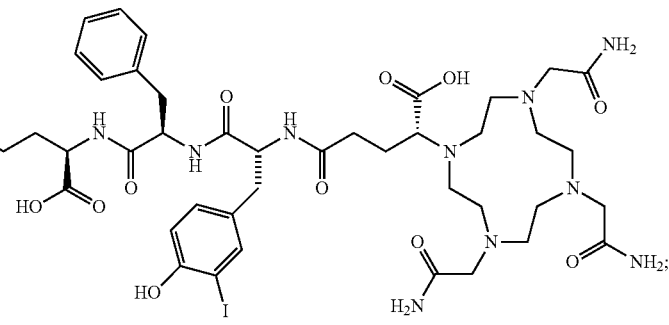

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid,
or a pharmaceutically acceptable salt or solvate thereof.

19. The method of claim 18, comprising administering to the patient a therapeutically effective amount of the compound of Formula (III) and the compound of Formula (IV) in substantially equal amounts.

20. The compound of claim 1, comprising at least 50% of a compound of Formula (III) having the following structure:

Formula (III)

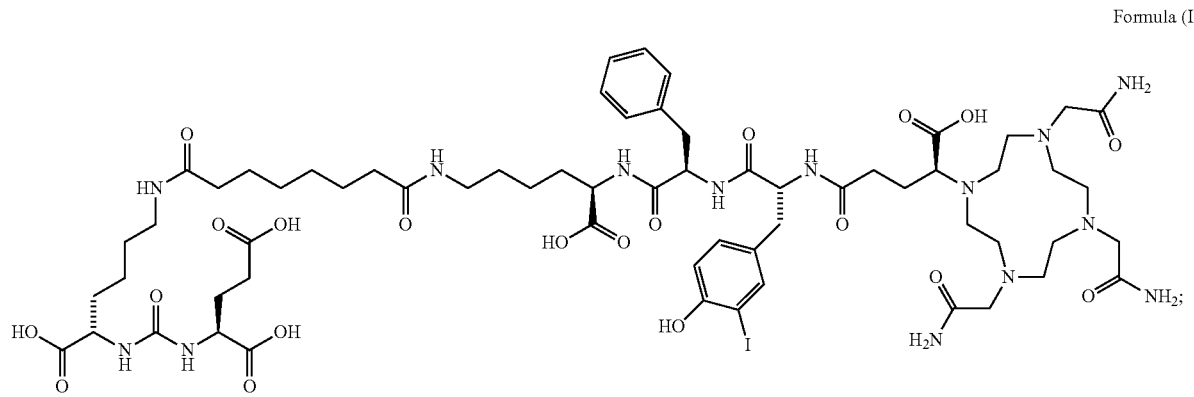

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid,
or a pharmaceutically acceptable salt or solvate thereof.

21. The compound of claim 1, comprising at least 50% of a compound of Formula (IV) having the following structure:

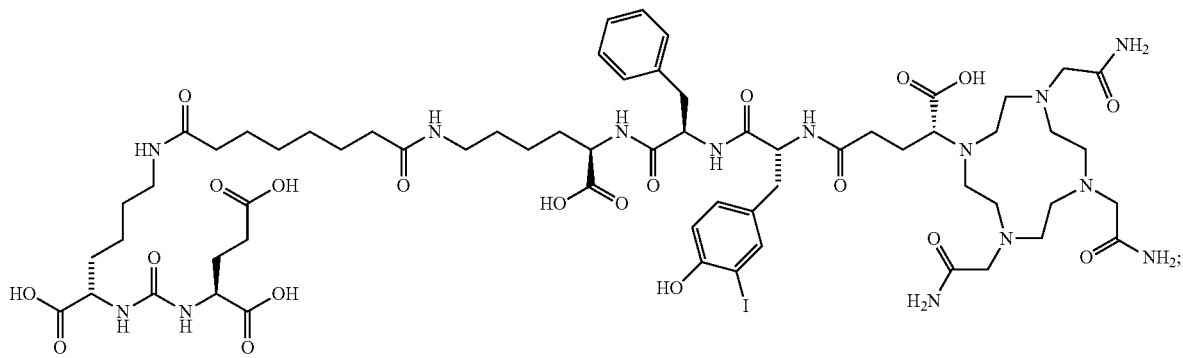

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

22. The compound of claim 1, wherein the compound is a compound of Formula (III) having the following structure:

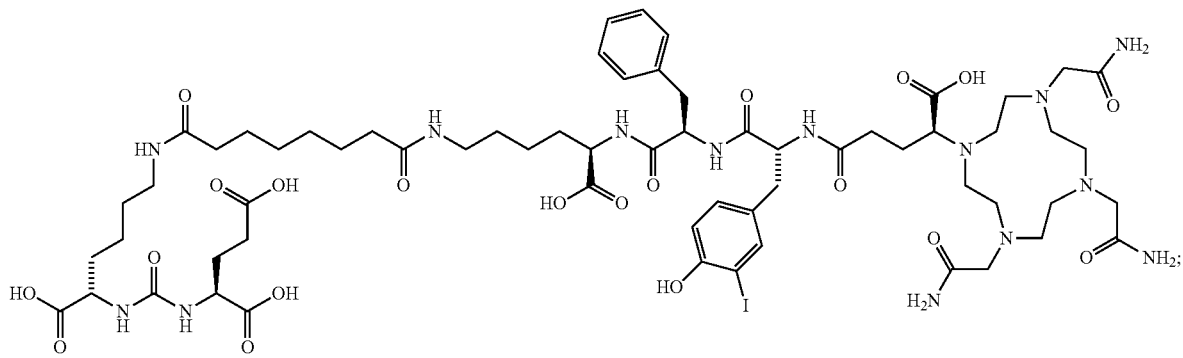

Formula (III)

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

23. The compound of claim 1, wherein the compound is a compound of Formula (IV) having the following structure:

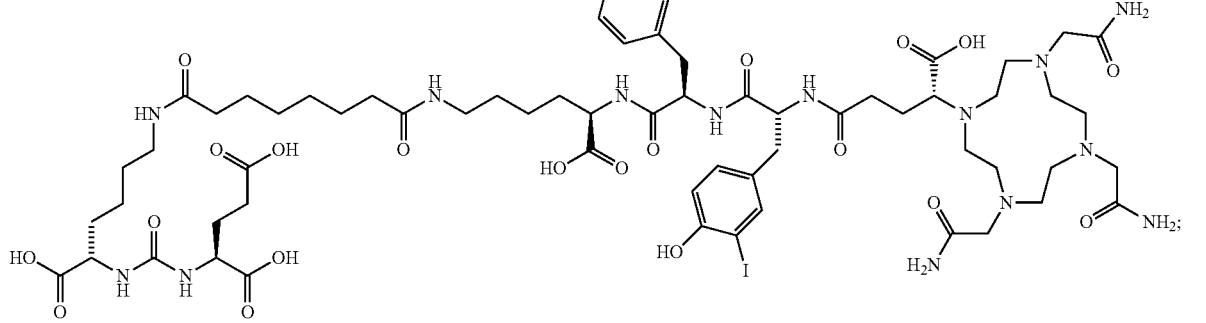

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

24. The pharmaceutical composition of claim 6, wherein the compound of Formula (II) is a compound of Formula (III) having the following structure:

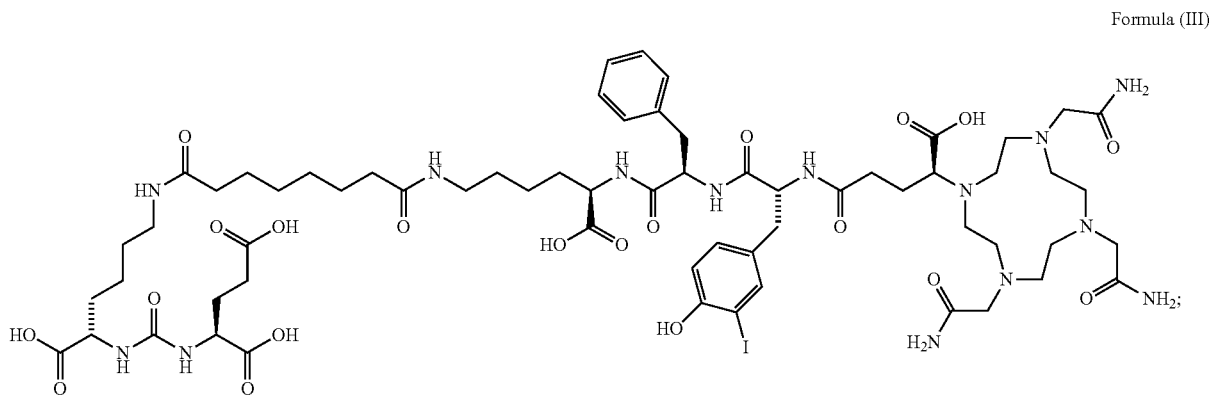

Formula (III)

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

25. The pharmaceutical composition of claim 6, wherein the compound of Formula (II) is a compound of Formula (IV) having the following structure:

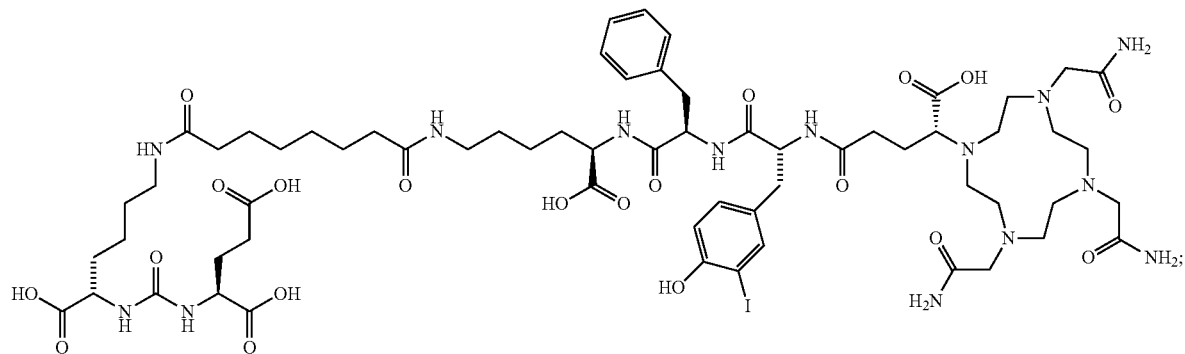

Formula (IV)

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

26. The pharmaceutical composition of claim 11, wherein the compound of Formula (II) comprises about 50% of the compound of Formula (III) and about 50% of the compound of Formula (IV).

27. The method of claim 12, wherein the compound of Formula (II) is a compound of Formula (III) having the following structure:

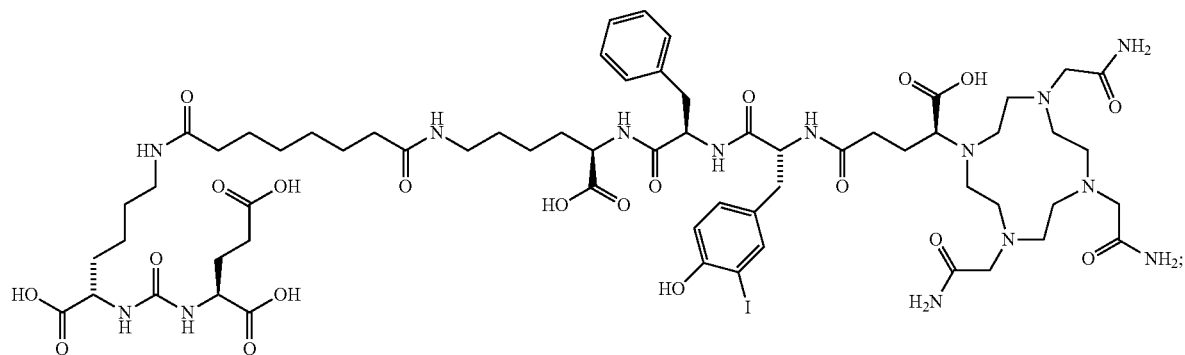

Formula (III)

wherein the compound of Formula (III) is also referred to as (3S,7S,26R,29R,32R,37S)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid, or a pharmaceutically acceptable salt or solvate thereof.

28. The method of claim 12, wherein the compound of Formula (II) is a compound of Formula (IV) having the following structure:

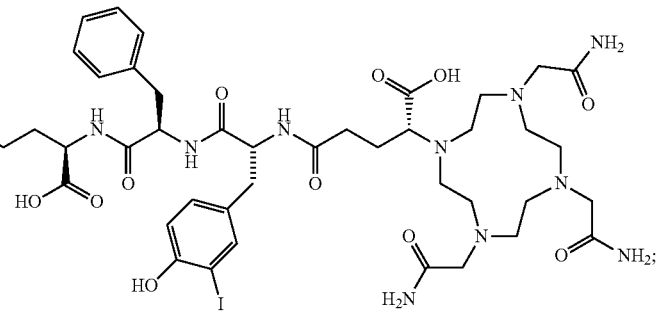

Formula (IV)

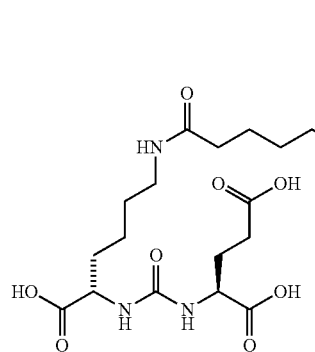

wherein the compound of Formula (IV) is also referred to as (3S,7S,26R,29R,32R,37R)-29-benzyl-32-(4-hydroxy-3-iodobenzyl)-5,13,20,28,31,34-hexaoxo-37-(4,7,10-tris (2-amino-2-oxoethyl)-1,4,7,10-tetraazacyclododecan-1-yl)-4,6,12,21,27,30,33-heptaazaheptatriacontane-1,3,7,26,37-pentacarboxylic acid,
or a pharmaceutically acceptable salt or solvate thereof.

29. The method of claim 18, wherein the compound of Formula (II) comprises about 50% of the compound of Formula (III) and about 50% of the compound of Formula (IV).

* * * * *